US011241013B2

(12) United States Patent
Urch et al.

(10) Patent No.: US 11,241,013 B2
(45) Date of Patent: Feb. 8, 2022

(54) BENZIMIDAZOLE COMPOUNDS AS AGRICULTURAL CHEMICALS

(71) Applicant: REDAG CROP PROTECTION LTD, Wigan (GB)

(72) Inventors: Christopher John Urch, Wigan (GB); Roger John Butlin, Wigan (GB); Stephania Christou, Wigan (GB); Rebecca Kathryn Booth, Wigan (GB)

( * ) Notice: Subject to any disclaimer, the term of this patent is extended or adjusted under 35 U.S.C. 154(b) by 0 days.

(21) Appl. No.: 16/755,393

(22) PCT Filed: Oct. 17, 2018

(86) PCT No.: PCT/GB2018/052989
§ 371 (c)(1),
(2) Date: Apr. 10, 2020

(87) PCT Pub. No.: WO2019/077345
PCT Pub. Date: Apr. 25, 2019

(65) Prior Publication Data
US 2021/0204547 A1    Jul. 8, 2021

(30) Foreign Application Priority Data

Oct. 18, 2017 (GB) .................................... 1717141
Jan. 30, 2018 (GB) .................................... 1801492
Jul. 4, 2018 (GB) .................................... 1810961

(51) Int. Cl.
| | | |
|---|---|---|
| *A01N 43/713* | (2006.01) |
| *C07D 403/14* | (2006.01) |
| *C07D 401/14* | (2006.01) |
| *C07D 417/14* | (2006.01) |
| *A01N 43/54* | (2006.01) |
| *A01N 43/78* | (2006.01) |
| *A01N 43/52* | (2006.01) |
| *C07D 405/14* | (2006.01) |
| *A01N 43/84* | (2006.01) |

(52) U.S. Cl.
CPC ........... *A01N 43/713* (2013.01); *A01N 43/52* (2013.01); *A01N 43/54* (2013.01); *A01N 43/78* (2013.01); *A01N 43/84* (2013.01); *C07D 401/14* (2013.01); *C07D 403/14* (2013.01); *C07D 405/14* (2013.01); *C07D 417/14* (2013.01)

(58) Field of Classification Search
CPC ...... A01N 43/713; A01N 43/84; A01N 43/78; A01N 43/52; C07D 403/14; C07D 401/14; C07D 417/14; C07D 405/14
See application file for complete search history.

(56) References Cited

FOREIGN PATENT DOCUMENTS

| | | |
|---|---|---|
| CN | 103059003 A | 3/2014 |
| WO | 199957103 A1 | 11/1999 |
| WO | 2007085660 A1 | 8/2007 |
| WO | 2008132434 A2 | 11/2008 |
| WO | 2012/136581 A1 * | 10/2012 |
| WO | 2012136581 A1 | 10/2012 |
| WO | 2013186229 A1 | 12/2013 |
| WO | 2016055802 A1 | 4/2016 |
| WO | 2017178819 A2 | 10/2017 |
| WO | 2018130838 A1 | 7/2018 |
| WO | 2019077344 * | 4/2019 |

OTHER PUBLICATIONS

International Search Report and Written Opinion for International Application No. PCT/GB2018/052989 dated Dec. 11, 2018, 13 pages.
Search Report Under Section 17(5), for International Application GB1717141.4, dated Jun. 21, 2018, 5 pages.

* cited by examiner

*Primary Examiner* — Tracy Vivlemore
*Assistant Examiner* — Ebenezer O Sackey
(74) *Attorney, Agent, or Firm* — Morgan, Lewis & Bockius LLP

(57) ABSTRACT

The present invention relates to benzimidazole ethers and related compounds which are of use in the field of agriculture as fungicides.

17 Claims, No Drawings

BENZIMIDAZOLE COMPOUNDS AS AGRICULTURAL CHEMICALS

This application is the U.S. national stage application of International (PCT) Patent Application Serial No. PCT/GB2018/052989, filed Oct. 17, 2018, which claims the benefit of and priority to GB Application No. 1717141.4, filed Oct. 18, 2017, GB Application No. 1801492.8, filed Jan. 30, 2018, and GB Application No. 1810961.1, filed Jul. 4, 2018. The entire disclosure of each of these applications is hereby incorporated by reference.

The present invention relates to benzimidazole ethers and related compounds which are of use in the field of agriculture as fungicides.

Given the global increase in demand for food, there is an international need for new treatments to reduce food crop losses to disease, insects and weeds. Over 40% of crops are lost before harvest, and 10% post harvest, worldwide. Losses have actually increased since the mid-1990s.

A new threat contributing to this is the emergence of chemical-resistant organisms, for example, glyphosate-resistant weeds in USA and strobilurin-resistant strains of *septoria* fungal species.

Recent research also suggests that the geographical spread of many crop pests and diseases is increasing, possibly as a result of global warming.

WO2012/136581 and WO2016/055802 provide a range of tetrazole containing compounds that have proved active as fungicides.

An aim of certain embodiments of the present invention is to provide pesticides (e.g. fungicides) which have activity either non-selectively, i.e. broad spectrum activity, or which are active specifically against selective target organisms.

An aim of certain embodiments of the present invention is to provide compounds which are less persistent in the environment after use than prior art compounds. Alternatively or additionally the compounds of the present invention may be less prone to bioaccumulation once in the food chain than prior art compounds.

Another aim of certain embodiments of the invention is to provide compounds which are less harmful to humans than prior art compounds.

Alternatively or additionally, the compounds of the invention may be less harmful than prior art compounds to one or more of the following groups: amphibians, fish, mammals (including domesticated animals such as dogs, cats, cows, sheep, pigs, goats, etc.), reptiles, birds, and beneficial invertebrates (e.g. bees and other insects, or worms), beneficial nematodes, beneficial fungi and nitrogen-fixing bacteria.

Certain compounds of the invention may be as active or more active than prior art compounds. They may have activity against organisms which have developed a resistance to prior art compounds. However, certain embodiments of the present invention may also concern compounds which have a lower level of activity relative to prior art compounds. These lower activity compounds are still effective as fungicides but may have other advantages relative to existing compounds such as, for example, a reduced environmental impact.

Certain compounds of the invention may be more selective than prior art compounds, i.e. they may have better, similar or even slightly lower activity than prior art compounds against target species but have a significantly lower activity against non-target species (e.g. the crops which are being protected).

Certain embodiments of the invention provide compounds that achieve one or more of the above aims. The compounds may be active in their own right or may metabolise or react in aqueous media to yield an active compound.

SUMMARY OF THE INVENTION

In a first aspect of the invention is provided a compound of formula (I), or an agronomically acceptable salt or N-oxide thereof:

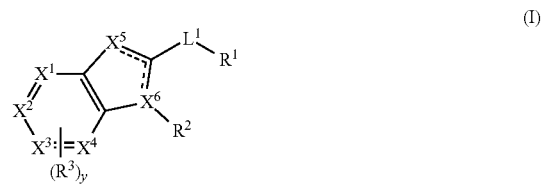

(I)

wherein $-L^1-$ is independently $-(CR^4R^4)_n-O-C(R^4R^4)_n-$;

wherein $X^1$, $X^2$, $X^3$ and $X^4$ are each selected from carbon and nitrogen; wherein no more than three of $X^1$, $X^2$, $X^3$ and $X^4$ are nitrogen;

▬▬▬ is selected from a double bond or a single bond; $X^6$ is independently selected from N and C; wherein when $X^6$ is N, the ▬▬▬ bond to which $X^6$ is attached is a single bond, the ▬▬▬ bond to which $X^5$ is attached is a double bond and $X^5$ is selected from N and $CR^{5a}$; or when $X^6$ is C, the ▬▬▬ bond to which $X^6$ is attached is a double bond, the ▬▬▬ bond to which $X^5$ is attached is a single bond, and $X^5$ is $NR^{5b}$;

$R^1$ is a heteroaryl group independently selected from thiazole, and 6-, 9- or 10-membered heteroaryl group, wherein said heteroaryl group is optionally substituted with a single $R^6$ group and/or from 1 to 4 $R^7$ groups; wherein $R^1$ has a nitrogen atom in the ring by which $R^1$ is attached to the rest of the molecule, said nitrogen atom being directly attached to the carbon atom in the ring by which $R^1$ is attached to the rest of the molecule (i.e. to $L^1$);

$R^2$ is independently selected from 5- or 6-membered heteroaryl, optionally further substituted with from 1 to 4 $R^8$ groups;

$R^3$, $R^7$ and $R^8$ are each independently at each occurrence selected from: halo, nitro, cyano, $NR^9R^{10}$, $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl, and $-O-C_1$-$C_6$-haloalkyl;

$R^4$ is independently selected from H, F, $C_1$-$C_4$-alkyl and $C_1$-$C_4$-haloalkyl; or two $R^4$ groups that are attached to the same carbon, together with the carbon to which they are attached, form a $C_3$-$C_5$-cycloalkyl group;

$R^{5a}$ is independently selected from H, halo and $C_1$-$C_4$-alkyl;
$R^{5b}$ is independently selected from H and $C_1$-$C_4$-alkyl;
$R^6$ is independently selected from H and $NHR^{13}$;
$R^9$ is independently at each occurrence selected from H, $C_3$-$C_6$-cycloalkyl, $C_1$-$C_6$-alkyl, $C(O)-C_1$-$C_6$-alkyl, $C(O)O-C_1$-$C_6$-alkyl, $C(O)NR^{10}R^{10}$, and $S(O)_2-C_1$-$C_6$-alkyl;
$R^{10}$, $R^{15}$ and $R^{19}$ are each independently at each occurrence selected from H, $C_1$-$C_6$-alkyl and $C_3$-$C_6$-cycloalkyl;
or where two $R^{10}$ groups are attached to the same nitrogen atom, the two $R^{10}$ groups together with the nitrogen atom to which they are attached may form a 4- to 7-membered heterocycloalkyl ring;

or $R^9$ and $R^{10}$ together with the nitrogen to which they are attached form a 4- to 7-membered heterocycloalkyl ring;

$R^{11}$ is independently at each occurrence selected from H, $C_1$-$C_6$-alkyl, $C_1$-$C_6$-haloalkyl, $C_3$-$C_6$-alkenyl, $C_3$-$C_6$-alkynyl, $C_0$-$C_3$-alkylene-$R^{11a}$; wherein $R^{11a}$ is independently selected from $C_3$-$C_6$-cycloalkyl and 3- to 6-membered heterocycloalkyl;

$R^{13}$ is independently selected from: H, $S(O)_2$—$C_1$-$C_6$-alkyl, $C_1$-$C_6$-alkyl, $C_3$-$C_7$-cycloalkyl, $C_1$-$C_4$-alkylene-$R^{13a}$, phenyl, 4- to 7-membered heterocycloalkyl, 5-, 6-, 9- or 10-membered heteroaryl, $C(S)$-$L^2$-$R^{14}$ and $C(O)$-$L^2$-$R^{14}$; wherein $R^{13a}$ is independently selected from: $C_3$-$C_6$-cycloalkyl, 4- to 7-membered heterocycloalkyl, phenyl, 5- or 6-membered heteroaryl, —O—$C_0$-$C_3$-alkylene-$C_3$-$C_6$-cycoalkyl, —O—$C_0$-$C_3$-alkylene-phenyl and —O—$C_1$-$C_6$-alkyl;

-$L^2$- is absent or is independently selected from —O—, —S—, and —$NR^{15}$—;

$R^{14}$ is independently selected from $C_1$-$C_8$-alkyl, $C_1$-$C_8$-haloalkyl, $C_3$-$C_8$-alkenyl, $C_3$-$C_8$-alkynyl, $C_0$-$C_3$-alkylene-$R^{16}$; and —$CR^{17}R^{17}L^3R^{18}$; -$L^3$- is independently selected from —O—, —S— and —$NR^{19}$—;

$R^{17}$ is independently at each occurrence selected from F, H and $C_1$-$C_4$-alkyl;

$R^{18}$ is independently selected from H, $C_1$-$C_8$-alkyl, $C_1$-$C_8$-haloalkyl, $C_3$-$C_8$-alkenyl, $C_3$-$C_8$-alkynyl and $C_0$-$C_3$-alkylene-$R^{20}$;

$R^{16}$ and $R^{20}$ are each independently at each occurrence selected from $C_3$-$C_6$-cycloalkyl, 3- to 6-membered heterocycloalkyl, 5- or 6-membered heteroaryl and phenyl;

y is an integer selected from 0, 1, 2, 3 and 4;

n is independently at each occurrence selected from 0, 1, 2 and 3; with the proviso that where -$L^1$- is —O—$(CR^4R^4)$—, $R^{13}$ is not selected from $C(S)$-$L^2$-$R^{14}$ and $C(O)$-$L^2$-$R^{14}$, and $R^7$ is independently at each occurrence selected from: halo, nitro, cyano, $NR^{10}R^{10}$, $NR^{10}S(O)_2R^{10}$, $OR^1$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl and —O—$C_1$-$C_6$-haloalkyl wherein where any $R^1$-$R^{20}$ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$, $C(O)R^a$, $CONR^aR^a$, $C_1$-$C_4$-alkyl, $C_2$-$C_4$-alkenyl, $C_2$-$C_4$-alkynyl, $C_3$-$C_6$-cycloalkyl and $C_1$-$C_4$-haloalkyl; wherein $R^a$ is independently at each occurrence selected from H, $C_1$-$C_4$-alkyl and $C_1$-$C_4$-haloalkyl; and $R^b$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

provided that the compound is not selected from:

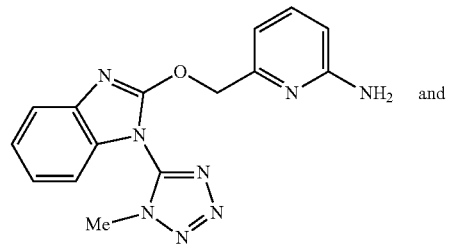 and

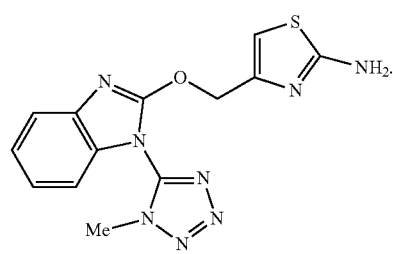

In an embodiment, the compound of formula (I) is a compound of formula (II):

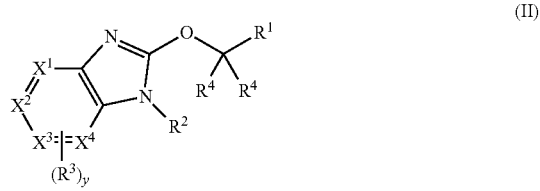

wherein $X^1$, $X^2$, $X^3$, $X^4$, $R^1$, $R^2$, $R^3$, $R^4$ and y are as described above for compounds of formula (I).

In an embodiment, the compound of formula (I) is a compound of formula (III):

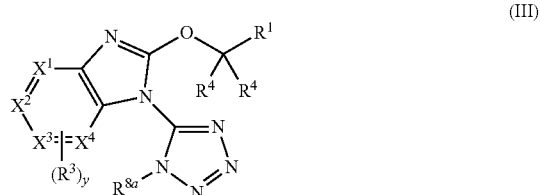

wherein $X^1$, $X^2$, $X^3$, $X^4$, $R^1$, $R^3$, $R^4$ and y are as described above for compounds of formula (I); and wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl. $R^{8a}$ may be selected from $C_1$-$C_4$-alkyl, $C_1$-$C_4$-haloalkyl and $C_3$-$C_6$-cycloalkyl.

In an embodiment, the compound of formula (I) is a compound of formula (IV):

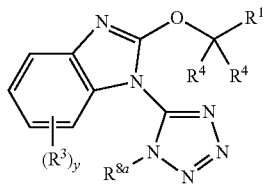

(IV)

wherein $R^1$, $R^3$, $R^4$ and y are as described above for compounds of formula (I); and wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl. $R^{8a}$ may be selected from $C_1$-$C_4$-alkyl, $C_1$-$C_4$-haloalkyl and $C_3$-$C_6$-cycloalkyl.

In an embodiment, the compound of formula (I) is a compound of formula (V):

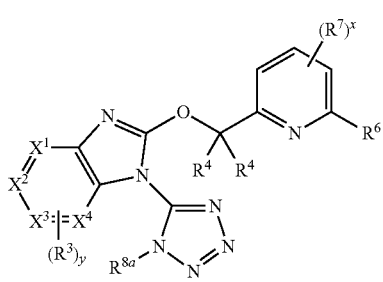

(V)

wherein $X^1$, $X^2$, $X^3$, $X^4$, $R^3$, $R^4$, $R^6$, $R^7$ and y are as described above for compounds of formula (I); wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and x is an integer independently selected from 0, 1, 2 and 3. $R^{8a}$ may be selected from $C_1$-$C_4$-alkyl, $C_1$-$C_4$-haloalkyl and $C_3$-$C_6$-cycloalkyl.

In an embodiment, the compound of formula I is a compound of formula (VI):

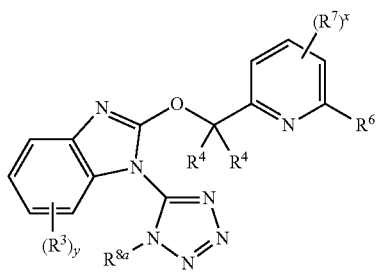

(VI)

wherein $R^3$, $R^4$, $R^6$, $R^7$ and y are as described above for compounds of formula (I); and wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and x is an integer independently selected from 0, 1, 2 and 3. $R^{8a}$ may be selected from $C_1$-$C_4$-alkyl, $C_1$-$C_4$-haloalkyl and $C_3$-$C_6$-cycloalkyl.

In an embodiment, the compound of formula (I) is a compound of formula (VII):

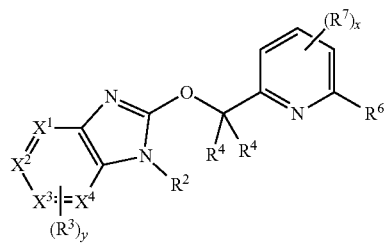

(VII)

wherein $X^1$, $X^2$, $X^3$, $X^4$, $R^2$, $R^3$, $R^4$, $R^6$, $R^7$ and y are as described above for compounds of formula (I); and wherein x is an integer independently selected from 0, 1, 2 and 3.

In an embodiment, the compound of formula (I) is a compound of formula (VIII):

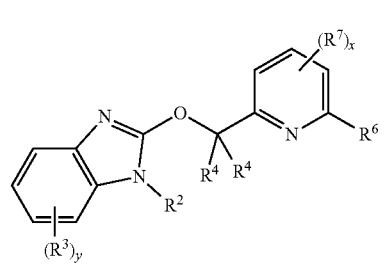

(VIII)

wherein $R^2$, $R^3$, $R^4$, $R^6$, $R^7$ and y are as described above for compounds of formula (I); and wherein x is an integer independently selected from 0, 1, 2 and 3.

In an embodiment, the compound of formula (I) is a compound of formula (IX):

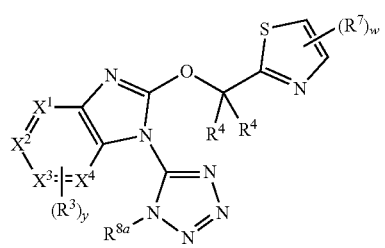

(IX)

wherein $X^1$, $X^2$, $X^3$, $X^4$, $R^3$, $R^4$, $R^7$ and y are as described above for compounds of formula (I); wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and w is an integer independently selected from 0, 1 and 2. $R^{8a}$ may be selected from $C_1$-$C_4$-alkyl, $C_1$-$C_4$-haloalkyl and $C_3$-$C_6$-cycloalkyl.

In an embodiment, the compound of formula I is a compound of formula (X):

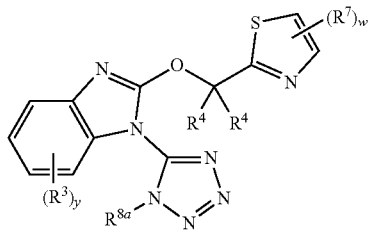

(X)

wherein $R^3$, $R^4$, $R^7$ and y are as described above for compounds of formula (I); and wherein $R^{8a}$ is independently selected from: $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and w is an integer independently selected from 0, 1 and 2. $R^{8a}$ may be selected from $C_1$-$C_4$-alkyl, $C_1$-$C_4$-haloalkyl and $C_3$-$C_6$-cycloalkyl.

In an embodiment, the compound of formula (I) is a compound of formula (XI):

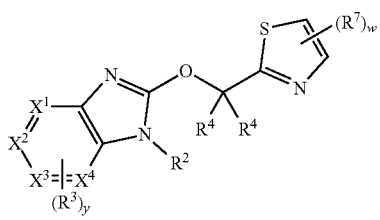

(XI)

wherein $X^1$, $X^2$, $X^3$, $X^4$, $R^2$, $R^3$, $R^4$, $R^7$ and y are as described above for compounds of formula (I); and wherein w is an integer independently selected from 0, 1 and 2.

In an embodiment, the compound of formula (I) is a compound of formula (XII):

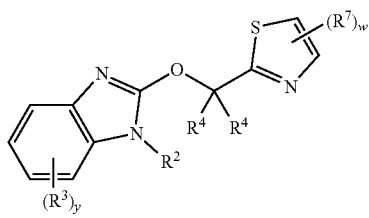

(XII)

wherein $R^2$, $R^3$, $R^4$, $R^7$ and y are as described above for compounds of formula (I); and wherein w is an integer independently selected from 0, 1 and 2.

The following embodiments apply to compounds of any of formulae (I)-(XII). These embodiments are independent and interchangeable. Any one embodiment may be combined with any other embodiment, where chemically allowed. In other words, any of the features described in the following embodiments may (where chemically allowable) be combined with the features described in one or more other embodiments. In particular, where a compound is exemplified or illustrated in this specification, any two or more of the embodiments listed below, expressed at any level of generality, which encompass that compound may be combined to provide a further embodiment which forms part of the present disclosure.

-$L^1$- may be —O—. -$L^1$- may be —$(CR^4R^4)$—O—. -$L^1$- may be —O—$(CR^4R^4)$—, e.g. —O—$CH_2$—.

$X^1$ may be nitrogen. $X^1$ may be carbon. $X^2$ may be nitrogen. $X^2$ may be carbon. $X^3$ may be nitrogen. $X^3$ may be carbon. $X^4$ may be nitrogen. $X^4$ may be carbon. It may be that no more than two of $X^1$, $X^2$, $X^3$ and $X^4$ are nitrogen. It may be that no more than one of $X^1$, $X^2$, $X^3$ and $X^4$ are nitrogen. It may be that a single one of $X^1$, $X^2$, $X^3$ and $X^4$ is nitrogen. It may be that each of $X^1$, $X^2$, $X^3$ and $X^4$ are carbon.

It may be that $R^1$ is a heteroaryl group independently selected from thiazole and 6-membered heteroaryl group, wherein said heteroaryl group is optionally substituted with a single $R^6$ group and/or from 1 to 4 $R^7$ groups; wherein $R^1$ has a nitrogen atom in the ring, said nitrogen atom being directly attached to the carbon atom in the ring by which $R^1$ is attached to the rest of the molecule (i.e. to $L^1$).

$R^1$ may be a 6-membered heteroaryl group. $R^1$ may be a 6-membered heteroaryl group in which a nitrogen atom in the ring is directly attached to the carbon atom in the ring by which $R^1$ is attached to the rest of the molecule (i.e. to $L^1$).

$R^1$ may be a 6-membered heteroaryl group comprising at least 2 nitrogen atoms in the ring. $R^1$ may be a 6-membered heteroaryl group comprising at least 2 nitrogen atoms in the ring, wherein at least one nitrogen atom in the ring is directly attached to the carbon atom in the ring by which $R^1$ is attached to the rest of the molecule (i.e. to $L^1$). $R^1$ may be a pyridazine, e.g. a 3-pyridazine. $R^1$ may be a pyrazine, e.g. a 2-pyrazine. $R^1$ may be a pyrimidine, e.g. a 2-pyrimidine.

$R^1$ may be a 2-pyridine.

$R^1$ may have the structure:

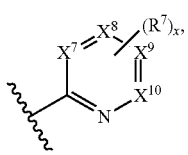

wherein $X^7$, $X^8$ and $X^9$ are each selected from carbon and nitrogen; $X^{10}$ is independently selected from nitrogen and $CR^6$; providing no more than one of $X^7$, $X^8$, $X^9$ and $X^{10}$ are nitrogen; and wherein x is an integer selected from 0, 1, 2 and 3.

It may be that $X^7$ is nitrogen, $X^8$ and $X^9$ are both carbon and $X^{10}$ is $CR^6$. It may be that $X^7$ and $X^8$ are both carbon, $X^9$ is nitrogen and $X^{10}$ is $CR^6$. It may be that $X^7$ and $X^9$ are both carbon, $X^8$ is nitrogen and $X^{10}$ is $CR^6$. It may be that $X^7$, $X^8$ and $X^9$ are each carbon and $X^{10}$ is nitrogen. It may be that $X^7$, $X^8$ and $X^9$ are each carbon and $X^{10}$ is $CR^6$.

$R^1$ may have the structure:

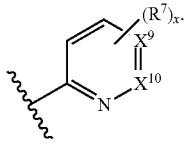

R[1] may have the structure:

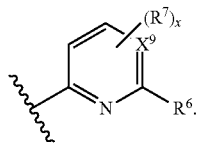

In certain embodiments, R[1] has the structure:

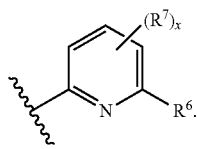

It may be that R[6] is H. Thus, R[1] may have the structure:

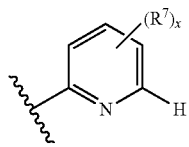

In certain embodiments, R[1] has the structure:

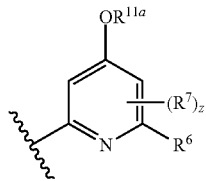

wherein R[11a] is independently selected from H, $C_1$-$C_6$-alkyl, $C_1$-$C_6$-haloalkyl, and $C_3$-$C_6$-cycloalkyl; and z is an integer selected from 0, 1 and 2. It may be that R[11a] is independently selected from $C_1$-$C_6$-alkyl, $C_1$-$C_6$-haloalkyl, and $C_3$-$C_6$-cycloalkyl. It may be that R[11a] is independently selected from $C_1$-$C_6$-alkyl and $C_1$-$C_6$-haloalkyl. It may be that R[6] is H.

It may be that R[1] has the structure:

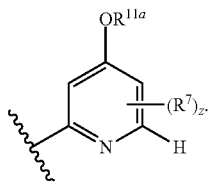

In illustrative examples, R[1] may be selected from:

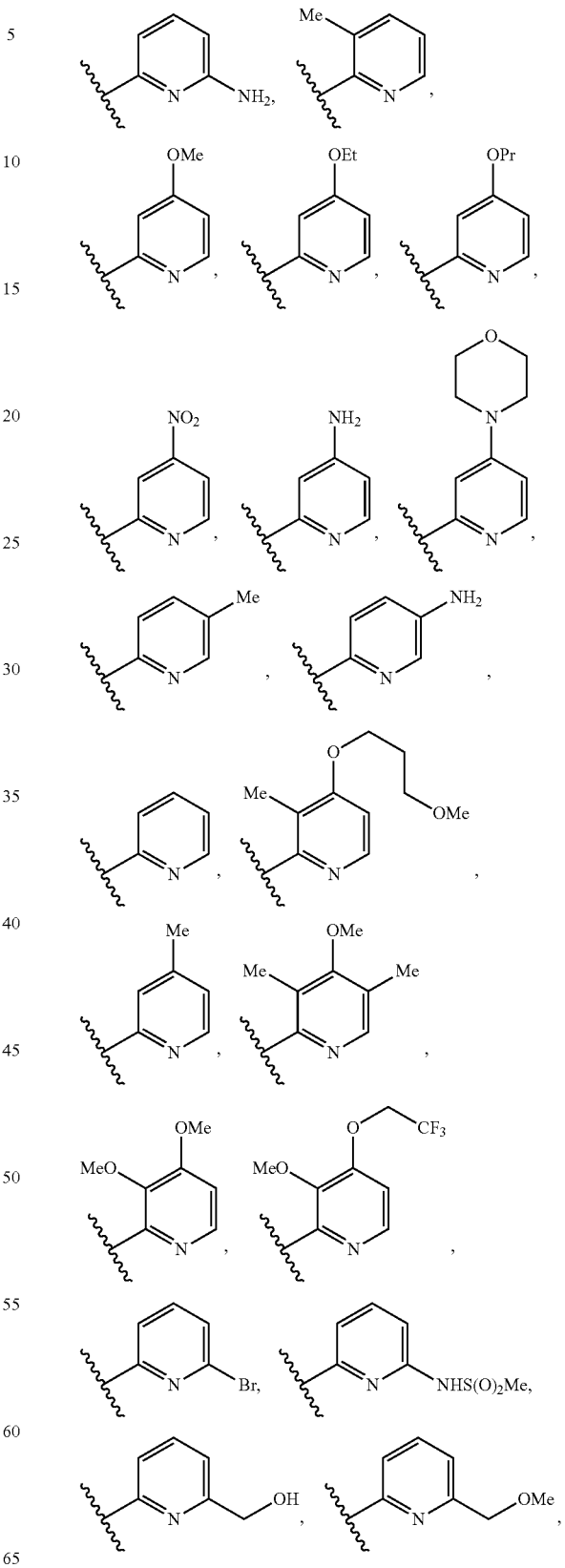

-continued

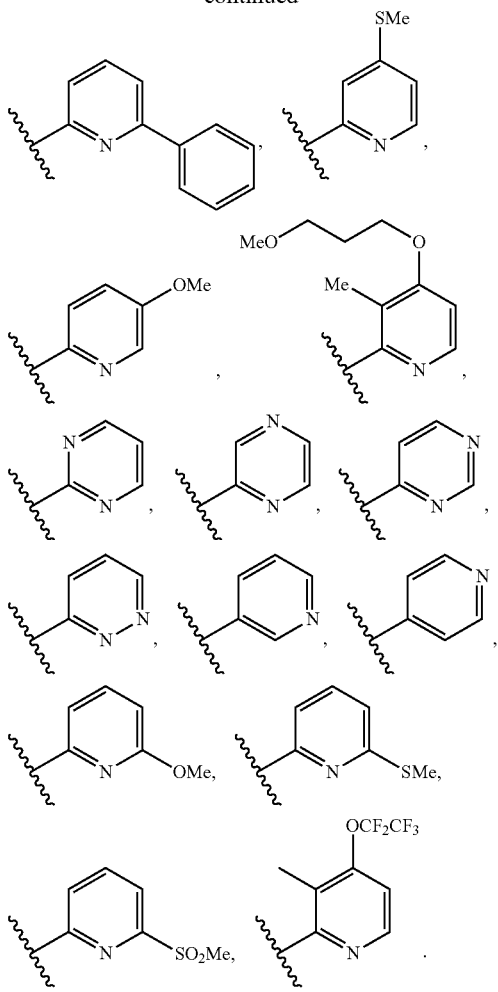

In certain embodiments, $R^1$ has the structure:

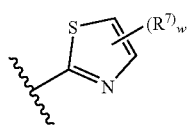

wherein w is an integer selected from 0, 1 and 2.

In certain embodiments, $R^1$ has the structure:

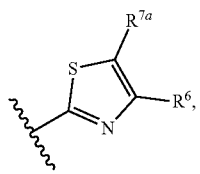

wherein $R^{7a}$ is independently selected from H, halo, nitro, cyano, $NR^{10}R^{10}$, $OR^{11}$, $SR^{10}$, $S(O)R^{10}$, $S(O)_2R^{10}$, $OS(O)_2OR^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

In certain embodiments, $R^1$ has the structure:

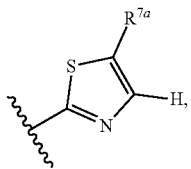

wherein $R^{7a}$ is independently selected from H, halo, nitro, cyano, $NR^{10}R^{10}$, $OR^{11}$, $SR^{10}$, $S(O)R^{10}$, $S(O)_2R^{10}$, $OS(O)_2OR^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

In illustrative examples, $R^1$ may be:

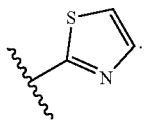 [SMILES: *c1nccs1]

$R^7$ may be independently at each occurrence selected from halo, nitro, cyano, $NR^{10}R^{10}$, $OR^{11}$, $SR^{10}$, $S(O)R^{10}$, $S(O)_2R^{10}$, $OS(O)_2OR^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl. $R^7$ may be independently at each occurrence selected from halo, $C_1$-$C_4$-alkyl, $C_1$-$C_4$-haloalkyl, S—$C_1$-$C_4$-alkyl, O—$C_1$-$C_4$-alkyl and O—$C_1$-$C_4$-haloalkyl.

$R^{7a}$ may be independently at each occurrence selected from halo, $C_1$-$C_4$-alkyl, $C_1$-$C_4$-haloalkyl, S—$C_1$-$C_4$-alkyl, O—$C_1$-$C_4$-alkyl and O—$C_1$-$C_4$-haloalkyl. $R^{7a}$ may be independently at each occurrence selected from halo, $C_1$-$C_4$-alkyl and $C_1$-$C_4$-haloalkyl.

x may be an integer from 0 to 1. x may be an integer from 1 to 2. x may be 1. x may be 0.

z may be an integer from 1 to 2. z may be 1. z may be 0.

w may be 1. w may be 0.

In certain embodiments, $R^1$ is 9-, or 10-membered heteroaryl. In illustrative examples, $R^1$ may be selected from:

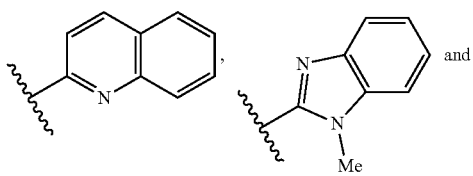

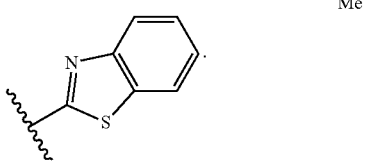

$R^6$ may be H.

$R^6$ may be $NHR^{13}$.

$R^{13}$ may be independently selected from: H and $C_1$-$C_6$-alkyl.

$R^{13}$ may be unsubstituted. $R^{13}$ may be selected from groups that comprise only carbon and hydrogen.

$R^{13}$ may be independently selected from: $C_1$-$C_6$-alkyl, $C_3$-$C_6$-cycloalkyl, and $C_1$-$C_4$-alkylene-$R^{13a}$. $R^{13a}$ may be independently selected from: $C_3$-$C_6$-cycloalkyl, phenyl and 5- or 6-membered heteroaryl. $R^{13a}$ may be independently selected from: $C_3$-$C_6$-cycloalkyl and phenyl. $R^{13a}$ may be 5- or 6-membered heteroaryl, e.g. 5- or 6-membered heteroaryl group having at least one nitrogen atom in the ring.

Illustrative $R^6$ groups include:

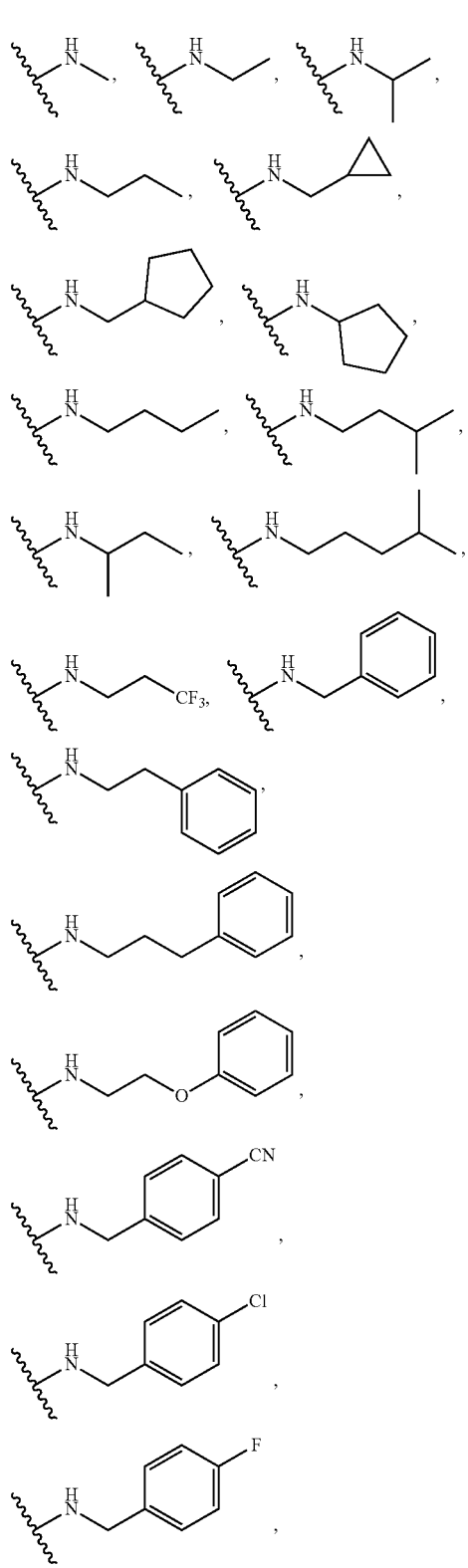

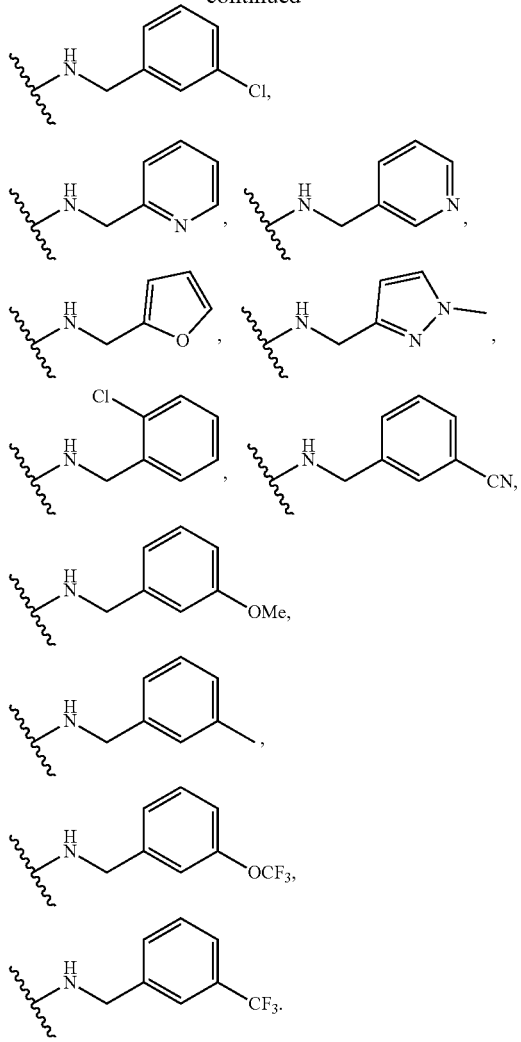

$R^{13}$ may be independently selected from phenyl, 4- to 7-membered heterocycloalkyl and 5-, 6-, 9- or 10-membered heteroaryl. $R^{13}$ may be independently selected from 4- to 7-membered heterocycloalkyl and 5-, 6-, 9- or 10-membered heteroaryl. $R^{13}$ may be independently selected from 4- to 7-membered heterocycloalkyl and 5- or 6-membered heteroaryl.

Preferably, $R^{13}$ is selected from C(S)-$L^2$-$R^{14}$ and C(O)-$L^2$-$R^{14}$. $R^{13}$ may be C(O)-$L^2$-$R^{14}$.

-$L^2$- may be absent. In these embodiments, $R^{14}$ may be independently selected from: $C_1$-$C_8$-alkyl, $C_2$-$C_8$-alkenyl, $C_2$-$C_8$-alkynyl and $C_0$-$C_3$-alkylene-$R^{16}$. $R^{16}$ may be selected from $C_3$-$C_6$-cycloalkyl and phenyl. $R^{16}$ may be phenyl. $R^{16}$ may be $C_3$-$C_6$-cycloalkyl. $R^{14}$ may be independently selected from: $C_1$-$C_8$-alkyl and $C_0$-$C_3$-alkylene-$R^{16}$, where $R^{16}$ is selected from phenyl and $C_3$-$C_6$-cycloalkyl. $R^{14}$ may be independently selected from: $C_1$-$C_8$-alkyl and $C_0$-$C_3$-alkylene-$R^{16}$, where $R^{16}$ is $C_3$-$C_6$-cycloalkyl. Said $R^{14}$ and $R^{16}$ groups may be unsubstituted.

-$L^2$- may be absent. In these embodiments, $R^{14}$ may be independently selected from: 3- to 6-membered heterocycloalkyl, 5- or 6-membered heteroaryl and —C$R^{17}R^{17}L^3R^{18}$. $R^{14}$ may be independently selected from: 3- to 6-membered heterocycloalkyl, 5- or 6-membered heteroaryl. $R^{14}$ may be C$R^{17}R^{17}L^3R^{18}$.

$R^{17}$ is preferably at all occurrences independently selected from F, H and Me. $R^{17}$ may at all occurrences be selected from F and H. $R^{17}$ may at all occurrences be H. $R^{17}$ may at all occurrences be F.

-$L^3$- may be —$NR^{19}$—, e.g. NH. -$L^3$- may be —S—. -$L^3$- may be —O—.

$R^{14}$ may be $CR^{17}R^{17}OR^{18}$ or $CR^{17}R^{17}SR^{18}$, where $R^{18}$ is independently selected from $C_1$-$C_8$-alkyl, $C_1$-$C_8$-haloalkyl, $C_3$-$C_8$-alkenyl, $C_3$-$C_8$-alkynyl and $C_0$-$C_3$-alkylene-$R^{20}$ wherein $R^{20}$ is independently at each occurrence selected from $C_3$-$C_6$-cycloalkyl, 3- to 6-membered heterocycloalkyl, 5- or 6-membered heteroaryl and phenyl. $R^{18}$ may be independently selected from: $C_1$-$C_8$-alkyl, $C_3$-$C_8$-alkenyl, $C_3$-$C_8$-alkynyl and $C_0$-$C_3$-alkylene-$R^{20}$. $R^{20}$ may be selected from $C_3$-$C_6$-cycloalkyl and phenyl. $R^{20}$ may be phenyl. $R^{20}$ may be $C_3$-$C_6$-cycloalkyl. $R^{18}$ may be independently selected from: $C_1$-$C_8$-alkyl and $C_0$-$C_3$-alkylene-$R^{20}$, where $R^{20}$ is selected from phenyl and $C_3$-$C_6$-cycloalkyl. Said $R^{18}$ and $R^{20}$ groups may be unsubstituted.

-$L^2$- may be independently selected from: —O—, —S— and —$NR^{15}$—. -$L^2$- may be —O—. In these embodiments, $R^{14}$ may be independently selected from: $C_1$-$C_8$-alkyl, $C_3$-$C_8$-alkenyl, $C_3$-$C_8$-alkynyl and $C_0$-$C_3$-alkylene-$R^{16}$. $R^{16}$ may be selected from $C_3$-$C_6$-cycloalkyl and phenyl. $R^{16}$ may be phenyl. $R^{16}$ may be $C_3$-$C_6$-cycloalkyl. $R^{14}$ may be independently selected from: $C_1$-$C_8$-alkyl and $C_0$-$C_3$-alkylene-$R^{16}$, where $R^{16}$ is selected from phenyl and $C_3$-$C_6$-cycloalkyl. $R^{14}$ may be independently selected from: $C_1$-$C_8$-alkyl and $C_0$-$C_3$-alkylene-$R^{16}$, where $R^{16}$ is $C_3$-$C_6$-cycloalkyl. Said $R^{14}$ and $R^{16}$ groups may be unsubstituted. $R^{14}$ may be $C_1$-$C_8$-alkyl. $R^{14}$ may be $C_3$-$C_8$-alkyl.

It may be that $R^4$ is independently at each occurrence selected from H, F, $C_1$-$C_4$-alkyl and $C_1$-$C_4$-haloalkyl. It may be that $R^4$ is independently at each occurrence selected from H, F, Me, $CF_3$ and Et. It may be that $R^4$ is each independently at each occurrence selected from H and Me. It may be that $R^4$ is at each occurrence H.

It may be that when $R^{14}$ is —$CR^{17}R^{17}L^3R^{18}$, -$L^2$- is absent.

$R^2$ may be a 5- or 6-membered heteroaryl group having 1, 2, 3 or 4 nitrogen atoms in the ring. $R^2$ may be a 5-membered heteroaryl group having 1, 2, 3 or 4 nitrogen atoms in the ring. $R^2$ may be a 6-membered heteroaryl group having 1 or 2 nitrogen atoms in the ring.

$R^2$ may be substituted at a position adjacent to the point of connection of $R^2$ to the rest of the molecule with an $R^{8b}$ group, wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl. $R^2$ may be a 5- or 6-membered heteroaryl group having 1, 2, 3 or 4 nitrogen atoms in the ring, said heteroaryl group being substituted at a position adjacent to the point of connection of $R^2$ to the rest of the molecule with an $R^{8b}$ group. $R^2$ may be a 5-membered heteroaryl group having 1, 2, 3 or 4 nitrogen atoms in the ring, said heteroaryl group being substituted at a position adjacent to the point of connection of $R^2$ to the rest of the molecule with an $R^{8b}$ group. $R^2$ may be a 6-membered heteroaryl group having 1 or 2 nitrogen atoms in the ring, said heteroaryl group being substituted at a position ortho to the point of connection of $R^2$ to the rest of the molecule with an $R^{8b}$ group.

$R^2$ may be a tetrazole ring. Said tetrazole ring is substituted with a single $R^{8a}$ group; wherein $R^{8a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

Said tetrazole will typically be attached to the rest of the molecule via the carbon atom of the tetrazole ring. $R^{8a}$ may be attached to a nitrogen atom neighbouring said carbon atom. Thus, $R^2$ may be:

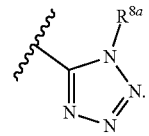

$R^{8a}$ is preferably selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl. $R^{8a}$ may be selected from $C_1$-$C_4$-alkyl, $C_1$-$C_4$-haloalkyl and $C_3$-$C_6$-cycloalkyl. $R^{8a}$ may be $C_1$-$C_4$-alkyl, e.g. methyl.

Thus, $R^2$ may be:

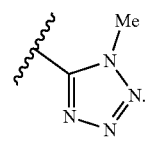 [SMILES: *c1nnnn1C]

$R^2$ may be selected from isoxazole, pyrazole or isothiazole. Thus, $R^2$ may be:

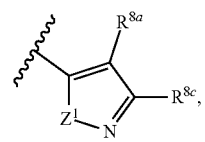

where $Z^1$ is selected from O, S and $NR^a$; wherein $R^{8a}$ is independently selected from: H, $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and wherein $R^{8c}$ is selected from H and $R^8$. $R^2$ may be:

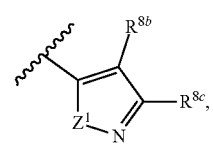

wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and wherein $R^{8c}$ is selected from H and $R^8$. $Z^1$ may be S. $Z^1$ may be O. $Z^1$ may be $NR^{8a}$.

Alternatively, $R^2$ may be:

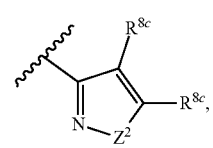

where $Z^2$ is selected from O, S and $NR^{8a}$; wherein $R^{8a}$ is independently selected from: H, $C_1$-$C_4$-alkyl, $C_3$-$C_4$-alkenyl, $C_3$-$C_4$-alkynyl, phenyl, $C_3$-$C_8$-cycloalkyl, 3- to 6-membered heterocycloalkyl, 5- or 6-membered heteroaryl and $C_1$-$C_4$-haloalkyl; and wherein $R^{8c}$ is selected from H and $R^8$. $R^2$ may be:

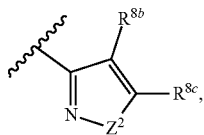

wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_8$-cycloalkyl, 3- to 6-membered heterocycloalkyl, 5- or 6-membered heteroaryl and $C_1$-$C_4$-haloalkyl; and wherein $R^{8c}$ is selected from H and $R^8$. $Z^2$ may be S. $Z^2$ may be O. $Z^2$ may be $NR^{8a}$.

Illustrative examples of $R^2$ include:

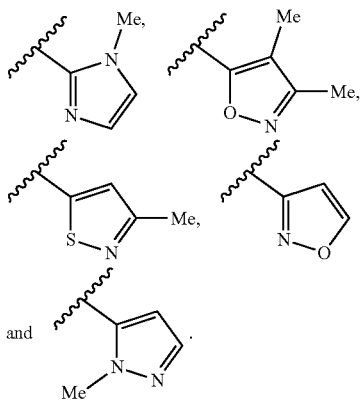

$R^2$ may be a 6-membered heteroaromatic ring. $R^2$ may be a pyridine. $R^2$ may be a 2-pyridine. $R^2$ may be a pyrazine. $R^2$ may be a pyridazine.

$R^2$ may be:

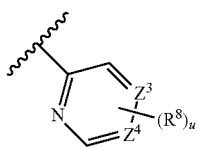

wherein $Z^3$ and $Z^4$ are each independently selected from nitrogen or carbon; and u is an integer from 0 to 4. For the absence of doubt, where $Z^3$ and/or $Z^4$ is carbon, said carbon may be substituted with an $R^8$ group.

$R^2$ may be

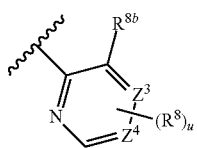

wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl; and wherein u is an integer from 0 to 4.

$Z^3$ may be carbon. $Z^3$ may be nitrogen. $Z^4$ may be carbon. $Z^4$ may be nitrogen. It may be that a single one of $Z^3$ and $Z^4$ is nitrogen. It may be that $Z^3$ and $Z^4$ are each carbon. It may be that $Z^3$ is carbon and $Z^4$ is nitrogen. It may be that $Z^4$ is carbon and $Z^3$ is nitrogen.

Illustrative examples of $R^2$ include:

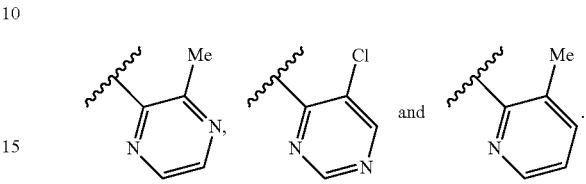

$R^{8a}$ may be independently selected from: H, $C_1$-$C_4$-alkyl, $C_3$-$C_4$-alkenyl and $C_3$-$C_4$-alkynyl. $R^{8a}$ may be independently selected from: H and $C_1$-$C_4$-alkyl. $R^{8a}$ may be independently selected from: $C_1$-$C_4$-alkyl, $C_3$-$C_4$-alkenyl and $C_3$-$C_4$-alkynyl. $R^{8a}$ may be H. $R^{8a}$ may be $C_1$-$C_4$-alkyl, e.g. methyl.

$R^{8b}$ may be selected from $C_1$-$C_4$-alkyl, $C_1$-$C_4$-haloalkyl and $C_3$-$C_5$-cycloalkyl. $R^{8b}$ may be $C_1$-$C_4$-alkyl, e.g. methyl.

$R^{8c}$ may be at all occurrences H.

u may be 1 or 2. u may be 0.

$R^8$ is independently at each occurrence selected from: halo, nitro, cyano, $NR^9R^{10}$, $OR^{11}$, $SR^{10}$, $S(O)R^{10}$, $S(O)_2R^{10}$, $S(O)_2NR^{10}R^{10}$, $OS(O)_2OR^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, phenyl, $C_3$-$C_5$-cycloalkyl, 3- to 6-membered heterocycloalkyl, 5- or 6-membered heteroaryl, $C_1$-$C_4$-haloalkyl and O—$C_1$-$C_4$-haloalkyl. $R^8$ may be independently at each occurrence selected from halo, nitro, cyano, $NR^9R^{10}$, $OR^{11}$, $SR^{10}$, $S(O)R^{10}$, $S(O)_2R^{10}$, $S(O)_2NR^{10}R^{10}$, $OS(O)_2OR^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, $C_1$-$C_4$-haloalkyl and O—$C_1$-$C_4$-haloalkyl. $R^8$ may be independently at each occurrence selected from halo, cyano, $C_1$-$C_4$-alkyl and $C_1$-$C_4$-haloalkyl. $R^8$ may be independently at each occurrence selected from: halo, cyano, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

y may be 0. Alternatively, y may be 1 or 2. $R^3$ may be independently at each occurrence selected from halo, cyano, nitro, $C_1$-$C_4$-alkyl and $C_1$-$C_4$-haloalkyl, O—$C_1$-$C_4$-alkyl and O—$C_1$-$C_4$-haloalkyl.

$X^1$ may be $CR^{3a}$, wherein $R^{3a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl.

Thus,

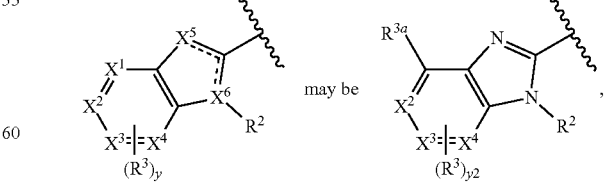

wherein $R^{3a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl; and y2 is an integer independently selected from 0, 1, 2 and 3.

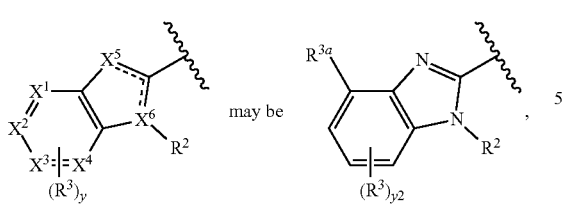

wherein $R^{3a}$ is selected from halo, cyano, nitro, $C_1$-$C_4$-alkyl and $C_1$-$C_4$-haloalkyl, O—$C_1$-$C_4$-alkyl and O—$C_1$-$C_4$-haloalkyl; and y2 is an integer independently selected from 0, 1, 2 and 3.

$R^{3a}$ may be selected from fluoro, chloro, bromo, $C_1$-$C_4$-alkyl, $C_1$-$C_4$-haloalkyl, phenyl, 0-$C_1$-$C_4$-alkyl and O—$C_1$-$C_4$-haloalkyl. $R^{3a}$ may be selected from fluoro, chloro, bromo, $C_1$-$C_4$-alkyl, $C_1$-$C_4$-haloalkyl, O—$C_1$-$C_4$-alkyl and O—$C_1$-$C_4$-haloalkyl. $R^{3a}$ may be selected from chloro, bromo, $C_1$-$C_4$-alkyl, $C_1$-$C_4$-haloalkyl, O—$C_1$-$C_4$-alkyl and O—$C_1$-$C_4$-haloalkyl. $R^{3a}$ may be chloro or bromo. $R^{3a}$ may be chloro. $R^{3a}$ may be bromo. $R^{3a}$ may be fluoro. $R^{11}$ may be independently at each occurrence selected from H, $C_1$-$C_6$-alkyl, $C_1$-$C_6$-haloalkyl, $C_3$-$C_6$-alkenyl, $C_3$-$C_6$-alkynyl. $R^{11}$ may be independently at each occurrence selected from H, $C_1$-$C_6$-alkyl and $C_1$-$C_6$-haloalkyl. $R^{11}$ may be independently at each occurrence selected from H and $C_1$-$C_6$-alkyl.

The compound of formula (I) may be a compound selected from:

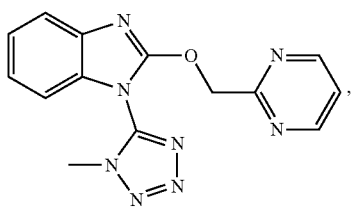

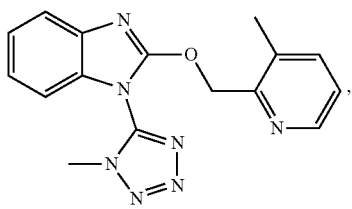

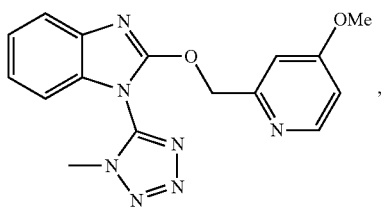

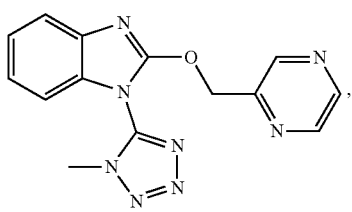

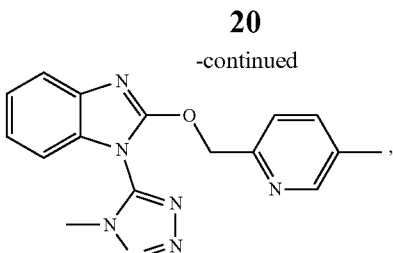

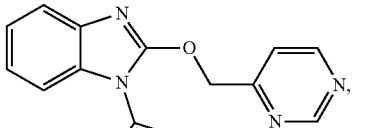

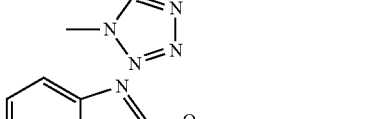

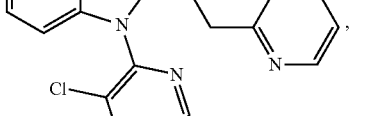

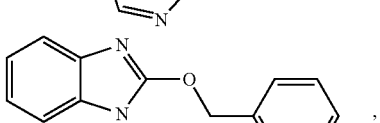

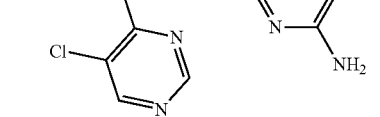

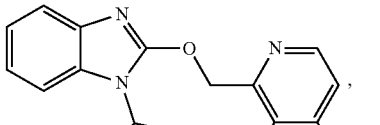

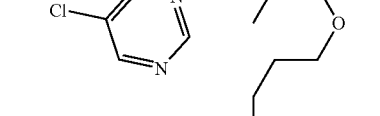

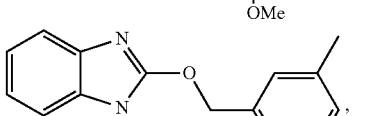

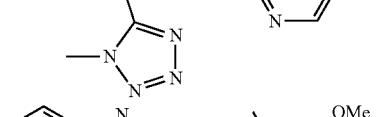

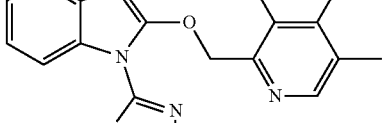

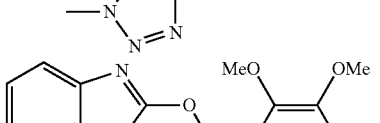

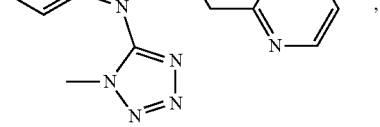

-continued
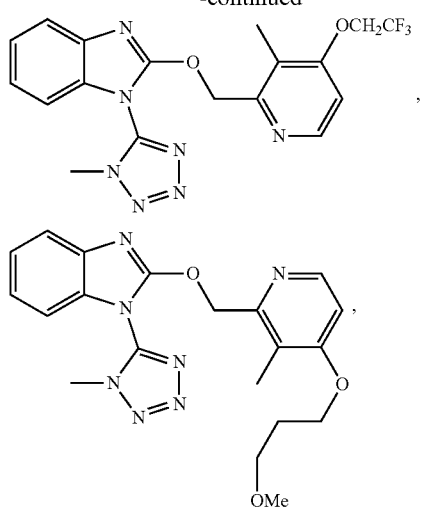
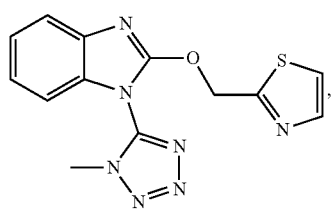
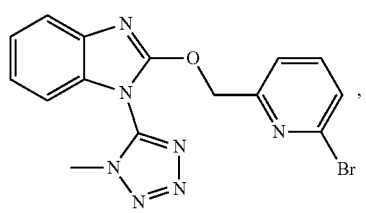
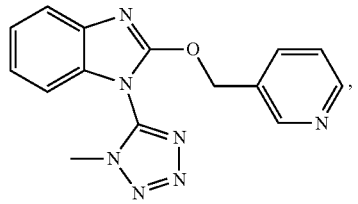
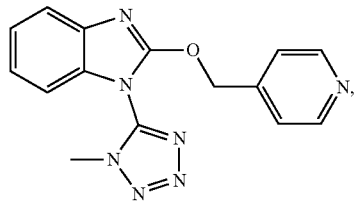
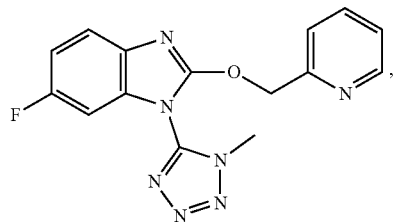
-continued
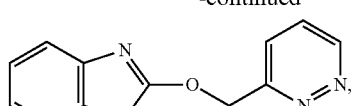
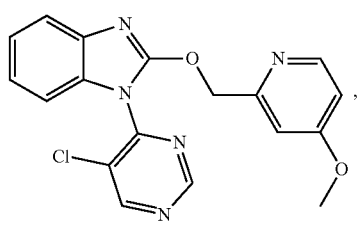
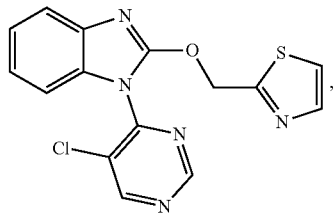
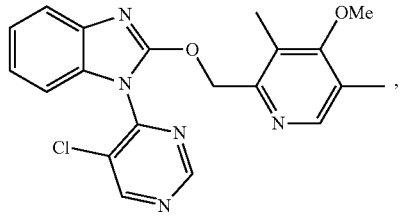
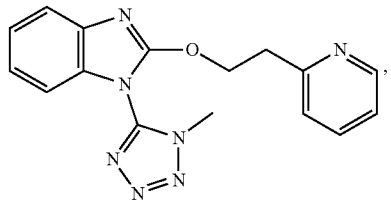
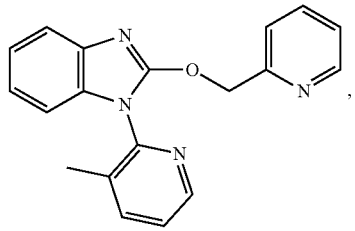
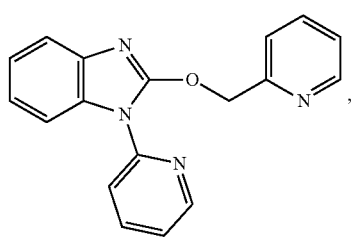

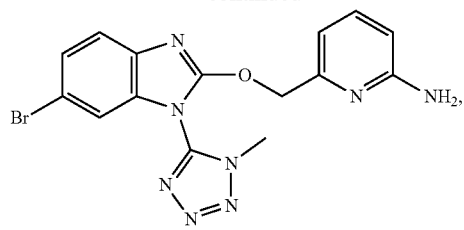
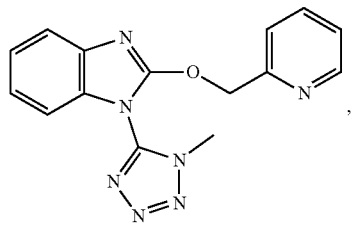
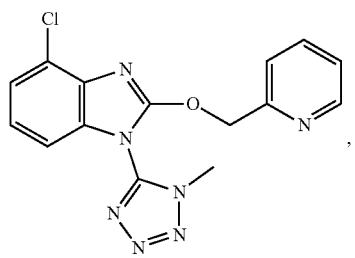
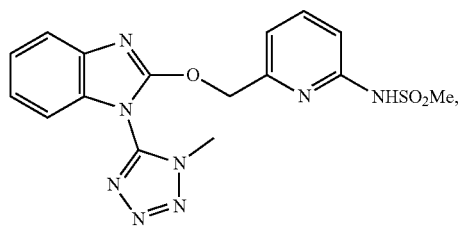
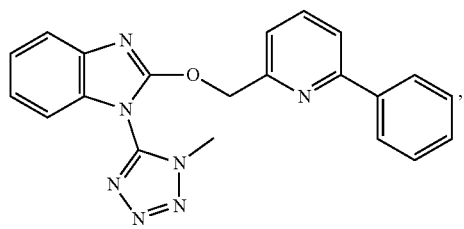
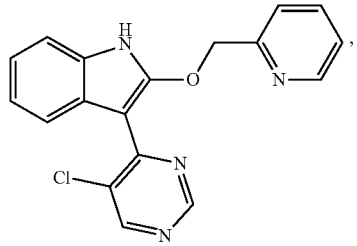
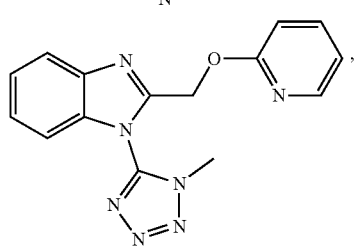
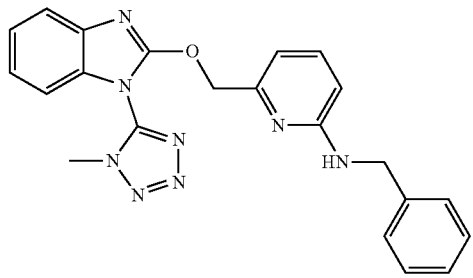
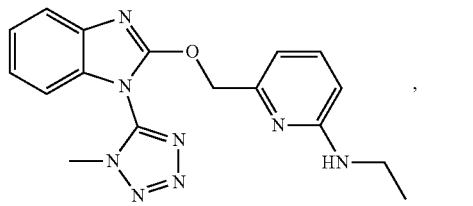
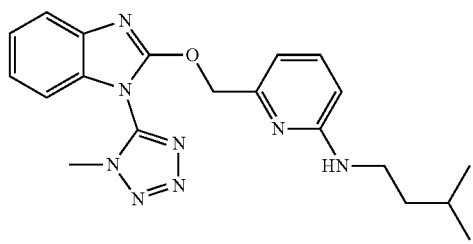
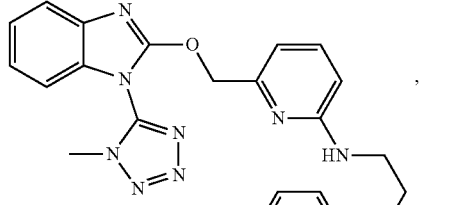
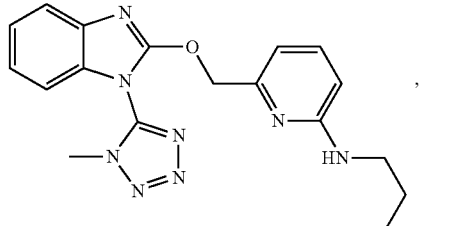
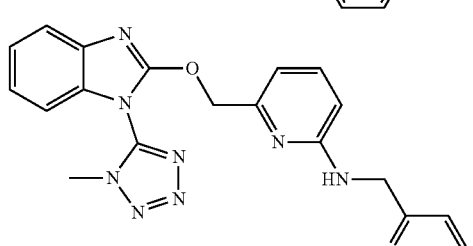

25
-continued
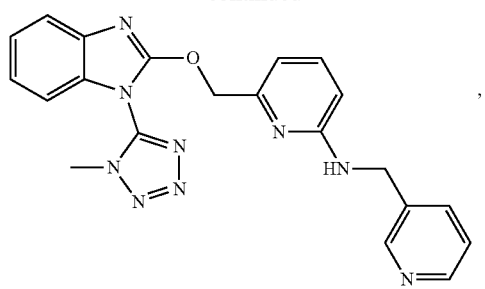
,
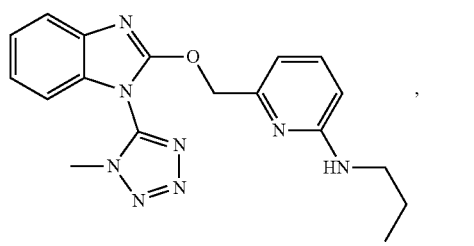
,
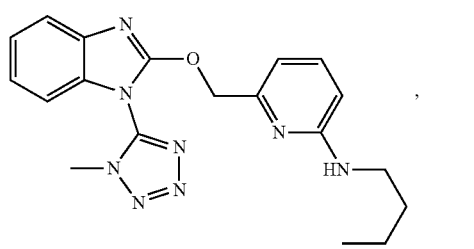
,
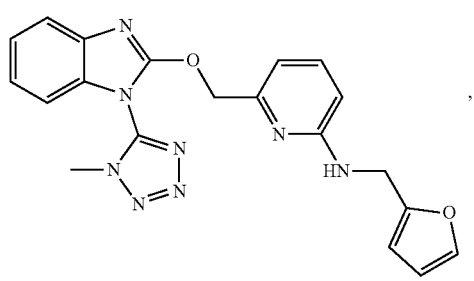
,
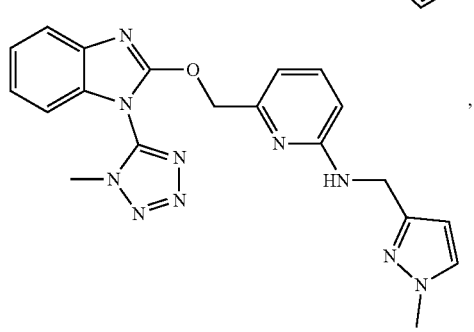
,
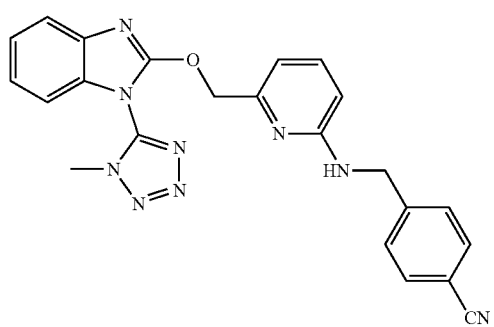
,
26
-continued
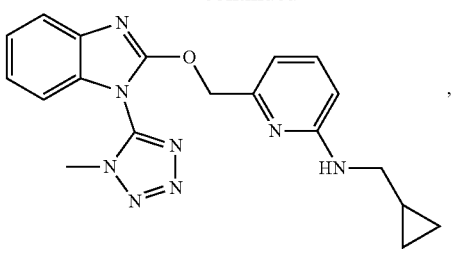
,
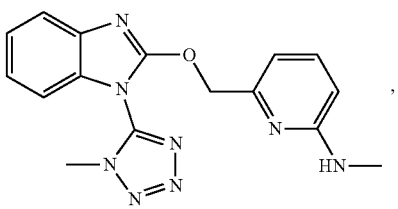
,
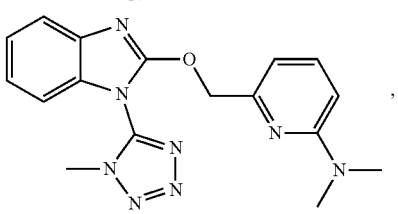
,
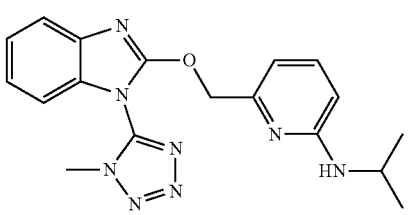
,
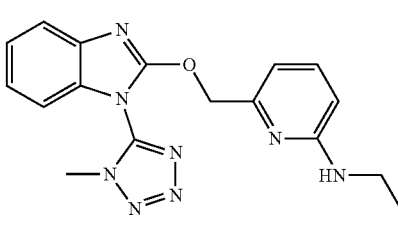
,
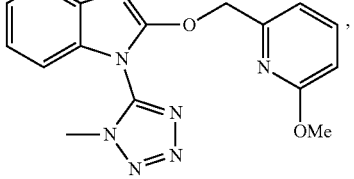
,
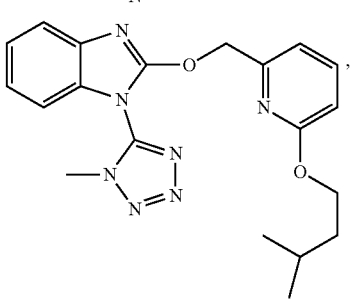
,

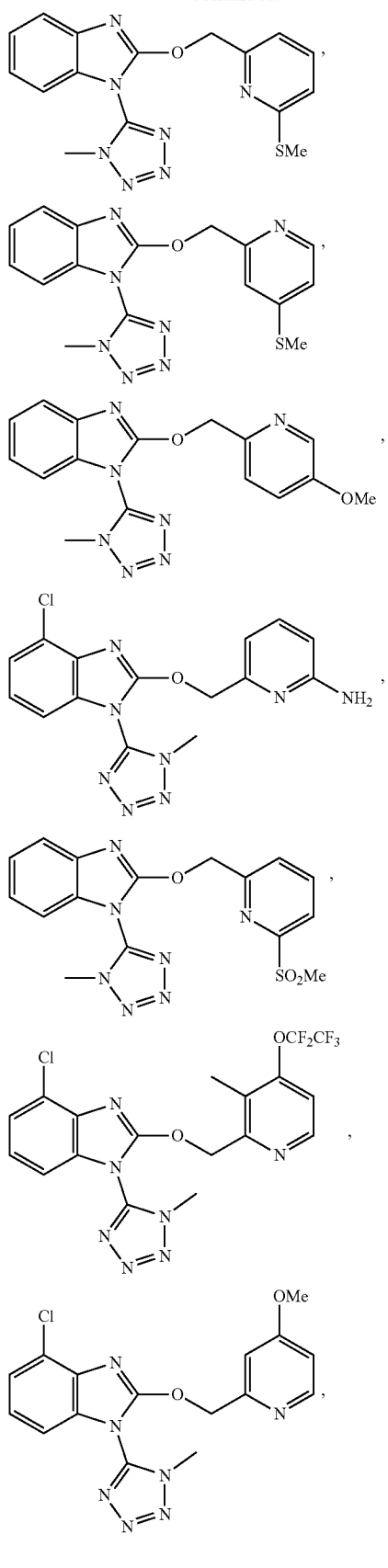
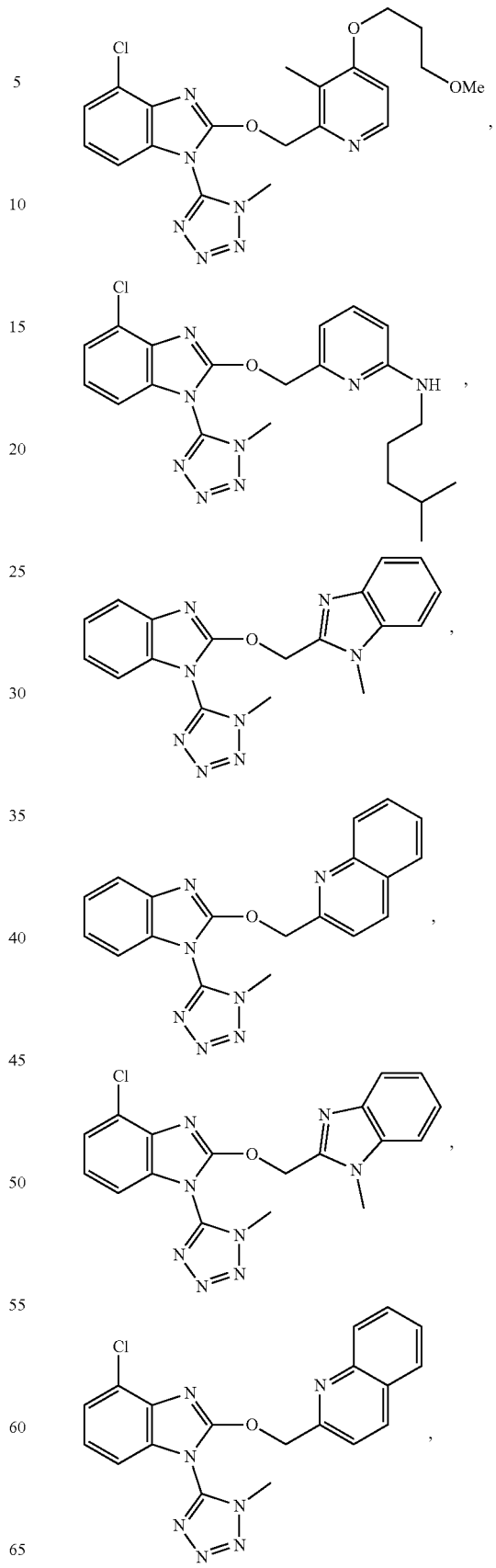

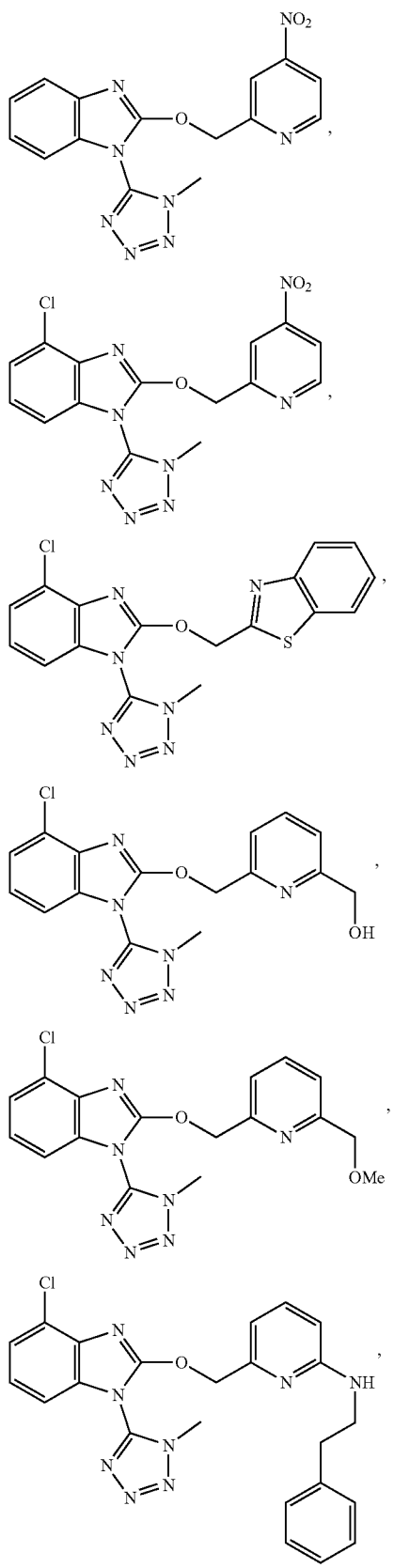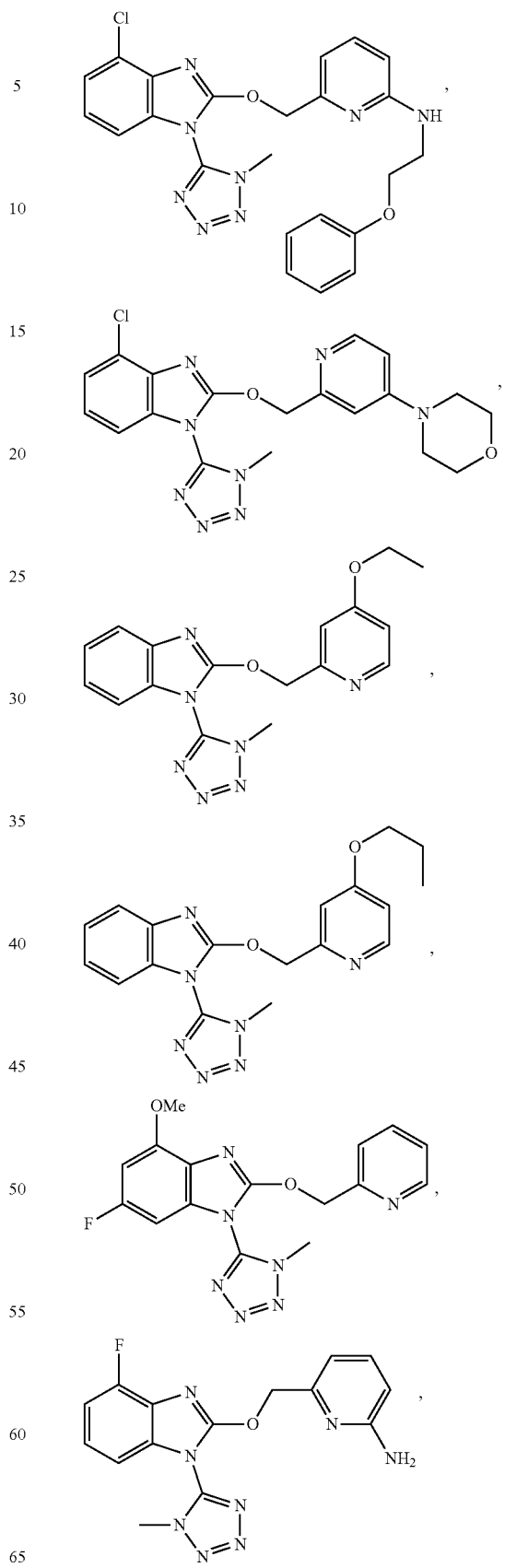

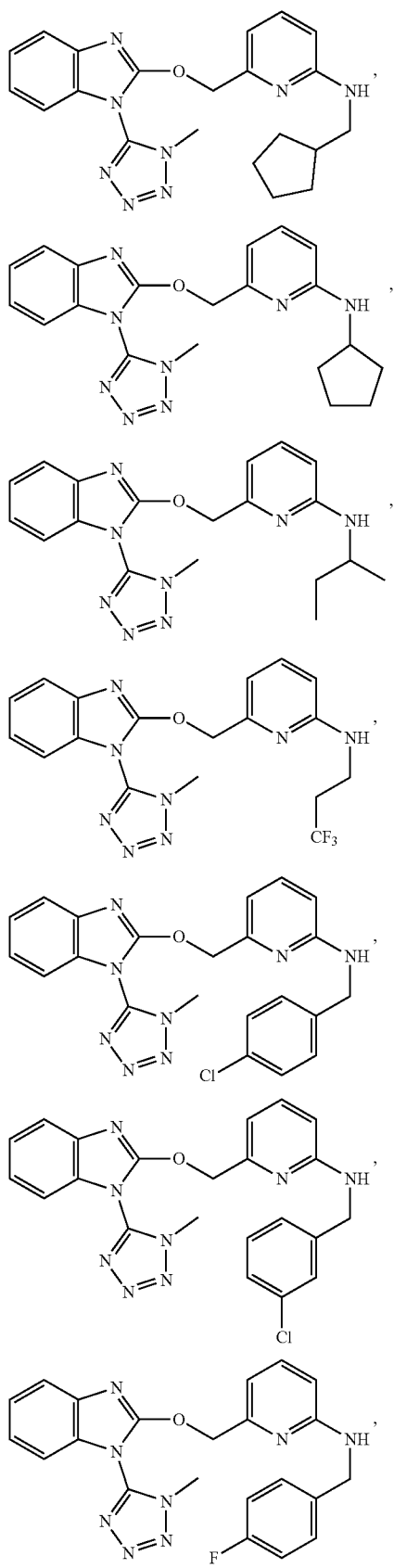
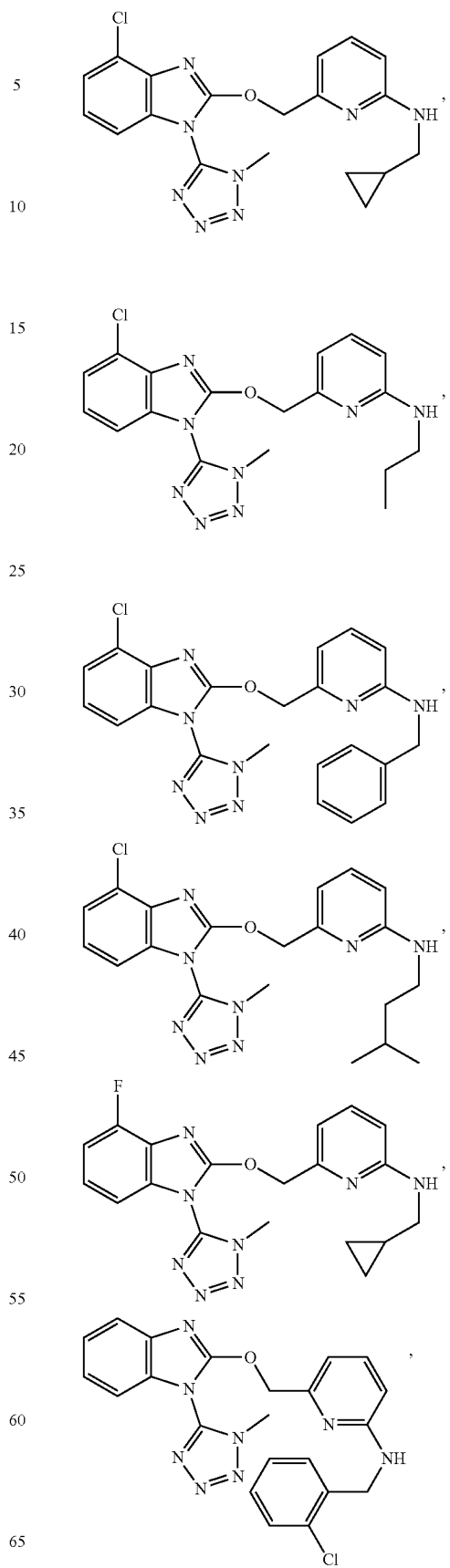

-continued
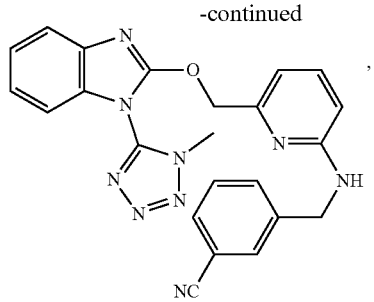
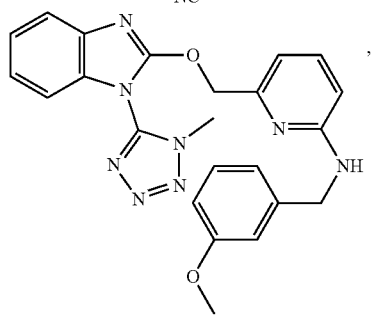
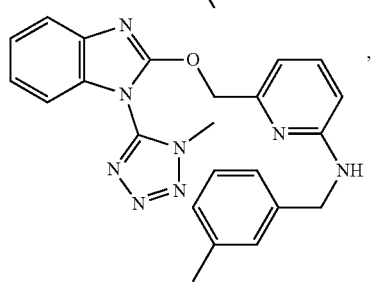
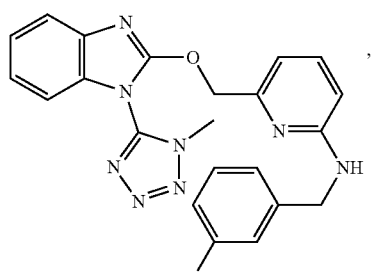
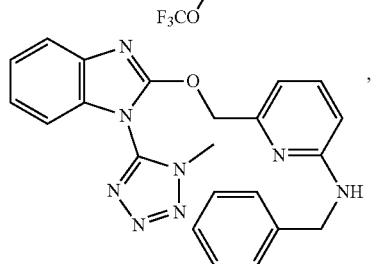
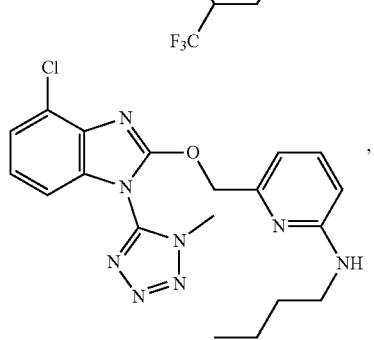
-continued
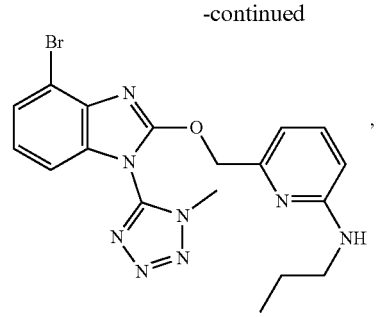
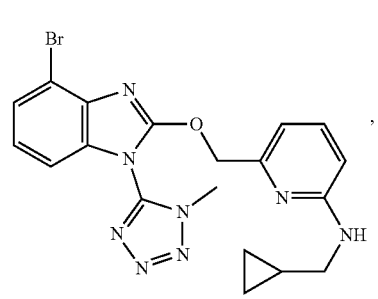
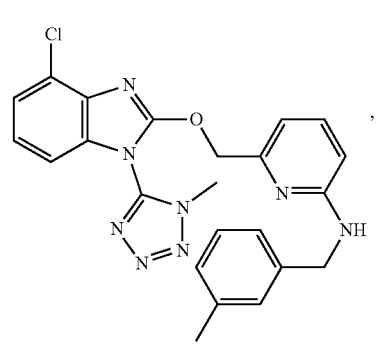
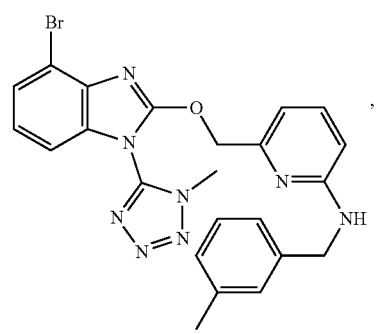
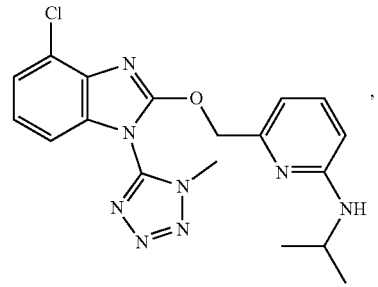

-continued

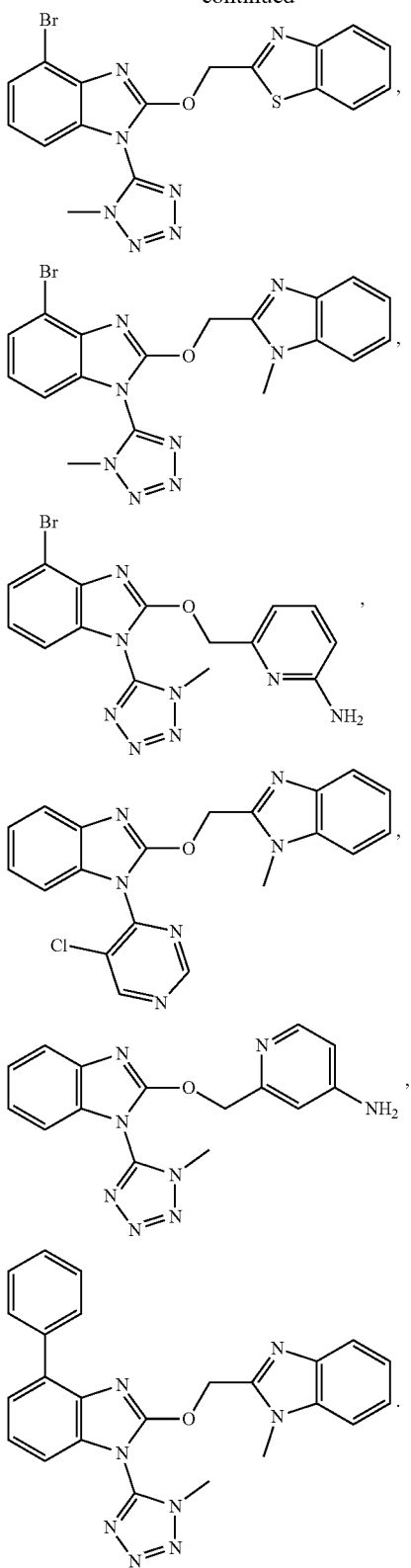

The compound of formula (I) may be as described in the following numbered paragraphs:

1. A compound of formula (I), or an agronomically acceptable salt or N-oxide thereof:

(I)

wherein -$L^1$- is independently —$(CR^4R^4)_n$—O—$C(R^4R^4)_n$—;

wherein $X^1$, $X^2$, $X^3$ and $X^4$ are each selected from carbon and nitrogen; wherein no more than three of $X^1$, $X^2$, $X^3$ and $X^4$ are nitrogen; ------- is selected from a double bond or a single bond;

$X^6$ is independently selected from N and C; wherein when $X^6$ is N, the ------- bond to which $X^6$ is attached is a single bond, the ------- bond to which $X^5$ is attached is a double bond and $X^5$ is selected from N and $CR^{5a}$; or when $X^6$ is C, the ------- bond to which $X^6$ is attached is a double bond, the ------- bond to which $X^5$ is attached is a single bond, and $X^5$ is $NR^{5b}$;

$R^1$ is a heteroaryl group independently selected from thiazole and 6-membered heteroaryl group, wherein said heteroaryl group is optionally substituted with a single $R^6$ group and/or from 1 to 4 $R^7$ groups;

$R^2$ is independently selected from 5- or 6-membered heteroaryl, optionally further substituted with from 1 to 4 $R^8$ groups;

$R^3$, $R^7$ and $R^8$ are each independently at each occurrence selected from: halo, nitro, cyano, $NR^9R^{10}$, $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl, and —O—$C_1$-$C_4$-haloalkyl;

$R^4$ is independently selected from H, F, $C_1$-$C_4$-alkyl and $C_1$-$C_4$-haloalkyl;

or two $R^4$ groups that are attached to the same carbon, together with the carbon to which they are attached, form a $C_3$-$C_5$-cycloalkyl group;

$R^{5a}$ is independently selected from H, halo and $C_1$-$C_4$-alkyl;

$R^{5b}$ is independently selected from H and $C_1$-$C_4$-alkyl;

$R^6$ is $NR^{12}R^{13}$;

$R^9$ is independently at each occurrence selected from H, $C_3$-$C_6$-cycloalkyl, $C_1$-$C_6$-alkyl, $C(O)$—$C_1$-$C_6$-alkyl, $C(O)O$—$C_1$-$C_6$-alkyl, $C(O)NR^{10}R^{10}$, and $S(O)_2$—$C_1$-$C_6$-alkyl;

$R^{10}$, $R^{12}$, $R^{15}$ and $R^{19}$ are each independently at each occurrence selected from H, $C_1$-$C_6$-alkyl and $C_3$-$C_6$-cycloalkyl;

or where two $R^{10}$ groups are attached to the same nitrogen atom, the two $R^{10}$ groups together with the nitrogen atom to which they are attached may form a 4- to 7-membered heterocycloalkyl ring;

or $R^9$ and $R^{10}$ together with the nitrogen to which they are attached form a 4- to 7-membered heterocycloalkyl ring;

$R^{11}$ is independently at each occurrence selected from H, $C_1$-$C_6$-alkyl, $C_1$-$C_6$-haloalkyl, $C_3$-$C_6$-alkenyl, $C_3$-$C_6$-alkynyl, $C_0$-$C_3$-alkylene-$R^{11a}$; wherein $R^{11a}$ is independently selected from $C_3$-$C_6$-cycloalkyl and 3- to 6-membered heterocycloalkyl;

$R^{13}$ is independently selected from: H, $C_1$-$C_6$-alkyl, phenyl, 4- to 7-membered heterocycloalkyl, 5-, 6-, 9- or 10-membered heteroaryl, $C(S)$-$L^2$-$R^{14}$ and $C(O)$-$L^2$-$R^{14}$;

-$L^2$- is absent or is independently selected from —O—, —S—, and —$NR^{15}$—;

$R^{14}$ is independently selected from $C_1$-$C_8$-alkyl, $C_1$-$C_8$-haloalkyl, $C_3$-$C_8$-alkenyl, $C_3$-$C_8$-alkynyl, $C_0$-$C_3$-alkylene-$R^{16}$; and —$CR^{17}R^{17}L^3R^{18}$;

-$L^3$- is independently selected from —O—, —S— and —$NR^{19}$—;

$R^{17}$ is independently at each occurrence selected from F, H and $C_1$-$C_4$-alkyl;

$R^{18}$ is independently selected from H, $C_1$-$C_8$-alkyl, $C_1$-$C_8$-haloalkyl, $C_3$-$C_8$-alkenyl, $C_3$-$C_8$-alkynyl and $C_0$-$C_3$-alkylene-$R^{20}$;

$R^{16}$ and $R^{20}$ are each independently at each occurrence selected from $C_3$-$C_6$-cycloalkyl, 3- to 6-membered heterocycloalkyl, 5- or 6-membered heteroaryl and phenyl;

y is an integer selected from 0, 1, 2, 3 and 4;

n is independently at each occurrence selected from 0, 1, 2 and 3;

with the proviso that where -$L^1$- is —O—$(CR^4R^4)$—, $R^1$ is not substituted with $R^6$ and $R^7$ is independently at each occurrence selected from: halo, nitro, cyano, $NR^{10}R^{10}$, $NR^{10}S(O)_2R^{10}$ $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl and —O—$C_1$-$C_4$-haloalkyl wherein where any $R^1$-$R^{20}$ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H and $C_1$-$C_4$-alkyl; and $R^b$ is independently at each occurrence selected from H, $C_3$-$C_6$-cycloalkyl, $C_1$-$C_4$-alkyl, $C(O)$—$C_1$-$C_4$-alkyl and $S(O)_2$—$C_1$-$C_4$-alkyl;

provided that the compound is not:

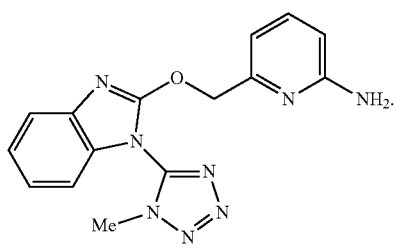 [SMILES: Cn1nnnc1-n1c(OCc2cccc(N)n2)nc2ccccc21]

2. A compound of paragraph 1, wherein $X^5$ and $X^6$ are each N.

3. A compound of paragraph 1 or paragraph 2, wherein $X^1$, $X^2$, $X^3$ and $X^4$ are each carbon.

4. A compound of any one of paragraphs 1 to 3, wherein $L^1$ is —O—$CR^4R^4$—.

5. A compound of paragraph 4, wherein -$L^1$- is —O—$CH_2$—.

6. A compound of any preceding paragraph, wherein $R^1$ has a nitrogen atom in the ring directly attached to the carbon atom to which $R^1$ is attached to the rest of the molecule.

7. A compound of paragraph 6, wherein $R^1$ is a 6-membered heteroaryl group.

8. A compound of paragraph 7, wherein $R^1$ has the structure:

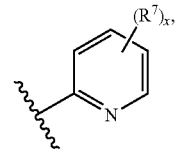

wherein x is an integer selected from 0, 1, 2, 3 and 4.

9. A compound of paragraph 8, wherein $R^1$ has the structure:

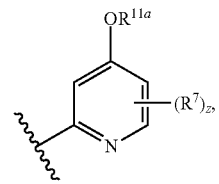

wherein $R^{11a}$ is independently selected from H, $C_1$-$C_6$-alkyl, $C_1$-$C_6$-haloalkyl, and $C_3$-$C_6$-cycloalkyl; and z is an integer selected from 0, 1, 2 and 3

10. A compound of paragraph 6, wherein $R^1$ has the structure:

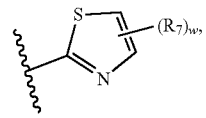

wherein w is an integer selected from 0, 1 and 2.

11. A compound of any preceding paragraph, wherein $R^2$ is substituted at a position adjacent to the point of connection of $R^2$ to the rest of the molecule with an $R^{8b}$ group, wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_5$-cycloalkyl, 3- to 6-membered heterocycloalkyl, 5- or 6-membered heteroaryl and $C_1$-$C_4$-haloalkyl.

12. A compound of any preceding paragraph, wherein $R^2$ has the structure:

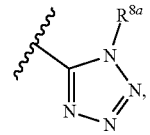

wherein $R^{8a}$ is independently selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

13. A compound of formula (Ib), or an agronomically acceptable salt or N-oxide thereof:

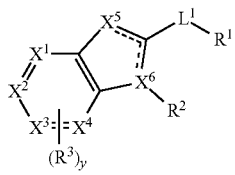

(Ib)

wherein -L¹- is independently —(CR⁴R⁴)ₙ—O—C(R⁴R⁴)ₙ—;
wherein X¹, X², X³ and X⁴ are each selected from carbon and nitrogen; wherein no more than three of X¹, X², X³ and X⁴ are nitrogen;
------- is selected from a double bond or a single bond;
X⁶ is independently selected from N and C; wherein when X⁶ is N, the ------- bond to which X⁶ is attached is a single bond, the ------- bond to which X⁵ is attached is a double bond and X⁵ is selected from N and CR⁵ᵃ; or when X⁶ is C, the ------- bond to which X⁶ is attached is a double bond, the ------- bond to which X⁵ is attached is a single bond, and X⁵ is NR⁵ᵇ;
R¹ is a heteroaryl group independently selected from thiazole and 6-membered heteroaryl group, wherein said heteroaryl group is optionally substituted with a single R⁶ group and/or from 1 to 4 R⁷ groups; wherein R¹ has a nitrogen atom in the ring directly attached to the carbon atom to which R¹ is attached to the rest of the molecule;
R² is independently selected from 5- or 6-membered heteroaryl, optionally further substituted with from 1 to 4 R⁸ groups;
R³, R⁷ and R⁸ are each independently at each occurrence selected from: halo, nitro, cyano, NR⁹R¹⁰, OR¹¹, SR¹⁰, S(O)R¹⁰, OS(O)₂R¹⁰, S(O)₂R¹⁰, S(O)₂NR¹⁰R¹⁰, CO₂R¹⁰, C(O)R¹⁰, CONR¹⁰R¹⁰, C₁-C₆-alkyl, C₂-C₆-alkenyl, C₂-C₆-alkynyl, C₁-C₆-haloalkyl, phenyl, C₃-C₆-cycloalkyl, 3- to 6-membered heterocycloalkyl, 5- or 6-membered heteroaryl, and —O—C₁-C₆-haloalkyl;
R⁴ is independently selected from H, F, C₁-C₄-alkyl and C₁-C₄-haloalkyl; or two R⁴ groups that are attached to the same carbon, together with the carbon to which they are attached, form a C₃-C₅-cycloalkyl group;
R⁵ᵃ is independently selected from H, halo and C₁-C₄-alkyl;
R⁵ᵇ is independently selected from H and C₁-C₄-alkyl;
R⁶ is independently selected from H and NHR¹³;
R⁹ is independently at each occurrence selected from H, C₃-C₆-cycloalkyl, C₁-C₆-alkyl, C(O)—C₁-C₆-alkyl, C(O)O—C₁-C₆-alkyl, C(O)NR¹⁰R¹⁰, and S(O)₂—C₁-C₆-alkyl;
R¹⁰, R¹⁵ and R¹⁹ are each independently at each occurrence selected from H, C₁-C₆-alkyl and C₃-C₆-cycloalkyl;
or where two R¹⁰ groups are attached to the same nitrogen atom, the two R¹⁰ groups together with the nitrogen atom to which they are attached may form a 4- to 7-membered heterocycloalkyl ring;
or R⁹ and R¹⁰ together with the nitrogen to which they are attached form a 4- to 7-membered heterocycloalkyl ring;
R¹¹ is independently at each occurrence selected from H, C₁-C₆-alkyl, C₁-C₆-haloalkyl, C₃-C₆-alkenyl, C₃-C₆-alkynyl, C₀-C₃-alkylene-R¹¹ᵃ; wherein R¹¹ᵃ is independently selected from C₃-C₆-cycloalkyl and 3- to 6-membered heterocycloalkyl;
R¹³ is independently selected from: H, S(O)₂—C₁-C₆-alkyl, C₁-C₆-alkyl, C₃-C₇-cycloalkyl, C₁-C₄-alkylene-R¹³ᵃ, phenyl, 4- to 7-membered heterocycloalkyl, 5-, 6-, 9- or 10-membered heteroaryl, C(S)-L²-R¹⁴ and C(O)-L²-R¹⁴;
wherein R¹³ᵃ is independently selected from: C₃-C₆-cycloalkyl, 4- to 7-membered heterocycloalkyl, phenyl, 5- or 6-membered heteroaryl, —O—C₀-C₃-alkylene-C₃-C₆-cycoalkyl and —O—C₁-C₄-alkyl;
-L²- is absent or is independently selected from —O—, —S—, and —NR¹⁵—;
R¹⁴ is independently selected from C₁-C₈-alkyl, C₁-C₈-haloalkyl, C₃-C₈-alkenyl, C₃-C₈-alkynyl, C₀-C₃-alkylene-R¹⁶; and —CR¹⁷R¹⁷L³R¹⁸;
-L³- is independently selected from —O—, —S— and —NR¹⁹—;
R¹⁷ is independently at each occurrence selected from F, H and C₁-C₄-alkyl;
R¹⁸ is independently selected from H, C₁-C₈-alkyl, C₁-C₈-haloalkyl, C₃-C₈-alkenyl, C₃-C₈-alkynyl and C₀-C₃-alkylene-R²⁰;
R¹⁶ and R²⁰ are each independently at each occurrence selected from C₃-C₆-cycloalkyl, 3- to 6-membered heterocycloalkyl, 5- or 6-membered heteroaryl and phenyl;
y is an integer selected from 0, 1, 2, 3 and 4;
n is independently at each occurrence selected from 0, 1, 2 and 3;
with the proviso that where -L¹- is —O—(CR⁴R⁴)—, R¹ is not substituted with R⁶, and R⁷ is independently at each occurrence selected from: halo, nitro, cyano, NR¹⁰R¹⁰, NR¹⁰S(O)₂R¹⁰ OR¹¹, SR¹⁰, S(O)R¹⁰, OS(O)₂R¹⁰, S(O)₂R¹⁰, S(O)₂NR¹⁰R¹⁰, CO₂R¹⁰, C(O)R¹⁰, CONR¹⁰R¹⁰, C₁-C₆-alkyl, C₂-C₆-alkenyl, C₂-C₆-alkynyl, C₁-C₆-haloalkyl, phenyl, C₃-C₆-cycloalkyl, 3- to 6-membered heterocycloalkyl, 5- or 6-membered heteroaryl and —O—C₁-C₆-haloalkyl
wherein where any R¹-R²⁰ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =NRᵃ, =NORᵃ, halo, nitro, cyano, NRᵃRᵇ, NRᵃS(O)₂Rᵃ, NRᵃC(O)Rᵃ, NRᵃCONRᵃRᵃ, NRᵃCO₂Rᵃ, ORᵃ, SRᵃ, S(O)Rᵃ, S(O)₂Rᵃ, S(O)₂NRᵃRᵃ, CO₂Rᵃ, C(O)Rᵃ, CONRᵃRᵃ, C₁-C₄-alkyl, C₂-C₄-alkenyl, C₂-C₄-alkynyl, C₃-C₆-cycloalkyl and C₁-C₄-haloalkyl;
wherein Rᵃ is independently at each occurrence selected from H and C₁-C₄-alkyl; and Rᵇ is independently at each occurrence selected from H, C₃-C₆-cycloalkyl, C₁-C₄-alkyl, C(O)—C₁-C₄-alkyl and S(O)₂—C₁-C₄-alkyl;
provided that the compound is not:

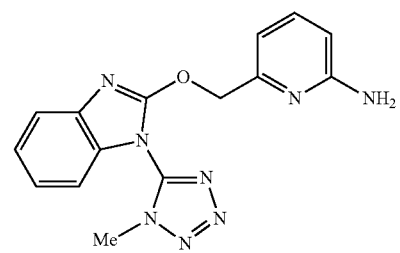 [SMILES: Cn1nnnc1-n1c(OCc2cccc(N)n2)nc2ccccc21]

14. A compound of paragraph 13, wherein X⁵ and X⁶ are each N.
15. A compound of paragraph 13 or paragraph 14, wherein X¹, X², X³ and X⁴ are each carbon.
16. A compound of any one of paragraphs 13 to 15, wherein L¹ is —O—CR⁴R⁴—.
17. A compound of paragraph 16, wherein -L¹- is —O—CH₂—.

18. A compound of any one of paragraphs 13 to 17, wherein $R^1$ has the structure:

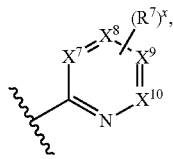

wherein $X^7$, $X^8$ and $X^9$ are each selected from carbon and nitrogen; $X^{10}$ is independently selected from nitrogen and $CR^6$; providing no more than one of $X^7$, $X^8$, $X^9$ and $X^{10}$ are nitrogen; and wherein x is an integer selected from 0, 1, 2 and 3.

19. A compound of paragraph 18, wherein $R^1$ has the structure:

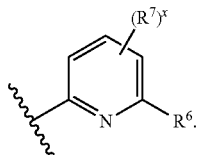

20. A compound of paragraph 19, wherein $R^1$ has the structure:

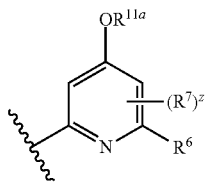

wherein $R^{11a}$ is independently selected from H, $C_1$-$C_6$-alkyl, $C_1$-$C_6$-haloalkyl, and $C_3$-$C_6$-cycloalkyl; and z is an integer selected from 0, 1 and 2.

21. A compound of any one of paragraphs 13 to 17, wherein $R^1$ has the structure:

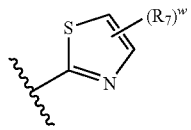

wherein w is an integer selected from 0, 1 and 2.

22. A compound of any one of paragraphs 13 to 21, wherein $R^6$ is H.
23. A compound of any one of paragraphs 13 to 21, wherein $R^6$ is $NHR^{13}$.
24. A compound of paragraph 23, wherein $R^{13}$ may be independently selected from: $C_1$-$C_6$-alkyl, $C_3$-$C_6$-cycloalkyl, and $C_1$-$C_4$-alkylene-$R^{13a}$.
25. A compound of any one of claims 13 to 24, wherein $R^2$ is substituted at a position adjacent to the point of connection of $R^2$ to the rest of the molecule with an $R^{8b}$ group, wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

26. A compound of any one of paragraphs 13 to 25, wherein $R^2$ has the structure:

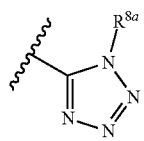

wherein $R^{8a}$ is independently selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

27. A method for controlling fungal diseases, the method comprising applying an agronomically effective and substantially non-phytotoxic quantity of a compound to seeds of plants, to plants themselves or to an area where it is intended that plants will grow; wherein the compound is selected from a compound of any one of paragraphs 1 to 26 and

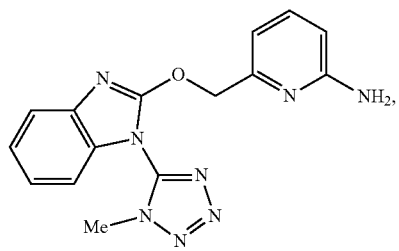 [SMILES: Cn1nnnc1-n1c(OCc2cccc(N)n2)nc2ccccc21]

or an agronomically acceptable salt or N-oxide thereof.

28. A use of a compound to control fungal diseases; wherein the compound is selected from a compound of any one of paragraphs 1 to 26 and

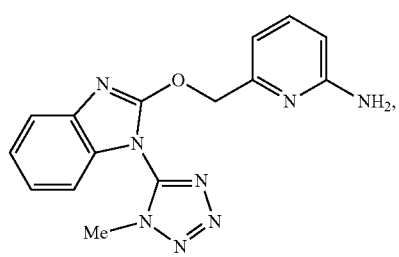 [SMILES: Cn1nnnc1-n1c(OCc2cccc(N)n2)nc2ccccc21]

or an agronomically acceptable salt or N-oxide thereof.

29. A fungicidal composition comprising an effective and non-phytotoxic amount of a compound; wherein the compound is selected from a compound of any one of paragraphs 1 to 26 and

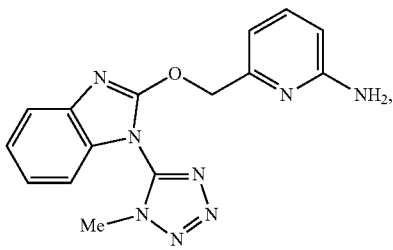 [SMILES: Cn1nnnc1-n1c(OCc2cccc(N)n2)nc2ccccc21]

or an agronomically acceptable salt or N-oxide thereof.

30. A compound of formula (Ic), or an agronomically acceptable salt or N-oxide thereof:

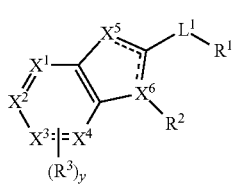

wherein -$L^1$- is independently —$(CR^4R^4)_n$—O—C($R^4$$R^4$)$_n$—;

wherein $X^1$, $X^2$, $X^3$ and $X^4$ are each selected from carbon and nitrogen; wherein no more than three of $X^1$, $X^2$, $X^3$ and $X^4$ are nitrogen;

═══════ is selected from a double bond or a single bond;

$X^6$ is independently selected from N and C; wherein when $X^6$ is N, the ═══════ bond to which $X^6$ is attached is a single bond, the ═══════ bond to which $X^5$ is attached is a double bond and $X^5$ is selected from N and $CR^{5a}$; or when $X^6$ is C, the ═══════ bond to which $X^6$ is attached is a double bond, the ═══════ bond to which $X^5$ is attached is a single bond, and $X^5$ is $NR^{5b}$;

$R^1$ is a heteroaryl group independently selected from thiazole and 6, 9- or 10-membered heteroaryl group, wherein said heteroaryl group is optionally substituted with a single $R^6$ group and/or from 1 to 4 $R^7$ groups; wherein $R^1$ has a nitrogen atom in the ring to which $R^1$ is attached to the rest of the molecule, said nitrogen atom being directly attached to the carbon atom to which $R^1$ is attached to the rest of the molecule;

$R^2$ is independently selected from 5- or 6-membered heteroaryl, optionally further substituted with from 1 to 4 $R^8$ groups;

$R^3$, $R^7$ and $R^8$ are each independently at each occurrence selected from: halo, nitro, cyano, $NR^9R^{10}$, $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl, and —O—$C_1$-$C_6$-haloalkyl;

$R^4$ is independently selected from H, F, $C_1$-$C_4$-alkyl and $C_1$-$C_4$-haloalkyl;

or two $R^4$ groups that are attached to the same carbon, together with the carbon to which they are attached, form a $C_3$-$C_5$-cycloalkyl group;

$R^{5a}$ is independently selected from H, halo and $C_1$-$C_4$-alkyl;

$R^{5b}$ is independently selected from H and $C_1$-$C_4$-alkyl;

$R^6$ is independently selected from H and $NHR^{13}$;

$R^9$ is independently at each occurrence selected from H, $C_3$-$C_6$-cycloalkyl, $C_1$-$C_6$-alkyl, C(O)—$C_1$-$C_6$-alkyl, C(O)O—$C_1$-$C_6$-alkyl, $C(O)NR^{10}R^{10}$, and $S(O)_2$—$C_1$-$C_6$-alkyl;

$R^{10}$, $R^{15}$ and $R^{19}$ are each independently at each occurrence selected from H, $C_1$-$C_6$-alkyl and $C_3$-$C_6$-cycloalkyl;

or where two $R^{10}$ groups are attached to the same nitrogen atom, the two $R^{10}$ groups together with the nitrogen atom to which they are attached may form a 4- to 7-membered heterocycloalkyl ring;

or $R^9$ and $R^{10}$ together with the nitrogen to which they are attached form a 4- to 7-membered heterocycloalkyl ring;

$R^{11}$ is independently at each occurrence selected from H, $C_1$-$C_6$-alkyl, $C_1$-$C_6$-haloalkyl, $C_3$-$C_6$-alkenyl, $C_3$-$C_6$-alkynyl, $C_0$-$C_3$-alkylene-$R^{11a}$; wherein $R^{11a}$ is independently selected from $C_3$-$C_6$-cycloalkyl and 3- to 6-membered heterocycloalkyl;

$R^{13}$ is independently selected from: H, $S(O)_2$—$C_1$-$C_6$-alkyl, $C_1$-$C_6$-alkyl, $C_3$-$C_7$-cycloalkyl, $C_1$-$C_4$-alkylene-$R^{13a}$, phenyl, 4- to 7-membered heterocycloalkyl, 5-, 6-, 9- or 10-membered heteroaryl, C(S)-$L^2$-$R^{14}$ and C(O)-$L^2$-$R^{14}$;

wherein $R^{13a}$ is independently selected from: $C_3$-$C_6$-cycloalkyl, 4- to 7-membered heterocycloalkyl, phenyl, 5- or 6-membered heteroaryl, —O—$C_0$-$C_3$-alkylene-$C_3$-$C_6$-cycloalkyl, —O—$C_0$-$C_3$-alkylene-phenyl and —O—$C_1$-$C_4$-alkyl;

-$L^2$- is absent or is independently selected from —O—, —S—, and —$NR^{15}$—;

$R^{14}$ is independently selected from $C_1$-$C_8$-alkyl, $C_1$-$C_8$-haloalkyl, $C_3$-$C_8$-alkenyl, $C_3$-$C_8$-alkynyl, $C_0$-$C_3$-alkylene-$R^{16}$; and —$CR^{17}R^{17}L^3R^{18}$.

-$L^3$- is independently selected from —O—, —S— and —$NR^{19}$—;

$R^{17}$ is independently at each occurrence selected from F, H and $C_1$-$C_4$-alkyl;

$R^{18}$ is independently selected from H, $C_1$-$C_8$-alkyl, $C_1$-$C_8$-haloalkyl, $C_3$-$C_8$-alkenyl, $C_3$-$C_8$-alkynyl and $C_0$-$C_3$-alkylene-$R^{20}$;

$R^{16}$ and $R^{20}$ are each independently at each occurrence selected from $C_3$-$C_6$-cycloalkyl, 3- to 6-membered heterocycloalkyl, 5- or 6-membered heteroaryl and phenyl;

y is an integer selected from 0, 1, 2, 3 and 4;

n is independently at each occurrence selected from 0, 1, 2 and 3;

with the proviso that where -$L^1$- is —O—$(CR^4R^4)_n$—, $R^{13}$ is not selected from C(S)-$L^2$-$R^{14}$ and C(O)-$L^2$-$R^{14}$, and $R^7$ is independently at each occurrence selected from: halo, nitro, cyano, $NR^{10}R^{10}$, $NR^{10}S(O)_2R^{10}$ $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl and —O—$C_1$-$C_6$-haloalkyl wherein where any $R^1$-$R^{20}$ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$, $C(O)R^a$, $CONR^aR^a$, $C_1$-$C_4$-alkyl, $C_2$-$C_4$-alkenyl, $C_2$-$C_4$-alkynyl, $C_3$-$C_6$-cycloalkyl and $C_1$-$C_4$-haloalkyl;

wherein $R^a$ is independently at each occurrence selected from H and $C_1$-$C_4$-alkyl; and $R^b$ is independently at each occurrence selected from H, $C_3$-$C_6$-cycloalkyl, $C_1$-$C_4$-alkyl, C(O)—$C_1$-$C_4$-alkyl and $S(O)_2$—$C_1$-$C_4$-alkyl;

provided that the compound is not selected from:

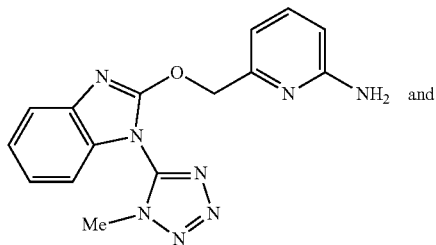

and

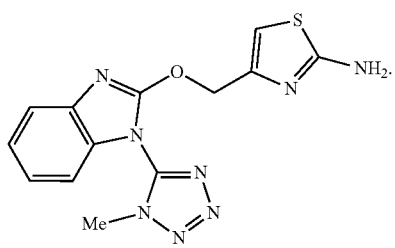

31. A compound of paragraph 30, wherein $X^5$ and $X^6$ are each N.
32. A compound of paragraph 30 or paragraph 31, wherein $X^1$, $X^2$, $X^3$ and $X^4$ are each carbon.
33. A compound of any one of paragraphs 30 to 32, wherein $L^1$ is —O—$CR^4R^4$—.
34. A compound of paragraph 33, wherein -$L^1$- is —O—$CH_2$—.
35. A compound of any one of paragraphs 30 to 34, wherein $R^1$ has the structure:

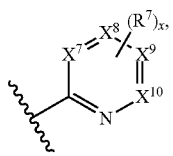

wherein $X^7$, $X^8$ and $X^9$ are each selected from carbon and nitrogen; $X^{10}$ is independently selected from nitrogen and $CR^6$; providing no more than one of $X^7$, $X^8$, $X^9$ and $X^{10}$ are nitrogen; and wherein x is an integer selected from 0, 1, 2 and 3.

36. A compound of paragraph 35, wherein $R^1$ has the structure:

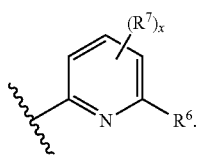

37. A compound of paragraph 36, wherein $R^1$ has the structure:

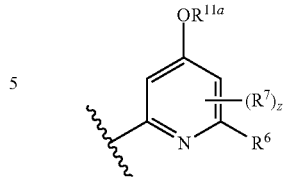

wherein $R^{11a}$ is independently selected from H, $C_1$-$C_6$-alkyl, $C_1$-$C_6$-haloalkyl, and $C_3$-$C_6$-cycloalkyl; and z is an integer selected from 0, 1 and 2.

38. A compound of any one of paragraphs 30 to 34, wherein $R^1$ has the structure:

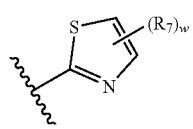

wherein w is an integer selected from 0, 1 and 2.

39. A compound of any one of paragraphs 30 to 37, wherein $R^6$ is H.
40. A compound of any one of paragraphs 30 to 39, wherein $R^6$ is $NHR^{13}$.
41. A compound of paragraph 40, wherein $R^{13}$ may be independently selected from: $C_1$-$C_6$-alkyl, $C_3$-$C_6$-cycloalkyl, and $C_1$-$C_4$-alkylene-$R^{13a}$.
42. A compound of any one of paragraphs 30 to 41, wherein $R^2$ is substituted at a position adjacent to the point of connection of $R^2$ to the rest of the molecule with an $R^{8b}$ group, wherein $R^{8b}$ is selected from chloro, bromo, $C_1$-$C_4$-alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.
43. A compound of any one of paragraphs 30 to 42, wherein $R^2$ has the structure:

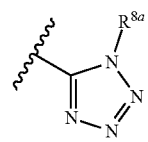

wherein $R^{8a}$ is independently selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

44. A method for controlling fungal diseases, the method comprising applying an agronomically effective and substantially non-phytotoxic quantity of a compound to seeds of plants, to plants themselves or to an area where it is intended that plants will grow; wherein the compound is selected from a compound of any one of paragraphs 30 to 43,

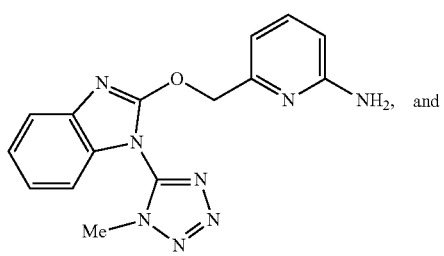

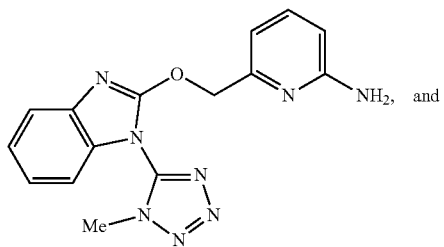

or an agronomically acceptable salt or N-oxide thereof.

45. A use of a compound to control fungal diseases; wherein the compound is selected from a compound of any one of paragraphs 30 to 43,

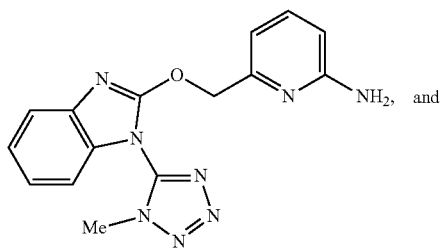

or an agronomically acceptable salt or N-oxide thereof.

46. A fungicidal composition comprising an effective and non-phytotoxic amount of a compound; wherein the compound is selected from a compound of any one of paragraphs 30 to 43,

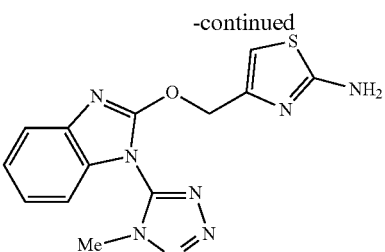

-continued

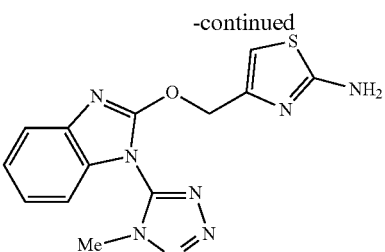

or an agronomically acceptable salt or N-oxide thereof.

DETAILED DESCRIPTION

The term $C_m$-$C_n$ refers to a group with m to n carbon atoms.

The term "alkyl" refers to a monovalent linear or branched saturated hydrocarbon chain. For example, "$C_1$-$C_6$-alkyl" may refer to methyl, ethyl, n-propyl, iso-propyl, n-butyl, sec-butyl, tert-butyl, n-pentyl and n-hexyl. The alkyl groups may be unsubstituted or substituted by one or more substituents. Specific substituents for each alkyl group independently may be fluorine, $OR^a$ or $NHR^a$.

The term "alkylene" refers to a bivalent linear saturated hydrocarbon chain. For example, "$C_1$-$C_3$-alkylene" may refer to methylene, ethylene or propylene. The alkylene groups may be unsubstituted or substituted by one or more substituents. Specific substituents for each alkylene group independently may be methyl, fluorine, $OR^a$ or $NHR^a$.

The term "haloalkyl" refers to a hydrocarbon chain substituted with at least one halogen atom independently chosen at each occurrence from: fluorine, chlorine, bromine and iodine. The halogen atom may be present at any position on the hydrocarbon chain. For example, "$C_1$-$C_6$-haloalkyl" may refer to chloromethyl, fluoromethyl, trifluoromethyl, chloroethyl e.g. 1-chloromethyl and 2-chloroethyl, trichloroethyl e.g. 1,2,2-trichloroethyl, 2,2,2-trichloroethyl, fluoroethyl e.g. 1-fluoroethyl and 2-fluoroethyl, trifluoroethyl e.g. 1,2,2-trifluoroethyl and 2,2,2-trifluoroethyl, chloropropyl, trichloropropyl, fluoropropyl, trifluoropropyl. A haloalkyl group may be a fluoroalkyl group, i.e. a hydrocarbon chain substituted with at least one fluorine atom. Thus, a haloalkyl group may have any amount of halogen substituents. The group may contain a single halogen substituent, it may have two or three halogen substituents, or it may be saturated with halogen substituents.

The term "alkenyl" refers to a branched or linear hydrocarbon chain containing at least one double bond. The double bond(s) may be present as the E or Z isomer. The double bond may be at any possible position of the hydrocarbon chain. For example, "$C_2$-$C_6$-alkenyl" may refer to ethenyl, propenyl, butenyl, butadienyl, pentenyl, pentadienyl, hexenyl and hexadienyl. The alkenyl groups may be unsubstituted or substituted by one or more substituents. Specific substituents for any saturated carbon atom in each alkenyl group independently may be fluorine, $OR^a$ or $NHR^a$.

The term "alkynyl" refers to a branched or linear hydrocarbon chain containing at least one triple bond. The triple bond may be at any possible position of the hydrocarbon chain. For example, "$C_2$-$C_6$-alkynyl" may refer to ethynyl, propynyl, butynyl, pentynyl and hexynyl. The alkynyl groups may be unsubstituted or substituted by one or more substituents. Specific substituents for any saturated carbon atom in each alkynyl group independently may be fluorine, $OR^a$ or $NHR^a$.

The term "cycloalkyl" refers to a saturated hydrocarbon ring system containing 3, 4, 5 or 6 carbon atoms. For example, "$C_3$-$C_6$-cycloalkyl" may refer to cyclopropyl, cyclobutyl, cyclopentyl, cyclohexyl. The cycloalkyl groups may be unsubstituted or substituted by one or more substituents. Specific substituents for each cycloalkyl group independently may be fluorine, $OR^a$ or $NHR^a$. The term "y-to z-membered heterocycloalkyl" may refer to a monocyclic or bicyclic saturated or partially saturated group having from y to z atoms in the ring system and comprising 1 or 2 heteroatoms independently selected from O, S and N in the ring system (in other words 1 or 2 of the atoms forming the ring system are selected from O, S and N). By partially saturated it is meant that the ring may comprise one or two double bonds. This applies particularly to monocyclic rings with from 5 to 6 members. The double bond will typically be between two carbon atoms but may be between a carbon atom and a nitrogen atom. A heterocycloalkyl group may mean a saturated heterocycloalkyl group. Examples of heterocycloalkyl groups include; piperidine, piperazine, morpholine, thiomorpholine, pyrrolidine, tetrahydrofuran, tetrahydrothiophene, dihydrofuran, tetrahydropyran, dihydropyran, dioxane, azepine. A heterocycloalkyl group may be unsubstituted or substituted by one or more substituents. Specific substituents for any saturated carbon atom in each heterocycloalkyl group may independently be fluorine, $OR^a$ or $NHR^a$.

The term "oxo" refers to an oxygen atom attached to a carbon on the indicated group via a double bond. Aryl groups may be any aromatic carbocyclic ring system (i.e. a ring system containing $2(2n+1)\pi$ electrons). Aryl groups may have from 6 to 12 carbon atoms in the ring system. Aryl groups will typically be phenyl groups. Aryl groups may be naphthyl groups or biphenyl groups.

In any of the above aspects and embodiments, heteroaryl groups may be any aromatic (i.e. a ring system containing $2(2n+1)\pi$ electrons) 5 or 6 membered ring system comprising from 1 to 4 heteroatoms independently selected from O, S and N (in other words from 1 to 4 of the atoms forming the ring system are selected from O, S and N). Thus, any heteroaryl groups may be independently selected from: 5 membered heteroaryl groups in which the heteroaromatic ring is substituted with 1-4 heteroatoms independently selected from O, S and N; and 6-membered heteroaryl groups in which the heteroaromatic ring is substituted with 1-3 (e.g. 1-2) nitrogen atoms. Specifically, heteroaryl groups may be independently selected from: pyrrole, furan, thiophene, pyrazole, imidazole, oxazole, isoxazole, triazole, oxadiazole, thiadiazole, tetrazole; pyridine, pyridazine, pyrimidine, pyrazine, triazine.

It may be that, in any $R^1$-$R^{20}$ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, $=NR^a$, $=NOR^a$, halo, nitro, cyano, $NR^aR^b$, $NR^aS(O)_2R^a$, $NR^aC(O)R^a$, $NR^aCONR^aR^a$, $NR^aCO_2R^a$, $OR^a$, $SR^a$, $S(O)R^a$, $S(O)_2R^a$, $S(O)_2NR^aR^a$, $CO_2R^a$ $C(O)R^a$, $CONR^aR^a$, $C_1$-$C_4$-alkyl, $C_2$-$C_4$-alkenyl, $C_2$-$C_4$-alkynyl and $C_1$-$C_4$-haloalkyl; wherein $R^a$ is independently at each occurrence selected from H, $C_1$-$C_4$-alkyl and $C_1$-$C_4$ haloalkyl; and $R^b$ is independently at each occurrence selected from H, $C_3$-$C_5$-cycloalkyl, $C_1$-$C_4$-alkyl, $C(O)$—$C_1$-$C_4$-alkyl and $S(O)_2$—$C_1$-$C_4$-alkyl Compounds of the invention containing one or more asymmetric carbon atoms can exist as two or more stereoisomers. Where a compound of the invention contains a double bond such as a C=C or C=N group, geometric cis/trans (or Z/E) isomers are possible. Where structural isomers are interconvertible via a low energy barrier, tautomeric isomerism ('tautomerism') can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of the invention, including compounds exhibiting more than one type of isomerism, and mixtures of one or more thereof. Also included are acid addition or base salts wherein the counter ion is optically active, for example, D-lactate or L-lysine, or racemic, for example, DL-tartrate or DL-arginine.

The compounds of the invention may be obtained, stored and/or used in the form of an agronomically acceptable salt. Suitable salts include, but are not limited to, salts of acceptable inorganic acids such as hydrochloric, sulfuric, phosphoric, nitric, carbonic, boric, sulfamic, and hydrobromic acids, or salts of agronomically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulfonic, toluenesulfonic, benzenesulfonic, salicylic, sulfanilic, aspartic, glutamic, edetic, stearic, palmitic, oleic, lauric, pantothenic, tannic, ascorbic and valeric acids. Suitable salts also include salts of inorganic and organic bases, e.g. counterions such as Na, Ca, K, Li, Mg, ammonium, trimethylsulfonium. The compounds may also be obtained, stored and/or used in the form of an N-oxide.

Cis/trans isomers may be separated by conventional techniques well known to those skilled in the art, for example, chromatography and fractional crystallisation.

Conventional techniques for the preparation/isolation of individual enantiomers when necessary include chiral synthesis from a suitable optically pure precursor or resolution of the racemate (or the racemate of a salt or derivative) using, for example, chiral high pressure liquid chromatography (HPLC). Thus, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and for specific examples, 0 to 5% by volume of an alkylamine e.g. 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

When any racemate crystallises, crystals of two different types are possible. The first type is the racemic compound (true racemate) referred to above wherein one homogeneous form of crystal is produced containing both enantiomers in equimolar amounts. The second type is the racemic mixture or conglomerate wherein two forms of crystal are produced in equimolar amounts each comprising a single enantiomer.

While both of the crystal forms present in a racemic mixture have identical physical properties, they may have different physical properties compared to the true racemate. Racemic mixtures may be separated by conventional techniques known to those skilled in the art—see, for example, "Stereochemistry of Organic Compounds" by E. L. Eliel and S. H. Wilen (Wiley, 1994).

The activity of the compounds of the present invention can be assessed by a variety of in silico, in vitro and in vivo assays. In silico analysis of a variety of compounds has been demonstrated to be predictive of ultimate in vitro and even in vivo activity.

The present invention also includes all environmentally acceptable isotopically-labelled compounds of formulae (I) to (XII) and their syntheses, wherein one or more atoms are replaced by atoms having the same atomic number, but an atomic mass or mass number different from the atomic mass or mass number usually found in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Isotopically-labelled compounds can generally be prepared by conventional techniques known to those skilled in the art or by processes analogous to those described using an appropriate isotopically-labelled reagent in place of the non-labelled reagent previously employed.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

If appropriate, the compounds of the invention can, at certain concentrations or application rates, be used as fungicides.

According to another aspect of the present invention, there is provided a method for controlling the fungal diseases of plants, crops or seeds, the method comprising applying an agronomically effective and substantially non-phytotoxic quantity of a compound to the seeds of the plants, to the plants themselves or to the area where it is intended that the plants will grow; wherein the compound is selected from a compound of the first aspect,

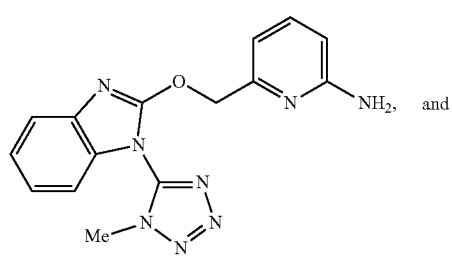

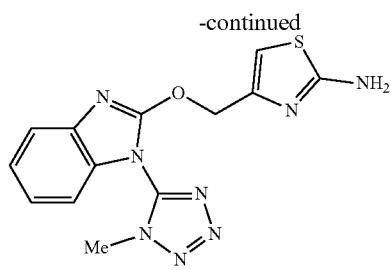

or an agronomically acceptable salt or N-oxide thereof.

According to another aspect of the present invention, there is provided a use of a compound to control fungal diseases; wherein the compound is selected from a compound of the first aspect,

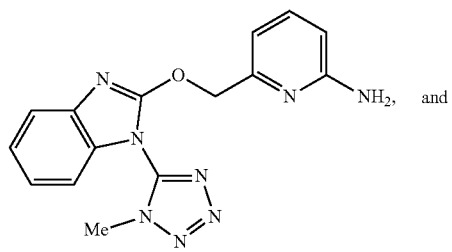

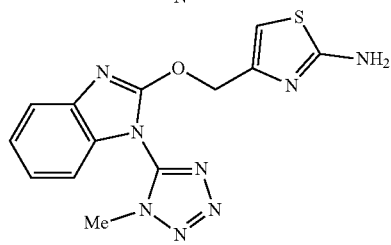

or an agronomically acceptable salt or N-oxide thereof.

The pesticide may be applied as a seed treatment, foliar application, stem application, drench or drip application (chemigation) to the seed, the plant or to the fruit of the plant or to soil or to inert substrate (e.g. inorganic substrates like sand, rockwool, glasswool; expanded minerals like perlite, vermiculite, zeolite or expanded clay), Pumbe, Pyroclastic materials or stuff, synthetic organic substrates (e.g. polyurethane) organic substrates (e.g. peat, composts, tree waste products like coir, wood fibre or chips, tree bark) or to a liquid substrate (e.g. floating hydroponic systems, Nutrient Film Technique, Aeroponics).

In a further aspect, the present invention also relates to a fungicidal composition comprising an effective and non-phytotoxic amount of a compound; wherein the compound is selected from a compound of the first aspect,

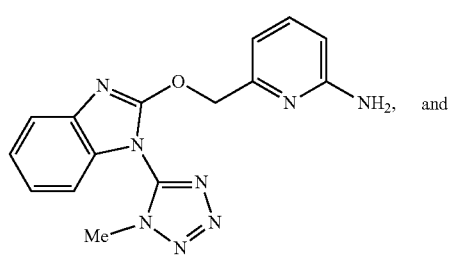

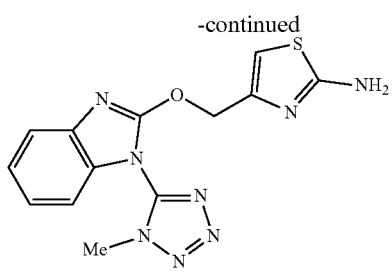

or an agronomically acceptable salt or N-oxide thereof.

The composition may further comprise one or more additional fungicides.

The term "effective and non-phytotoxic amount" means an amount of pesticide according to the invention which is sufficient to control or destroy any of the targeted pests present or liable to appear on the crops and which does not have any significant detrimental effect on the crops or indeed has a positive effect on plant vigour and yield in the absence of target organism. The amount will vary depending on the pest to be controlled, the type of crop, the climatic conditions and the compounds included in the pesticidal composition. This amount can be determined by systematic field trials, which are within the capabilities of a person skilled in the art.

Depending on their particular physical and/or chemical properties, the active compounds of the invention can be formulated as solutions, emulsions, suspensions, powders, foams, pastes, granules, aerosols, microencapsulations in polymeric substances and in coating materials for seed, and also as ULV cold and warm fogging formulations.

The active compounds can be used neat, or in the form of a formulation, e.g. ready-to-use solutions, emulsions, water- or oil-based suspensions, powders, wettable powders, pastes, soluble powders, dusts, soluble granules, granules for broadcasting, suspoemulsion concentrates, natural substances impregnated with active compound, synthetic substances impregnated with active compound, fertilizers and also microencapsulations in polymeric substances. Application may be carried out, for example, by watering, spraying, atomizing, broadcasting, dusting, foaming, spreading, etc. It is also possible to apply the active compounds by the ultra-low volume method or to inject the preparation of active compound or the active compound itself into the soil. It is also possible to treat the seed of the plants.

Formulations containing the compounds of the invention are produced in a known manner, for example by mixing the compounds with extenders (e.g. liquid solvents and/or solid carriers), optionally with the use of surfactants (e.g. emulsifiers and/or dispersants and/or foam-formers). The formulations are prepared either in factories/production plants or alternatively before or during the application.

Auxiliaries are substances which are suitable for imparting to the composition itself and/or to preparations derived therefrom (for example spray liquors, seed dressings) particular properties such as certain technical properties and/or also particular biological properties. Typical suitable auxiliaries are: extenders, solvents and carriers.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulfones and sulfoxides (such as dimethylsulfoxide).

If the extender used is water, it is also possible to use, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and also their ethers and esters, ketones such as acetone, methyl ethyl ketone, methyl isobutyl ketone or cyclohexanone, strongly polar solvents such as dimethylformamide and dimethylsulfoxide.

Suitable solid carriers are: for example, ammonium salts and ground natural minerals such as kaolins, clays, talc, chalk, quartz, attapulgite, montmorillonite or diatomaceous earth, and ground synthetic minerals, such as finely divided silica, alumina and silicates; suitable solid carriers for granules are: for example, crushed and fractionated natural rocks such as calcite, marble, pumice, sepiolite and dolomite, and also synthetic granules of inorganic and organic meals, and granules of organic material such as paper, sawdust, coconut shells, maize cobs and tobacco stalks; suitable emulsifiers and/or foam-formers are: for example, nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates and also protein hydrolysates; suitable dispersants are nonionic and/or ionic substances, for example from the classes of the alcohol-POE and/or -POP ethers, acid and/or POP-POE esters, alkylaryl and/or POP-POE ethers, fat- and/or POP-POE adducts, POE- and/or POP-polyol derivatives, POE- and/or POP-sorbitan- or -sugar adducts, alkyl or aryl sulfates, alkyl- or arylsulfonates and alkyl or aryl phosphates or the corresponding PO-ether adducts. Furthermore, suitable oligo- or polymers, for example those derived from vinylic monomers, from acrylic acid, from EO and/or PO alone or in combination with, for example, (poly)alcohols or (poly)amines. It is also possible to employ lignin and its sulfonic acid derivatives, unmodified and modified celluloses, aromatic and/or aliphatic sulfonic acids and their adducts with formaldehyde.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations.

Further additives may be mineral and vegetable oils. It is also possible to add colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc. Other possible additives are perfumes, mineral or vegetable, optionally modified oils and waxes.

The formulations may also comprise stabilizers, e.g. low-temperature stabilizers, preservatives, antioxidants, light stabilizers or other agents which improve chemical and/or physical stability.

The formulations generally comprise between 0.01 and 98% by weight of active compound, preferably between 0.1 and 95% and particularly preferably between 0.5 and 90%.

The active compounds according to the invention can also be used as a mixture with other known fungicides, for example, to improve the activity spectrum or to reduce or slow the development of resistance.

A mixture with other known active compounds such as nematicides, acaricides, herbicides, insecticides, bactericides or other fungicides, or with fertilizers and growth regulators, safeners or semiochemicals is also possible.

Exemplary application rates of the active compounds according to the invention are: when treating leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used); when treating seed: from 2 to 200 g per 100 kg of seed, preferably from 2.5 to 150 g per 100 kg of seed, and particularly preferably from 2.5 to 25 g per 100 kg of seed, very particularly preferably from 2.5 to 12.5 g per 100 kg of seed; when treating the soil: from 0.1 to 10 000 g/ha, preferably from 1 to 5 000 g/ha.

The compositions according to the invention are suitable for protecting any plant variety which is employed in agriculture, in the greenhouse, in forests or in horticulture and, in particular, cereals (e.g. wheat, barley, rye, millet and oats), maize, cotton, soya beans, rice, potatoes, sunflowers, beans, coffee, beet (for example sugar beet and fodder beet), peanuts, vegetables (e.g. tomatoes, cucumbers, onions and lettuce), lawns, fruit and nut trees (e.g. apples, pears, peaches, nectarines, apricots, hazelnut, pecan, macadamia, pistachio), soft fruit (e.g. strawberries, raspberries, blackcurrants, redcurrants), grapevines, bananas, cocoa and ornamental plants.

The active compounds of the invention, in combination with good plant tolerance and favourable toxicity to warm-blooded animals and being tolerated well by the environment, are suitable for protecting plants and plant organs, for increasing the harvest yields, for improving the quality of the harvested material and for controlling pests, in particular fungal diseases, which are encountered in agriculture, in horticulture, in animal husbandry, in forests, in gardens and leisure facilities, in the protection of stored products and of materials, and in the hygiene sector. They may be preferably employed as crop protection agents.

Use as Fungicides

The compounds of the invention have activity as fungicides.

The following are illustrative examples of agricultural pests that may be controlled by fungicidal compounds: Albugo diseases caused for example by Albugo Candida; Bremia diseases, caused for example by Bremia lactucae; Peronospora diseases, caused for example by Peronospora pisi or P. brassicae; Phytophthora diseases, caused for example by Phytophthora infestans; Plasmopara diseases, caused for example by Plasmopara viticola; Pseudoperonospora diseases, caused for example by Pseudoperonospora humuli or Pseudoperonospora cubensis; Pythium diseases, caused for example by Pythium ultimum;

The compounds of the invention may be active against a broad spectrum of oomycete fungal diseases. Alternatively, they may be active specifically against certain oomycete diseases but not others.

Notable oomycete fungal diseases are:
*Plasmopara viticola*
*Phytophthora infestans*
*Pythium ultimum*
*Bremia lactuca*
*Peronospora* spp In additional to their fungicidal activity, the compounds of the invention may also have activity against other microbes, e.g. bacteria.

The fungicidal compounds of the invention may also be used in the treatment of fungal diseases of humans and animals (e.g. mammals). Likewise, the bactericidal compounds of the invention may be used in the treatment of bacterial diseases of humans and animals. Thus, the invention includes a method of treating a fungal or bacterial disease, the method comprising administering a therapeutic amount of an antifungal agent of the invention to a subject (e.g. a human subject) in need thereof. The compound may be formulated for topical administration to the infected area of the body or it may be formulated for oral or parenteral administration.

Synthesis

The skilled person will appreciate that adaptation of methods known in the art could be applied in the manufacture of the compounds of the present invention.

For example, the skilled person will be immediately familiar with standard textbooks such as "Comprehensive Organic Transformations—A Guide to Functional Group Transformations", RC Larock, Wiley-VCH (1999 or later editions); "March's Advanced Organic Chemistry—Reactions, Mechanisms and Structure", MB Smith, J. March, Wiley, (5th edition or later); "Advanced Organic Chemistry, Part B, Reactions and Synthesis", F A Carey, R J Sundberg, Kluwer Academic/Plenum Publications, (2001 or later editions); "Organic Synthesis—The Disconnection Approach", S Warren (Wiley), (1982 or later editions); "Designing Organic Syntheses" S Warren (Wiley) (1983 or later editions); "Heterocyclic Chemistry", J. Joule (Wiley 2010 edition or later); ("Guidebook To Organic Synthesis" R K Mackie and D M Smith (Longman) (1982 or later editions), etc., and the references therein as a guide.

The skilled person is familiar with a range of strategies for synthesising organic and particularly heterocyclic molecules and these represent common general knowledge as set out in text books such as Warren "Organic Synthesis: The Disconnection Approach"; Mackie and Smith "Guidebook to Organic Chemistry"; and Clayden, Greeves, Warren and Wothers "Organic Chemistry".

The skilled chemist will exercise his judgement and skill as to the most efficient sequence of reactions for synthesis of a given target compound and will employ protecting groups as necessary. This will depend inter alia on factors such as the nature of other functional groups present in a particular substrate. Clearly, the type of chemistry involved will influence the choice of reagent that is used in the said synthetic steps, the need, and type, of protecting groups that are employed, and the sequence for accomplishing the protection/deprotection steps. These and other reaction parameters will be evident to the skilled person by reference to standard textbooks and to the examples provided herein.

Sensitive functional groups may need to be protected and deprotected during synthesis of a compound of the invention. This may be achieved by conventional methods, for example as described in "Protective Groups in Organic Synthesis" by T W Greene and P G M Wuts, John Wiley & Sons Inc. (1999), and references therein.

Throughout this specification these abbreviations have the following meanings:

| | |
|---|---|
| CDI—carbonyldiimidazole | DCM—dichloromethane |
| DDQ—2,3-dichloro-5,6-dicyano-1,4-benzoquinone | DIPEA—diisopropylethylamine |
| DMAP—N,N-dimethyl-4-aminopyridine | DMF—N,N-dimethylformamide |
| DMSO—dimethylsulfoxide | Im—imidazole |
| LDA—Lithium diisopropylamide | mCPBA—m-chloroperbenzoic acid |
| NBS—N-bromosuccinimide | PE—petroleum ether |
| PMB—para-methoxybenzyl | RT—room temperature |
| TBAF—tetrabutylammonium fluoride | Tf—trifluoromethylsulfonyl |
| THF—tetrahydrofuran | TMS—trimethylsilyl |
| TCDI—thiocarbonyldiimidazole | TBSO—t-butyldimethylsilyloxy |
| HATU—1-[Bis(dimethylamino)methylene]-1H-1,2,3-triazolo[4,5-b]pyridinium 3-oxide hexafluorophosphate | LHMDS—lithium bis(trimethylsilyl)amide |

Certain compounds of the invention can be made according to the general synthetic scheme below. Certain compounds of the invention can be made according to or by methods analogous to the methods described in Examples 1 to 109.

General Synthetic Scheme

Certain compounds of the invention can be made starting from ortho-fluoro nitro benzenes a. Treatment with amine b in the presence of a base (e.g. NaH in DMF) can provide nitroanilines of formula c. Reduction of the nitro group to an amine (e.g. using ammonium formate and palladium on carbon in ethanol) can provide the diamines d. Compounds of formula e can be formed (e.g. by treating with carbonyl diimidazole in THF at room temperature). Treatment with phosphorous oxychloride (e.g. at reflux) can provide chlorobenzimidazoles of formula f. Reaction of compounds of formula f with sodium alkoxide g (e.g. in DMF at room temperature) provides compounds of formula h, a subset of compounds of the invention (Scheme A).

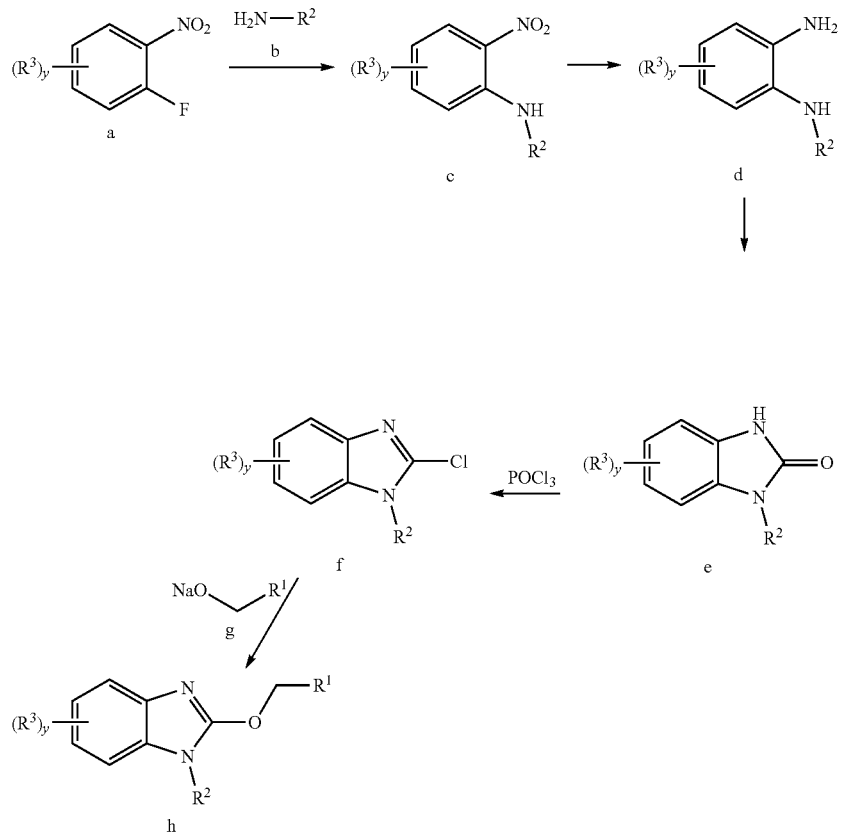

Scheme B

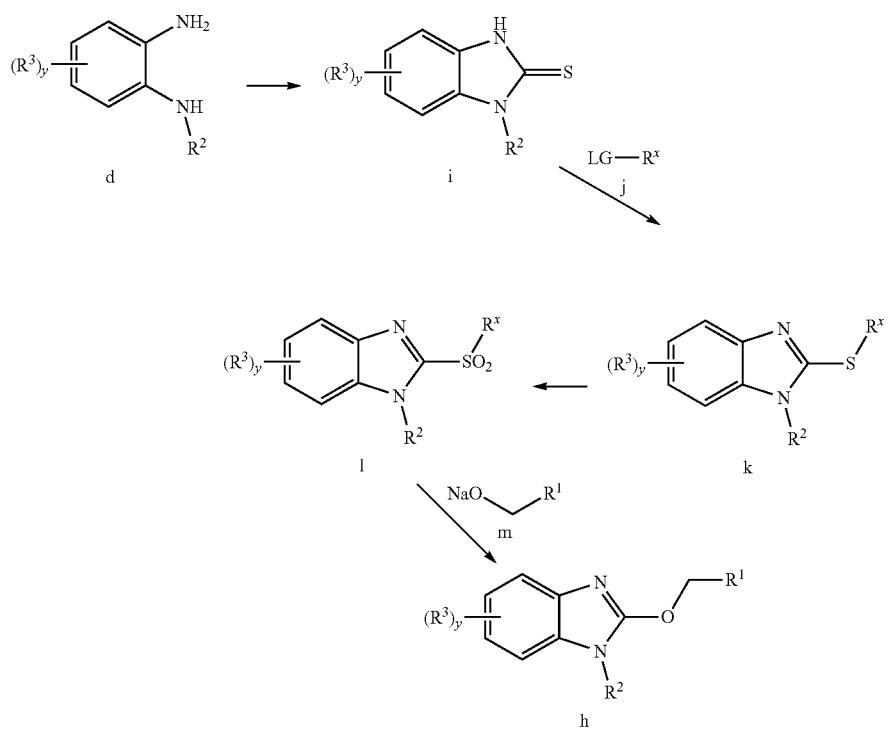

Alternatively certain compounds of the invention can be made starting from diamines d. Compounds of formula i can be formed (e.g. by treating with TCDI in THF). Reaction with an electrophile j (in which LG is a leaving group, for example OTf, Cl, Br, I and $R^x$ can be any convenient group) provides compounds of formula k. Treatment with mCPBA (e.g. in DCM at room temperature) can give sulfones of formula I. Reaction with a sodium alkoxide m (e.g. in DMF at room temperature) provides compounds of formula h, a subset of compounds of the invention (Scheme B).

Scheme C

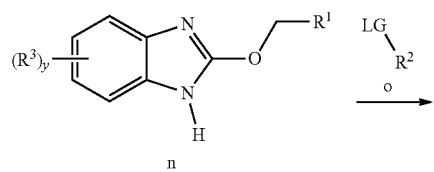

-continued

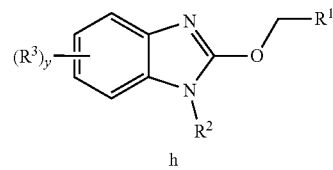

Alternatively, treatment of compounds of formula n with a heterocycle of formula o (in which LG is a leaving group such as F, Cl, Br, OTf, $SO_2R^x$) (e.g. in the presence of a base such as NaH in a suitable solvent such as DMF at a temperature of 100° C.) provides compounds of formula h, a subset of compounds of the invention (Scheme C).

Scheme D

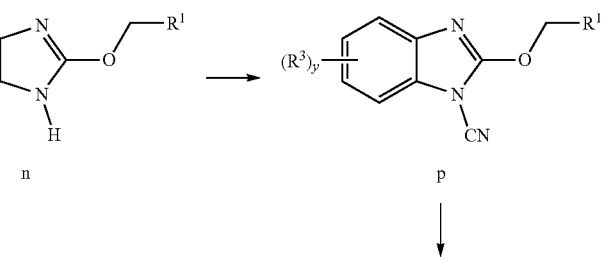

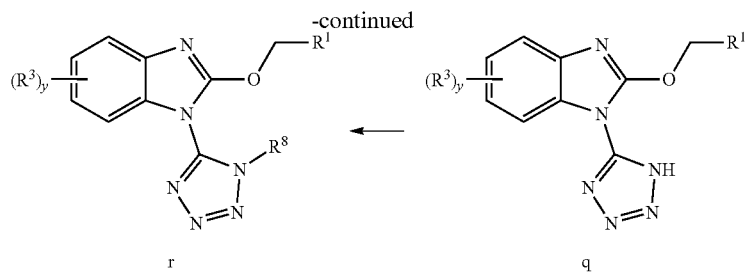

As a further alternative, treatment of compounds of formula n with cyanogen bromide (e.g. in acetone at 0° C.) can form compounds of formula p. Reaction with ammonium chloride followed by sodium azide (e.g. in DMF at room temperature) provides tetrazoles of formula q. Alkylation with $R^8$-LG (where LG is a leaving group such as Cl, Br, I, OTf) (e.g. in the presence of a base such as $K_2CO_3$ in a solvent such as DMF at 40° C.) provides compounds of formula r, a subset of compounds of the invention (Scheme D).

Scheme E

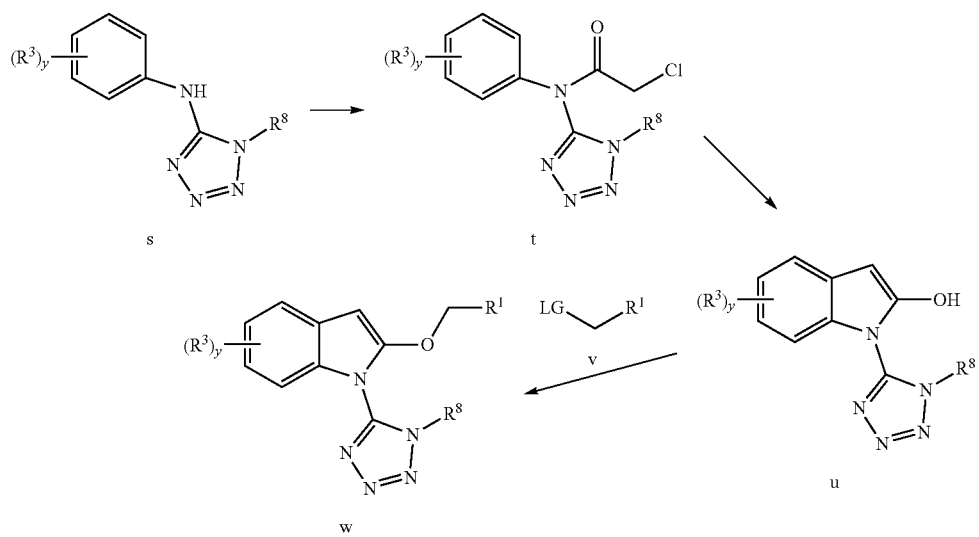

Certain compounds of the invention can be made starting from compounds of formula s by reaction with chloroacetyl chloride (e.g. in the presence of triethylamine in DCM at room temperature) to give compounds of formula t. Treatment with aluminium trichloride (e.g. in the presence of NaCl at 120° C.) can provide compounds of formula u. Reaction with an electrophile v (where LG is a leaving group such as Cl, Br, I, OTf) (e.g. with $Cs_2CO_3$ in DMF at room temperature) provides compounds of formula w, a subset of compounds of the invention (Scheme E).

Scheme F

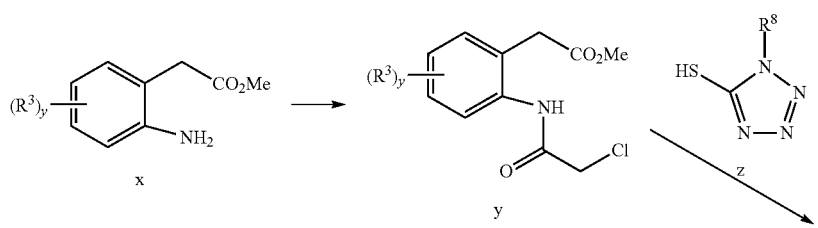

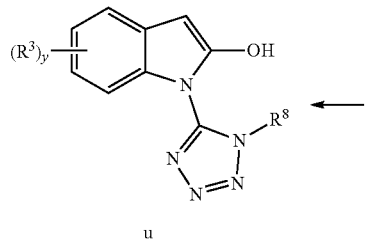 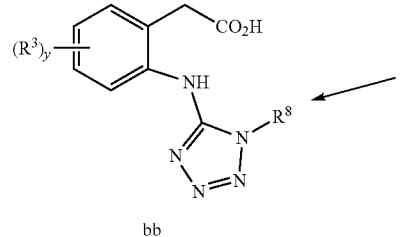 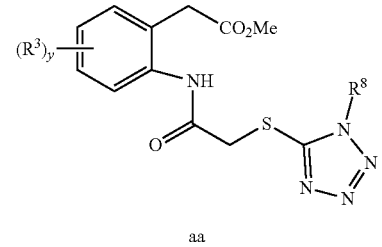

u  bb  aa

Certain compounds of the invention can be made starting from compounds of formula x by reaction with chloroacetyl chloride (e.g. in the presence of triethylamine in DCM at room temperature) to give amides of formula y. Reaction with a thioltetrazole of formula z (e.g. with KOH in MeOH at room temperature) can provide compounds of formula aa. Treatment first with mCPBA (e.g. in DCM at room temperature) followed by reaction with potassium hydroxide (e.g. in ethanol at reflux overnight) can give compounds of formula bb. An amide forming reaction (e.g. with HCl in water at 50° C.) provides compounds of formula u (Scheme F). Reaction of compounds of formula u as in Scheme E provides compounds of formula w, a subset of compounds of the invention.

Analytical Procedures

Flash chromatography was carried out using a Biotage Isolera 4, with Biotage® SNAP KP-Sil cartridges, packed with 50 µm silica particles with a surface area of 500 m²/g, or alternative cartridges (e.g. Puriflash, produced by Interchim; Claricep, produced by Agela Technologies) where stated. Visualisation was carried out with UV light (254 nm) and by staining with either potassium permanganate, phosphomolybdic acid (PMA) or ninhydrin solutions.

All $^1$H NMR spectra were obtained on a Bruker AVIII 400 with 5 mm QNP or Bruker AVI 500 with 5 mm QNP or Bruker DPX 300. Chemical shifts are expressed in parts per million (δ) and are referenced to the solvent. Coupling constants J are expressed in Hertz (Hz).

MS was carried out on a Waters Alliance ZQ MS (methods A-D) or on a Waters Acquity UPLC-QDA UV-MS (methods E-F), using one of the methods below:

Method a (5 Minute Basic pH)

Column: YMC-Triart C18 50 × 2 mm, 5 µm. Flow rate: 0.8 mL/min.
Injection volume: 5 µL.
Mobile Phase  A  H$_2$O
  B  CH$_3$CN
  C  50% H$_2$O/50% CH$_3$CN + 1.0% ammonia (35% aq.)

| Time (min) | A (%) | B (%) | C (%) |
|---|---|---|---|
| 0 | 95 | 0 | 5 |
| 4 | 0 | 95 | 5 |
| 4.4 | 0 | 95 | 5 |
| 4.5 | 95 | 5 | 0 |
| 4.5 | | STOP | |

Method B (5 Minute Acidic pH)

Column: YMC-Triart C18 50 × 2 mm, 5 µm. Flow rate: 0.8 mL/min.
Injection volume: 5 µL.
Mobile Phase  A  H$_2$O
  B  CH$_3$CN
  C  50% H$_2$O/50% CH$_3$CN + 1.0% formic acid

| Time (min) | A (%) | B (%) | C (%) |
|---|---|---|---|
| 0 | 95 | 0 | 5 |
| 4 | 0 | 95 | 5 |
| 4.4 | 0 | 95 | 5 |
| 4.5 | 95 | 5 | 0 |
| 4.5 | | STOP | |

Method D (15 minute acidic pH)

Column YMC Triart-C18 50 × 2 mm, 5 µm Flow rate: 0.8 mL/min.
Injection volume: 5 µL
Mobile Phase  A  H$_2$O
  B  CH$_3$CN
  C  50% H$_2$O/50% CH$_3$CN + 1.0% formic acid

| Time (min) | A (%) | B (%) | C (%) |
|---|---|---|---|
| 0 | 95 | 0 | 5 |
| 2.0 | 95 | 0 | 5 |
| 12.0 | 0 | 95 | 5 |
| 14.0 | 0 | 95 | 5 |
| 14.2 | 95 | 0 | 5 |

Method E (3.5 Minute Basic pH)

Mobile phases: Water (A)/Acetonitrile (B) both with 0.1% (v/v) Ammonia

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |
| 3.1 | 98 | 2 | 1.0 |
| 3.5 | 98 | 2 | 1.0 |

Column: BEH C18 2.1 × 50 mm, 1.7 µm @ 50° C.

Method F (3.5 minute acidic pH)

Mobile phases: Water (A)/Acetonitrile (B) both with 0.1% (v/v) Formic Acid

| Time | % A | % B | Flow rate (mL/min) |
|---|---|---|---|
| Initial | 98 | 2 | 1.0 |
| 0.2 | 98 | 2 | 1.0 |
| 2.5 | 2 | 98 | 1.0 |
| 3.0 | 2 | 98 | 1.0 |

| Time | % A | % B | Flow rate (mL/min) |
|------|-----|-----|--------------------|
| 3.1 | 98 | 2 | 1.0 |
| 3.5 | 98 | 2 | 1.0 |

Column: CSH C18 2.1 × 50 mm, 1.7 μm @ 50° C.

All reagents were obtained from commercial suppliers and used as supplied unless otherwise stated.

All examples are named using ChemBioDraw Ultra 14.0.

Reactions were conducted at ambient temperature (RT) unless otherwise stated.

Synthetic Intermediates

1-Methyl-N-(2-nitrophenyl)-1H-tetrazol-5-amine A

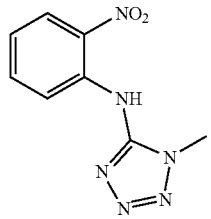 [SMILES: Cn1nnnc1Nc1ccccc1[N+](=O)[O-]]

A stirred, ice-cooled suspension of 5-amino-1-methyltetrazole (6.09 g, 61.5 mmol) in dry DMF (50 mL) was treated with sodium hydride (5.04 g, 126 mmol) and stirred a further 10 min then 1-fluoro-2-nitrobenzene (6.48 ml, 61.5 mmol) was added dropwise over ca. 25 min so as to maintain the internal temp around 15-20° C. The cooling bath was then removed and the dark red solution was stirred whilst warming to RT over 1 h then diluted cautiously with water (250 mL) and washed with $Et_2O$ (250 mL). The aq. layer was acidified with 5M aq. HCl (22 mL). The solid was collected, washed with water (ca. 3×20 mL) and dried in vacuo to give 1-methyl-N-(2-nitrophenyl)-1H-tetrazol-5-amine A (11.7 g, 86%), as a yellow solid.

$^1$H NMR (500 MHz, $CDCl_3$) δ 10.59 (s, 1H), 8.76 (dd, J=8.6, 1.2 Hz, 1H), 8.32 (dd, J=8.5, 1.5 Hz, 1H), 7.75 (s, 1H), 7.17 (s, 1H), 4.06 (s, 3H); LCMS (method B): 2.21 min (221, $MH^+$).

Following the same procedure as for Synthetic Intermediate ("Int.") A, substituting 1-fluoro-2-nitrobenzene and/or 5-amino-1-methyltetrazole with the required o-fluoronitrobenzene (optionally substituted with $(R^3)_y$) and/or aminoheterocycle ($R^2$—$NH_2$), and using an extractive work-up (EtOAc) where a solid was not obtained upon acidification, followed by chromatography on silica if necessary, there were thus obtained the following intermediates:

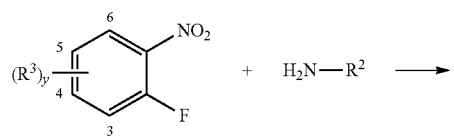

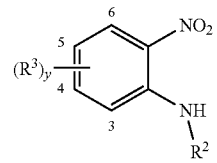

| Int. | $(R^3)_y$ | $R^2$—NH2 | Yield | RT[a] | $MH^+$ |
|------|-----------|-----------|-------|-------|--------|
| A1 | 4-F | 5-amino-1-methyltetrazole | 57% | 2.32 (B) | 239.1 |
| A2 | y = 0 | 2-amino-3-methylpyridine | 53% | 3.16 (B) | 230.1 |
| A3 | y = 0 | 2-aminopyridine | 94%[b] | 2.57(B) | 216.1 |
| A4 | 4-Br | 5-amino-1-methyltetrazole | 80% | 2.70 (A) | 299.1 |
| A5 | 6-Cl | 5-amino-1-methyltetrazole | 97% | 2.45 (B) | 255.1 |

[a]RT = LCMS retention time in minutes using indicated method (A-F);
[b] Product obtained using an aqueous work-up, extracting with EtOAc, followed by chromatography on silica eluting with 0-50% EtOAc/PE.

$N^1$-(1-Methyl-1H-tetrazol-5-yl)benzene-1,2-diamine B

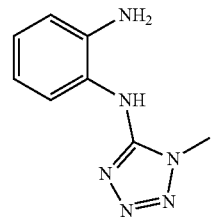

A stirred suspension of 1-methyl-N-(2-nitrophenyl)-1H-tetrazol-5-amine A (11.1 g, 50.4 mmol) in ethanol (400 ml) under nitrogen was treated with 10% palladium on activated charcoal (0.4 g) then ammonium formate (12.7 g, 201 mmol) and the mixture was heated under reflux for 3.5 h. The mixture was cooled slightly and filtered through Celite whilst still warm. The filter was washed with EtOAc and the filtrates were evaporated to dryness to give crude aniline, $N^1$-(1-methyl-1H-tetrazol-5-yl)benzene-1,2-diamine B (9.95 g, 100% yield) as a maroon solid, used directly in the next step.

$^1$H NMR (500 MHz, DMSO) δ 8.15 (br s, 1H), 7.19 (dd, J=7.8, 1.5 Hz, 1H), 6.96-6.89 (m, 1H), 6.74 (dd, J=8.0, 1.4 Hz, 1H), 6.56 (td, J=7.7, 1.5 Hz, 1H), 5.05 (s, 2H), 3.84 (s, 3H); LCMS (method A): 1.38 min (191, $MH^+$).

Following the same procedure as for Synthetic Intermediate ("Int.") B, substituting the nitroaryl starting material ("SM") A with the required nitroaryl, there were thus obtained the following aniline intermediates:

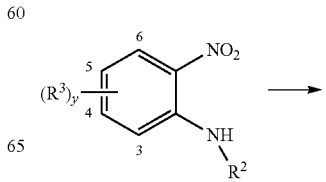

-continued

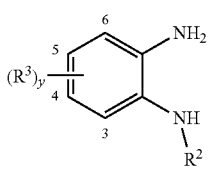

| SM | $(R^3)_y$ | $R^2$ | Aniline | Yield | $RT^a$ | $MH^+$ |
|---|---|---|---|---|---|---|
| A1 | 4-F | 1-methyltetrazol-5-yl | B1 | 100% | 1.12(B) | 209.1 |
| A2 | y = 0 | 2-(3-methyl)pyridyl | B2 | 100% | 0.94(B) | 200.1 |
| A3 | y = 0 | 2-pyridyl | B3 | 100% | 0.96(B) | 186.2 |

$^a$RT = LCMS retention time in minutes using indicated method (A-F).

5-Bromo-M-(1-methyl-1H-tetrazol-5-yl)benzene-1,2-diamine B4

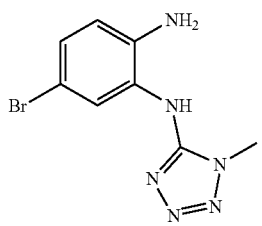

A mixture of potassium carbonate (1.39 g, 10.0 mmol) and sodium hydrosulfite (1.75 g, 10.0 mmol) in water (6 mL) was added dropwise to a mixture of N-(5-bromo-2-nitrophenyl)-1-methyl-1H-tetrazol-5-amine (500 mg, 1.67 mmol) and 1,1'-di-n-octyl-4,4'-bipyridinium dibromide (32 mg, 0.084 mmol) in 1,2-dichloroethane (48 mL). The mixture was stirred at 60° C. for 40 h. THF (10 mL) was added and the mixture was stirred at 60° C. for a further 24 h. Water (50 mL) was added and the mixture was neutralised with citric acid and extracted into DCM (2×50 mL). The combined organics were washed with brine, dried (MgSO$_4$) and chromatographed on silica (25 g Puriflash cartridge) eluting with 0-10% MeOH/DCM to give 5-bromo-N$^1$-(1-methyl-1H-tetrazol-5-yl)benzene-1,2-diamine B4 (432 mg, 96%) as an orange solid.

$^1$H NMR (500 MHz, CDCl$_3$) δ 7.27 (d, J=9.4 Hz, 1H), 7.08 (d, J=8.0 Hz, 1H), 6.66 (d, J=8.4 Hz, 1H), 3.74 (s, 3H); LCMS (method B): 1.79 min (271.1, MH$^+$).

3-Chloro-M-(1-methyl-1H-tetrazol-5-yl)benzene-1,2-diamine B5

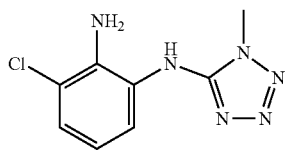

A solution of N-(3-chloro-2-nitrophenyl)-1-methyl-1H-tetrazol-5-amine A5 (2.00 g, 7.85 mmol) in MeOH (150 mL) was treated with water (50 ml), iron powder (1.76 g, 32 mmol) and ammonium chloride (2.5 g, 47 mmol) then heated under reflux for 20 h. The mixture was cooled, filtered through Celite (and the filter washed with MeOH) and concentrated. The solid was partitioned between EtOAc (100 mL; not fully soluble) and water (100 mL) and the organics washed further with water (100 mL) and brine then dried (MgSO$_4$) to give a maroon solid (0.98 g). Residual solid left in the separatory funnel after decantation of EtOAc solution was dissolved in ca. 20% MeOH/DCM, dried (MgSO$_4$) and concentrated to give an off-white solid (0.74 g). Combined this gave 3-chloro-N$^1$-(1-methyl-1H-tetrazol-5-yl)benzene-1,2-diamine B5 (1.72 g, 97%); both samples identical by NMR.

$^1$H NMR (500 MHz, DMSO) δ 8.37 (s, 1H), 7.19 (dd, J=7.9, 1.4 Hz, 1H), 7.12 (dd, J=8.0, 1.4 Hz, 1H), 6.58 (t, J=8.0 Hz, 1H), 5.27 (s, 2H), 3.86 (s, 3H); LCMS (method A): 1.86 min (225.1, MH$^+$).

In a subsequent experiment the extractive work-up was replaced with a simpler procedure: the partially concentrated filtrates, essentially free from MeOH, were filtered and the solid washed with water and dried to give B5 in 90% yield, containing traces of iron salts (NMR signals broadened) but pure enough for the next step.

1-(1-Methyl-1H-tetrazol-5-yl)-1,3-dihydro-2H-benzo[d]imidazole-2-thione C

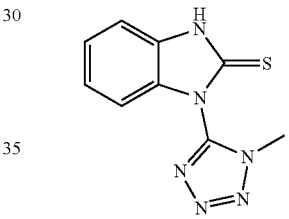

A suspension of N$^1$-(1-methyl-1H-tetrazol-5-yl)benzene-1,2-diamine B (923 mg, 4.85 mmol) in dry THF (25 ml) was treated with TCDI (1.30 g, 7.29 mmol), stirred under nitrogen at room temperature for 75 min. then diluted with water (100 mL) and cooled with ice/water. The solid was collected, washed with water and dried in vacuo to give 1-(1-methyl-1H-tetrazol-5-yl)-1,3-dihydro-2H-benzo[d]imidazole-2-thione C (962 mg, 85%) as a pale pink solid.

$^1$H NMR (500 MHz, DMSO) δ 13.66 (s, 1H), 7.36-7.29 (m, 2H), 7.29-7.20 (m, 1H), 7.10 (d, J=8.0 Hz, 1H), 4.08 (s, 3H); LCMS (method B): 1.96 min (233.1, MH$^+$).

Following the same procedure as for Synthetic Intermediate C, with the appropriate aniline starting material in place of N$^1$-(1-methyl-1H-tetrazol-5-yl)benzene-1,2-diamine B, except that an extractive work-up followed by chromatography on silica was carried out if a solid was not obtained upon dilution with water, there were thus obtained the following intermediates:

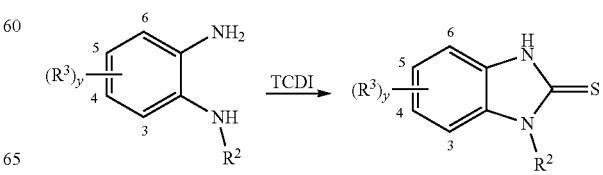

| Int. | $(R^3)_y$ | $R^2$ | SM | Yield | $RT^a$ | $MH^+$ |
|---|---|---|---|---|---|---|
| C1 | 4-F | 1-methyltetrazol-5-yl- | B1 | 55%[b] | 2.13 (B) | 251.1 |
| C2 | y = 0 | 2-(3-methyl)pyridyl | B2 | 76% | 2.01 (B) | 242.2 |
| C3 | y = 0 | 2-pyridyl | B3 | 47%[b] | 1.99 (B) | 228.1 |
| C5 | 6-Cl | 1-methyltetrazol-5-yl- | B5 | 58%[b,c] | 1.45 (F) | 267.0 |

[a]RT = LCMS retention time in minutes using indicated method (A-F);
[b]Extractive work-up followed by chromatography;
[c]DMF added as co-solvent and heated to 70° C. for 68 h.

6-Bromo-1-(1-methyl-1H-tetrazol-5-yl)-1,3-dihydro-2H-benzo[d]imidazole-2-thione C4

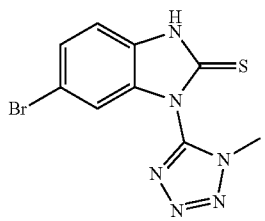 [SMILES: Cn1nnnc1-n1c(=S)[nH]c2ccc(Br)cc21]

Ethylxanthic acid potassium salt (953 mg, 5.91 mmol) was added to a solution of 5-bromo-$N^1$-(1-methyl-1H-tetrazol-5-yl)benzene-1,2-diamine B4 (530 mg, 1.97 mmol) in EtOH (8 mL) and water (0.4 mL) and the mixture was heated under reflux for 60 h then diluted with water, quenched with saturated aqueous ammonium chloride solution and extracted with EtOAc (2×100 mL). The organic layers were combined, washed with water (3×20 mL) and brine, dried (MgSO$_4$) and concentrated in vacuo to give 6-bromo-1-(1-methyl-1H-tetrazol-5-yl)-1,3-dihydro-2H-benzo[d]imidazole-2-thione C$_4$ (493 mg, 80%) as a pink solid.

$^1$H NMR (500 MHz, CDCl$_3$) δ 7.21 (dd, J=8.5, 1.7 Hz, 1H), 6.97-6.95 (m, 1H), 6.94 (s, 1H), 3.95 (s, 3H); LCMS (method B): 2.52 min (313.0, MH$^+$).

1-(1-Methyl-1H-tetrazol-5-yl)-2-(methylthio)-1H-benzo[d]imidazole D

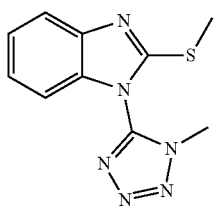 [SMILES: CSc1nc2ccccc2n1-c1nnnn1C]

A solution of 1-(1-methyl-1H-tetrazol-5-yl)-1,3-dihydro-2H-benzo[d]imidazole-2-thione C (373 mg, 1.61 mmol) in dry DMF (3 mL) was treated with iodomethane (0.113 mL, 1.82 mmol) then caesium carbonate (740 mg, 2.27 mmol) and the mixture was stirred at ambient temperature under nitrogen for 40 min. The solution was diluted with water (20 mL) and extracted with EtOAc (25 mL). The organics were washed further with water (2×25 mL) and brine, dried (MgSO$_4$) and chromatographed on silica (25 g Biotage KP-Sil cartridge) eluting with 0-1% MeOH/DCM to give 1-(1-methyl-1H-tetrazol-5-yl)-2-(methylthio)-1H-benzo[d]imidazole D (341 mg, 86%) as a red solid, essentially pure by NMR.

$^1$H NMR (500 MHz, CDCl$_3$) δ 7.75 (d, J=8.0 Hz, 1H), 7.39-7.32 (m, 1H), 7.30-7.21 (m, 1H), 7.04 (d, J=8.0 Hz, 1H), 3.98 (s, 3H), 2.81 (s, 3H); LCMS (method B) 2.35 min (247.1, MH$^+$)

Following the same procedure as for Synthetic Intermediate D, with the appropriate starting material in place of 1-(1-methyl-1H-tetrazol-5-yl)-1,3-dihydro-2H-benzo[d]imidazole-2-thione C, there were thus obtained the following intermediates:

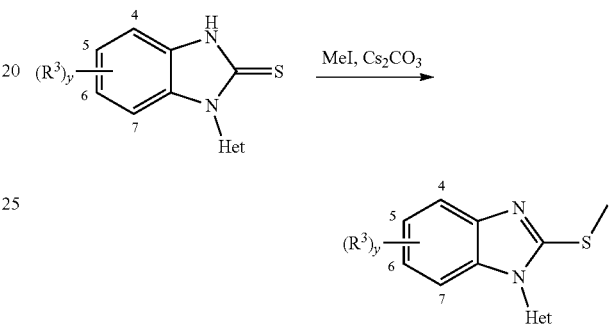

| Int. | $(R^3)_y$ | Het- | SM | Yield | $RT^a$ | $MH^+$ |
|---|---|---|---|---|---|---|
| D1 | 6-F | 1-methyltetrazol-5-yl- | C1 | 59%[b] | 2.36 (B) | 265.1 |
| D2 | y = 0 | 2-(3-methyl)pyridyl- | C2 | 68%[b] | 2.33 (B) | 256.2 |
| D3 | y = 0 | 2-pyridyl- | C3 | 70%[b,c] | 2.35 (B) | 242.2 |
| D4 | 6-Br | 1-methyltetrazol-5-yl- | C4 | 67%[d] | 2.62 (B) | 325.0 |
| D5 | 4-Cl | 1-methyltetrazol-5-yl- | C5 | 50%[b] | 2.90 (B) | 281.2 |

[a]RT = LCMS retention time in minutes using indicated method (A-F);
[b]Eluent for chromatography was 0-100% EtOAc/PE;
[c]Contains DMF but used directly in next step;
[d]No chromatographic purification required.

Alternatively Intermediate D was prepared from Intermediate B in a one-pot cyclisation-alkylation procedure:

A solution of $N^1$-(1-methyl-1H-tetrazol-5-yl)benzene-1,2-diamine B (9.98 g, 52.5 mmol) in DMF (100 ml) was treated with thiocarbonyldiimidazole (10.6 g, 59.5 mmol) and stirred at RT under nitrogen for 1 h. The solution was cooled with ice-water and caesium carbonate (22.2 g, 68.2 mmol) was then added. After another 10 min iodomethane (4.08 ml, 65.6 mmol) was added cautiously. The cooling bath was removed and stirring was continued for 35 min. Water (250 mL) was added and the mixture was stirred for 15 min then diluted with EtOAc (750 mL). The organics were washed with water (3×750 mL) and brine and aq. were back-extracted with EtOAc (750 mL). Organics were combined, dried (MgSO$_4$) and concentrated to give crude product, 12.6 g, as a red solid. Chromatography on silica (220 g Puriflash column) eluting with 40-60% EtOAc/PE gave 1-(1-methyl-1H-tetrazol-5-yl)-2-(methylthio)-1H-benzo[d]imidazole D (11.2 g, 86%) as an off-white solid.

1-(5-Chloropyrimidin-4-yl)-2-(methylthio)-1H-benzo[d]imidazole D6

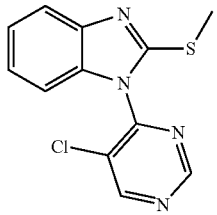 [SMILES: CSc1nc2ccccc2n1-c1ncncc1Cl]

A stirred solution of 4,5-dichloropyrimidine (206 mg, 1.38 mmol) and 2-methylthiobenzimidazole (227 mg, 1.38 mmol) in dry DMF (1.5 mL) was treated with potassium tert-butoxide (155 mg, 1.38 mmol) to give an orange solution which was then heated to 50° C. for 8 h. The solution was cooled, quenched with saturated aqueous ammonium chloride solution (to pH 6-7), diluted with water (30 mL) and extracted with EtOAc (40 mL). The organics were washed with water (2×30 mL) and brine then combined, dried (MgSO$_4$), triturated with DCM and the liquors were chromatographed eluting with 20-50% EtOAc/PE to give 1-(5-chloropyrimidin-4-yl)-2-(methylthio)-1H-benzo[d]imidazole D6 (193 mg, 50%) as a colourless gum.

$^1$H NMR (500 MHz, CDCl$_3$) δ 9.20 (s, 1H), 9.01 (s, 1H), 7.78-7.71 (m, 1H), 7.30 (ddd, J=8.1, 7.4, 1.1 Hz, 1H), 7.22 (ddd, J=8.4, 7.4, 1.1 Hz, 1H), 7.08-7.01 (m, 1H), 2.79 (s, 3H); LCMS (method B): 2.58 min (277.0, MH$^+$).

1-(1-Methyl-1H-tetrazol-5-yl)-2-(methylsulfonyl)-1H-benzo[d]imidazole E

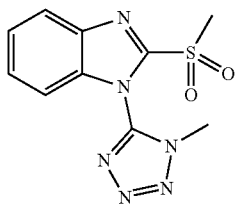 [SMILES: Cn1nnnc1-n1c(S(C)(=O)=O)nc2ccccc21]

An ice-cooled solution of 1-(1-methyl-H-tetrazol-5-yl)-2-(methylthio)-1H-benzo[d]imidazole D (4.55 g, 18.5 mmol) in DCM (100 mL) was treated with 75% m-chloroperbenzoic acid (10.6 g, 46.2 mmol), stirred for 10 min then cooling was removed. After a further 4 h the mixture was filtered and the solid washed with a little DCM. The filtrates were combined, washed with saturated aqueous sodium hydrogen carbonate solution (2×100 mL) and brine and the aq. back-extracted with DCM (100 mL). The organic extracts were combined, dried (MgSO$_4$) and chromatographed on silica (80 g Claricep cartridge) eluting with 25-50% EtOAc/PE to give 1-(1-methyl-1H-tetrazol-5-yl)-2-(methylsulfonyl)-1H-benzo[d]imidazole E (4.39 g, 85%) as a white solid.

Following the same procedure as for Synthetic Intermediate E, with the appropriate starting material in place of 1-(1-methyl-H-tetrazol-5-yl)-2-(methylthio)-1H-benzo[d]imidazole D, there were thus obtained the following intermediates:

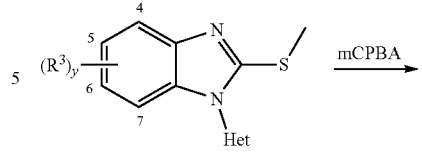

| Int. | (R$^3$)$_y$ | Het- | SM | Yield | RT$^a$ | MH$^+$ |
|---|---|---|---|---|---|---|
| E1 | 6-F | 1-methyltetrazol-5-yl- | D1 | 76% | 2.25 (B) | 297.1 |
| E2 | y = 0 | 3-(2-methyl)pyridyl | D2 | 77% | 2.18 (B) | 288.1 |
| E3 | y = 0 | 2-pyridyl- | D3 | 71% | 2.13 (B) | 274.2 |
| E4 | 6-Br | 1-methyltetrazol-5-yl- | D4 | 49% | 2.62 (B) | 356.9 |
| E5 | 4-Cl | 1-methyltetrazol-5-yl- | D5 | 79% | 2.71 (B) | 313.1 |
| E6 | y = 0 | 5-chloro-pyrimidin-4-yl- | D6 | 83% | 2.33 (B) | 309.1 |

$^a$RT = LCMS retention time in minutes using indicated method (A-F).

1-(5-Chloropyrimidin-4-yl)-2-(phenylthio)-1H-benzo[d]imidazole F

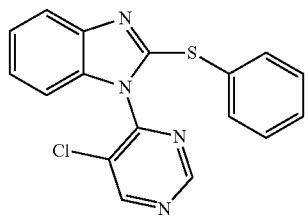 [SMILES: Clc1cncnc1-n1c(Sc2ccccc2)nc2ccccc21]

A solution of 1-(5-chloropyrimidin-4-yl)-2-(methylsulfonyl)-1H-benzo[d]imidazole E6 (49.5 mg, 0.16 mmol) in dry DMF (1 mL) was treated with 90% sodium thiophenolate (24 mg, 0.16 mmol) and stirred at RT for 90 min then was diluted with EtOAc (20 mL), washed with water (3×20 mL) and brine, dried (MgSO$_4$) and chromatographed on silica (12 g Puriflash cartridge) eluting with 20-50% EtOAc/PE to give 1-(5-chloropyrimidin-4-yl)-2-(phenylthio)-1H-benzo[d]imidazole F (43 mg, 79%) as a colourless gum.

$^1$H NMR (500 MHz, CDCl$_3$) δ 9.14 (s, 1H), 8.91 (s, 1H), 7.80 (d, J=7.9 Hz, 1H), 7.41-7.18 (m, 7H), 7.06 (d, J=8.0 Hz, 1H); LCMS (Method B): 2.9 min (339.1 and 341.0, MH$^+$).

Following the same procedure as for Synthetic Intermediate F, with the appropriate starting material in place of 1-(5-chloropyrimidin-4-yl)-2-(methylsulfonyl)-1H-benzo[d]imidazole E6, there was thus obtained the following intermediate Int. F1:

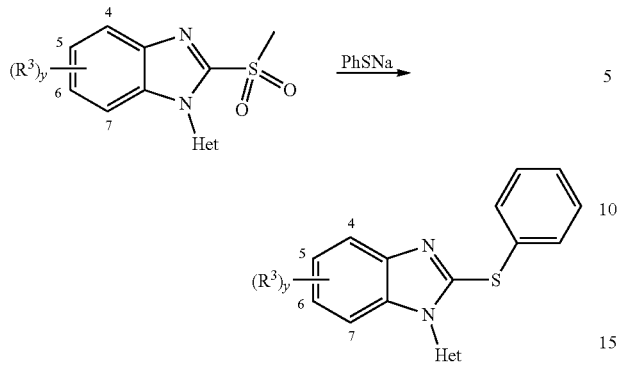

| Int. | $(R^3)_y$ | Het- | SM | Yield | RT$^a$ | MH$^+$ |
|---|---|---|---|---|---|---|
| F1 | y = 0 | 1-methyltetrazol-5-yl- | E | 97% | 2.77 (B) | 309.1 |

$^a$RT = LCMS retention time in minutes using indicated method (A-F)

Alternatively Intermediate F may be prepared as follows:

A stirred solution of 2-(phenylthio)-1H-benzo[d]imidazole (378 mg, 1.67 mmol, one-step preparation described in Tetrahedron, 2006, 62, 4306) in dry DMF (2 mL) was treated with a 60% mineral oil dispersion of sodium hydride (75 mg, 1.9 mmol) then after 5 min with a solution of 4,5-dichloropyrimidine (274 mg, 1.84 mmol) in dry DMF (2 mL) then was heated to 75° C. for 2 h. The mixture was cooled, quenched with saturated aqueous ammonium chloride solution (1 mL, to pH 7-8), extracted with EtOAc (50 mL), washed with water (3×50 mL) and brine and dried (MgSO$_4$). Chromatography on silica (12 g Claricep cartridge) eluting with 0.5-1% MeOH/DCM gave 1-(5-chloropyrimidin-4-yl)-2-(phenylthio)-1H-benzo[d]imidazole F (420 mg, 74%), as a white solid.

Following the same procedure as for Synthetic Intermediate E, with the appropriate PhS-substituted starting material in place of 1-(1-methyl-1H-tetrazol-5-yl)-2-(methylthio)-1H-benzo[d]imidazole D, there were thus obtained the following PhSO$_2$-substituted intermediates Int. G-G1:

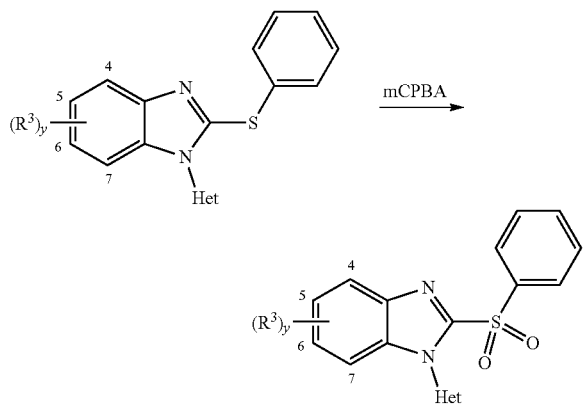

| Int. | $(R^3)_y$ | Het- | SM | Yield | RT$^a$ | MH$^+$ |
|---|---|---|---|---|---|---|
| G | y = 0 | 5-chloropyrimidin-4-yl | F | 79% | 2.77 (B) | 371.1 |
| G1$^b$ | y = 0 | 1-methyltetrazol-5-yl- | F1 | 77% | 2.77 (B) | 341.1 |

$^a$RT = LCMS retention time in minutes using indicated method (A-F).
$^b$Initial reaction time was 18 h then more mCPBA (0.4 equiv.) was added for another 5 h reaction time.

1-(1-Methyl-1H-pyrazol-5-yl)-1H-benzo[d]imidazole H

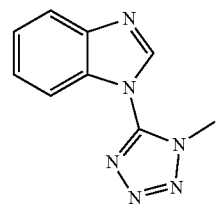

A suspension of $N^1$-(1-methyl-1H-tetrazol-5-yl)benzene-1,2-diamine B (1.72 g, 9.04 mmol) in trimethylorthoformate (15 ml, 137 mmol) was treated with conc. hydrochloric acid (0.04 ml, 0.5 mmol) and stirred with heating under reflux for 60 min, cooled, then evaporated to dryness to give a red solid. Chromatography on silica (25 g Biotage Snap Ultra column) eluting with 40-80% EtOAc/PE gave 1-(1-methyl-1H-tetrazol-5-yl)-1H-benzo[d]imidazole H (1.43 g, 79%) as a pale pink solid.

$^1$H NMR (500 MHz, CDCl$_3$) δ 8.27 (s, 1H), 7.97-7.92 (m, 1H), 7.63-7.57 (m, 1H), 7.48 (ddd, J=4.7, 2.1, 0.9 Hz, 2H), 4.17 (s, 3H); LCMS (method B): 1.67 min (201.1, MH$^+$).

2-Bromo-1-(1-methyl-1H-tetrazol-5-yl)-1H-benzo[d]imidazole I

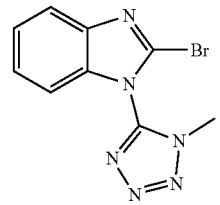 [SMILES: Cn1nnnc1-n1c(Br)nc2ccccc21]

A solution of 1-(1-methyl-1H-tetrazol-5-yl)-1H-benzo[d]imidazole H (0.131 g, 0.654 mmol) in dry DMF (4 ml) was treated with N-Bromosuccinimide (0.40 g, 2.2 mmol) and stirred under nitrogen at 90° C. for 55 min. The mixture was diluted with EtOAc (20 mL), washed with water (3×20 mL) and brine, dried (MgSO$_4$) and chromatographed on silica (12 g Puriflash column) eluting with 12-100% EtOAc/PE to give 2-bromo-1-(1-methyl-1H-tetrazol-5-yl)-1H-benzo[d]imidazole I (0.208 g, 60%) as a pale pink solid.

$^1$H NMR (500 MHz, CDCl$_3$) δ 7.85-7.81 (m, 1H), 7.40 (dtd, J=16.7, 7.5, 1.2 Hz, 2H), 7.12-7.09 (m, 1H), 4.02 (s, 3H); LCMS (method A): 2.37 min (281.0, MH$^+$).

N-(6-(((1-(1-Methyl-1H-tetrazol-5-yl)-1H-benzo[d]imidazol-2-yl)oxy)methyl)pyridin-2-yl)-N-(methylsulfonyl)methanesulfonamide J

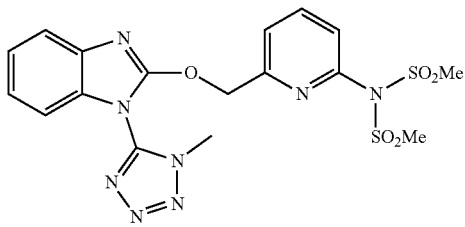 [SMILES: Cn1nnnc1-n1c(OCc2cccc(N(S(C)(=O)=O)S(C)(=O)=O)n2)nc2ccccc21]

Methanesulfonyl chloride (0.026 mL, 0.34 mmol) was added to a stirred solution of 6-(((1-(1-methyl-1H-tetrazol-5-yl)-1H-benzo[d]imidazol-2-yl)oxy)methyl)pyridin-2-amine 1 (50 mg, 0.16 mmol) and triethylamine (0.050 mL, 0.34 mmol) in DCM (2 mL) at 0° C. The reaction mixture was allowed to warm to room temperature over 16 h then was evaporated directly onto silica and chromatographed on silica (10 g Biotage KP-sil cartridge) eluting with 50-100% EtOAc/PE to give N-(6-(((1-(1-methyl-H-tetrazol-5-yl)-1H-benzo[d]imidazol-2-yl)oxy)methyl)pyridin-2-yl)-N-(methylsulfonyl)methanesulfonamide J (61 mg, 82%) as a white solid.

$^1$H NMR (500 MHz, CDCl$_3$) δ 7.93 (t, J=7.8 Hz, 1H), 7.58 (t, J=7.2 Hz, 2H), 7.36-7.23 (m, 4H), 5.76 (s, 2H), 4.02 (s, 3H), 3.45 (s, 6H). LCMS (method A): 2.59 min (479.0, MH$^+$).

3-(5-Chloropyrimidin-4-yl)indolin-2-one K

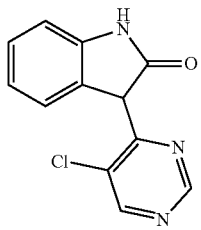 [SMILES: O=C1Nc2ccccc2C1c1ncncc1Cl]

An ice-cooled suspension of 60% sodium hydride (118 mg, 2.95 mmol) in mineral oil in dry DMF (2 mL) was treated with 2-oxindole (190 mg, 1.43 mmol) and stirred under N$_2$ for 5 min to give an orange solution then 4,5-dichloropyrimidine (204 mg, 1.37 mmol) was added in dry DMF (1 mL). After 20 min. the mixture was quenched with saturated aq. NH$_4$Cl solution to pH 7. The product was extracted into EtOAc (50 mL) and the organics were washed with water (3×50 mL) and brine then dried (MgSO$_4$), loaded onto silica (2 g) and chromatographed on silica (12 g Claricep i-Series cartridge) eluting with 1.5-5% MeOH/DCM. Trituration with DCM gave 3-(5-chloropyrimidin-4-yl)indolin-2-one K (183 mg, 54%) as a solid.

$^1$H NMR (500 MHz, CDCl$_3$) δ 9.02 (s, 1H), 8.76 (s, 1H), 8.20 (s, 1H), 7.28 (ddd, J=7.8, 4.4, 3.4 Hz, 1H), 7.10 (d, J=7.5 Hz, 1H), 7.01 (td, J=7.6, 0.9 Hz, 1H), 6.96 (d, J=7.8 Hz, 1H), 5.33 (s, 1H); LCMS (method B): 1.82 min (246.0, MH$^+$).

2-Chloro-N-(2-((1-methyl-1H-tetrazol-5-yl)amino)phenyl)acetamide L

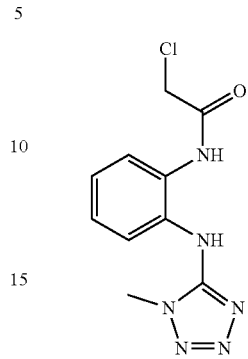

A solution of N$^1$-(1-methyl-1H-tetrazol-5-yl)benzene-1,2-diamine B (100 mg, 0.53 mmol) in dry THF (3 mL) was treated with triethylamine (0.08 mL, 0.6 mmol) and chloroacetyl chloride (0.05 mL, 0.6 mmol) and stirred at RT for 3 h. Evaporation in vacuo gave 2-chloro-N-(2-((1-methyl-1H-tetrazol-5-yl)amino)phenyl)acetamide L (140 mg, 10%) as a pink solid.

$^1$H NMR (500 MHz, d$_4$-MeOH) δ 7.55 (td, J=8.2, 1.4 Hz, 2H), 7.32-7.27 (m, 1H), 7.22 (td, J=7.7, 1.5 Hz, 1H), 4.22 (s, 2H), 3.90 (s, 3H); LCMS (method B): 1.82 min (267.1, MH$^+$).

2-(Chloromethyl)-1-(1-methyl-1H-tetrazol-5-yl)-1H-benzo[d]imidazole M

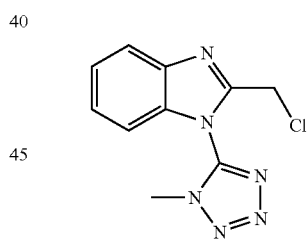

A solution of 2-chloro-N-(2-((1-methyl-1H-tetrazol-5-yl)amino)phenyl)acetamide L (140 mg, 0.53 mmol) and p-toluenesulfonic acid monohydrate (100 mg, 0.53 mmol) in MeOH (3 mL) was heated under reflux for 5 h then evaporated to dryness. The residue was dissolved in EtOAc, washed with a saturated aqueous sodium hydrogen carbonate solution, water, and brine, dried (MgSO$_4$) and chromatographed on silica (12 g Claricep cartridge) eluting with 0-100% EtOAc/PE to give 2-(chloromethyl)-1-(1-methyl-1H-tetrazol-5-yl)-1H-benzo[d]imidazole M (30 mg, 23%) as a colourless oil.

$^1$H NMR (500 MHz, CDCl$_3$) δ 7.93-7.88 (m, 1H), 7.49-7.40 (m, 2H), 7.08-7.04 (m, 1H), 4.89 (s, 2H), 3.97 (s, 3H); LCMS (method B): 2.45 min (249.1, MH$^+$).

N-(6-(((tert-Butyldimethylsilyl)oxy)methyl)pyridin-2-yl)-4-methylpentanamide N

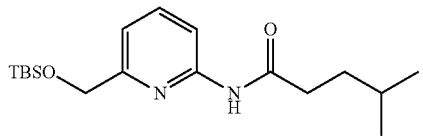 [SMILES: CC(C)CCC(=O)Nc1cccc(CO[Si](C)(C)C(C)(C)C)n1]

A solution of 6-[(tert-butyl(dimethyl)silyl)oxymethyl]pyridin-2-amine (400 mg, 1.68 mmol), 4-methylvaleric acid (0.253 mL, 2.01 mmol) and N,N-diisopropylethylamine (1.15 mL, 6.71 mmol) in DMF (5 mL) was treated with HATU (957 mg, 2.52 mmol). The reaction mixture was stirred at RT overnight. It was then diluted with water and extracted into EtOAc (2×30 mL).

The organics were washed with water (50 mL), brine (50 mL), dried (MgSO$_4$) and concentrated in vacuo. The residue was chromatographed on silica (40 g Claricep cartridge) eluting with 20-60% EtOAc/PE to give N-(6-(((tert-butyldimethylsilyl)oxy)methyl)pyridin-2-yl)-4-methylpentanamide N (500 mg, 89%) as a pale yellow oil.

$^1$H NMR (500 MHz, CDCl$_3$) δ 8.06 (d, J=8.2 Hz, 1H), 7.83 (s, 1H), 7.71 (t, J=7.9 Hz, 1H), 7.22 (d, J=7.5 Hz, 1H), 4.69 (s, 2H), 2.43-2.30 (m, 2H), 1.62 (d, J=6.2 Hz, 2H), 1.28-1.14 (m, 1H), 0.95 (s, 9H), 0.92 (d, J=6.2 Hz, 6H), 0.11 (s, 6H); LCMS (method A) 4.32 min (338.6, MH$^+$).

N-(6-(Hydroxymethyl)pyridin-2-yl)-4-methylpentanamide O

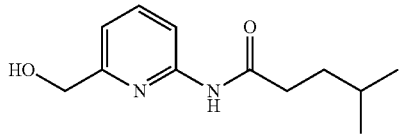 [SMILES: CC(C)CCC(=O)Nc1cccc(CO)n1]

An ice-cooled solution of N-(6-(((tert-butyldimethylsilyl)oxy)methyl)pyridin-2-yl)-4-methylpentanamide N (500 mg, 1.49 mmol) in THF (6 mL) was treated with a 1M solution of TBAF in THF (1.49 mL, 1.49 mmol) and stirred at 0° C. for 1 h. The mixture was diluted with EtOAc (50 mL), washed with water (40 mL) and brine (20 mL), dried (MgSO$_4$) and concentrated in vacuo then chromatographed on silica (25 g Claricep cartridge) eluting with 50-100% EtOAc/PE to give N-(6-(hydroxymethyl)pyridin-2-yl)-4-methylpentanamide O (255 mg, 77%) as a pale yellow gum.

$^1$H NMR (500 MHz, CDCl$_3$) δ 8.12 (d, J=8.2 Hz, 1H), 8.07 (s, 1H), 7.70 (t, J=7.9 Hz, 1H), 6.98 (d, J=7.5 Hz, 1H), 4.69 (s, 2H), 3.39 (s, 1H), 2.47-2.37 (m, 2H), 1.68-1.60 (m, 3H), 0.94 (d, J=6.3 Hz, 6H); LCMS (method A) 2.26 min (223.4, MH$^+$).

(6-((4-Methylpentyl)amino)pyridin-2-yl)methanol P

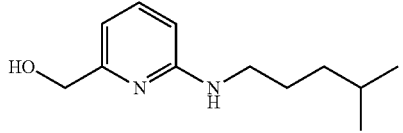

An ice-cooled solution of 1M lithium aluminium hydride in THF (2.70 mL, 2.70 mmol) in dry THF (2 mL) was treated dropwise with a solution of N-(6-(hydroxymethyl)pyridin-2-yl)-4-methylpentanamide O (200 mg, 0.90 mmol) in dry THF (2 mL), stirred at 0° C. for 1 h, warmed to RT for 2 h then cooled to 0° C. and treated with EtOAc (5 mL) and an aq. solution of Rochelle salt (5 mL). The mixture was stirred at RT for 1 h and the layers were separated. The aqueous layer was further extracted with EtOAc (15 mL) and the organics were combined, washed with brine, dried (MgSO$_4$) and concentrated in vacuo to give (6-((4-methylpentyl)amino)pyridin-2-yl)methanol P (187 mg, 100%) as a yellow oil.

$^1$H NMR (500 MHz, CDCl$_3$) δ 7.41 (t, J=7.8 Hz, 1H), 6.46 (dd, J=7.3, 0.4 Hz, 1H), 6.26 (d, J=8.3 Hz, 1H), 4.68 (br s, 1H), 4.58 (s, 2H), 3.25 (dd, J=12.9, 7.1 Hz, 2H), 1.66-1.55 (m, 3H), 1.31-1.25 (m, 2H), 0.90 (d, J=6.6 Hz, 6H); LCMS (method B): 2.21 min (209.6, MH$^+$).

6-(Isopentyloxy)picolinic acid Q

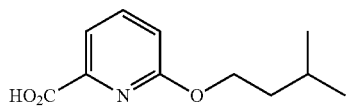

A stirred suspension of 6-bromopyridine-2-carboxylic acid (100 mg, 0.50 mmol) and 3-methyl-1-butanol (0.054 mL, 0.50 mmol) in dry THF (3 mL) was treated with a 60% mineral oil dispersion of sodium hydride (60 mg, 1.5 mmol), heated to 60° C. for 18 h then quenched with water, acidified with 1M aq. HCl and extracted into EtOAc (20 mL). The organic layer was washed with brine, dried (MgSO$_4$) and concentrated. The residue was dissolved in 1,4-dioxane (3 mL), treated with potassium tert-butoxide (111 mg, 0.10 mmol) and heated to 70° C. for 18 h. Water was added and the mixture was acidified with 1M aq. HCl and extracted into EtOAc (20 mL). The organic layer was washed with brine and dried (MgSO$_4$) to give 6-(isopentyloxy)picolinic acid Q (100 mg, 96%), used in the next step without further purification.

$^1$H NMR (500 MHz, d$_4$-MeOH) δ 7.78 (dd, J=8.2, 7.3 Hz, 1H), 7.69 (dd, J=7.3, 0.7 Hz, 1H), 6.96 (dd, J=8.3, 0.8 Hz, 1H), 4.39 (t, J=6.7 Hz, 2H), 1.80 (tt, J=13.3, 6.6 Hz, 1H), 1.65 (q, J=6.7 Hz, 2H), 0.96 (d, J=6.7 Hz, 6H); LCMS (method B): 3.22 min (210.1, MH$^+$).

(6-(Isopentyloxy)pyridin-2-yl)methanol R

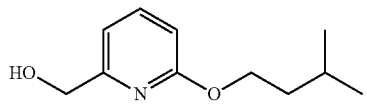

A solution of crude 6-(isopentyloxy)picolinic acid (100 mg, 0.478 mmol) in THF (1 mL) was added to an ice-cooled solution of lithium aluminium hydride (1M in THF) (0.478 mL, 0.478 mmol) in THF (1 mL) and stirred at 0° C. for 1.5 h. An aq. solution of Rochelle's salt (5 mL) and EtOAc (5 mL) were added and the mixture was stirred at RT for 1 h. The layers were separated and the aqueous layer was further extracted with EtOAc (5 mL). The organic layers were combined, washed with brine and dried (MgSO₄) to give (6-(isopentyloxy)pyridin-2-yl)methanol R (28 mg, 30%) as a green gum, used in the next step without further purification.

LCMS (method B): 3.30 min (196.2, MH⁺).

Methyl 6-(methylthio)picolinate S

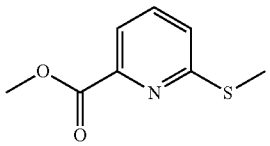

A solution of methyl 6-chloro-pyridine-2-carboxylate (100 mg, 0.58 mmol) in DMF (2 mL) was treated with sodium methanethiolate (41 mg, 0.58 mmol). The mixture was stirred at RT for 30 min then diluted with EtOAc (20 mL), washed with water (3×10 mL) and brine then dried (MgSO₄) to give methyl 6-(methylthio)picolinate S (110 mg, 72%) as a colourless oil.

¹H NMR (500 MHz, CDCl₃) δ 7.79 (dd, J=7.6, 0.9 Hz, 1H), 7.65-7.58 (m, 1H), 7.34 (dd, J=8.1, 0.9 Hz, 1H), 3.97 (s, 3H), 2.63 (s, 3H); LCMS (method B): 2.45 min (184.4, MH⁺).

(6-(Methylthio)pyridin-2-yl)methanol T

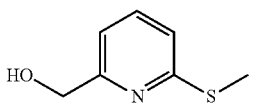

A stirred solution of methyl 6-(methylthio)picolinate S (150 mg, 0.82 mmol) in dry THF (3 mL) was treated with lithium borohydride (0.61 ml, 1.2 mmol) was heated to 40° C. for 1 h then water (15 mL) was added and the mixture was extracted with EtOAc (2×10 mL). The organic layers were combined, washed with water (10 mL) and brine then dried (MgSO₄) to give (6-(methylthio)pyridin-2-yl)methanol T (108 mg, 85%) as a colourless oil.

¹H NMR (500 MHz, CDCl₃) δ 7.50 (t, J=7.7 Hz, 1H), 7.10 (d, J=8.0 Hz, 1H), 6.91 (d, J=7.5 Hz, 1H), 4.73 (s, 2H), 2.59 (s, 3H); LCMS (method B): 1.64 min (156.1, MH⁺).

Following the same procedure as for Synthetic Intermediate ("Int.") A, substituting 1-fluoro-2-nitrobenzene and/or 5-amino-1-methyltetrazole with the required o-fluoronitrobenzene (optionally substituted with (R³)ᵧ) and/or aminoheterocycle (R²—NH₂), and using an extractive work-up (EtOAc) where a solid was not obtained upon acidification, followed by chromatography on silica if necessary, there were thus obtained the following intermediates:

| Int. | (R³)ᵧ | R²—NH2 | Yield | RTᵃ | MH⁺ |
|---|---|---|---|---|---|
| A6 | 6-F | 5-amino-1-methyl-tetrazole | 100% | 2.54 (B) | 239.1 |
| A7 | 4-F-6-MeO | 5-amino-1-methyl-tetrazole | 97% | 2.62 (B) | 269.1 |
| A8 | 4-Br | 5-amino-1-methyl-tetrazole | 99% | 2.73 (B) | 301.0ᵇ |

ᵃRT = LCMS retention time in minutes using indicated method (A-D);
ᵇOne of a pair of Br isotope ions.

Following the same procedure as for Synthetic Intermediate ("Int.") B, substituting the nitroaryl starting material ("SM") A with the required nitroaryl, there were thus obtained the following aniline intermediates (Int. B6-B7):

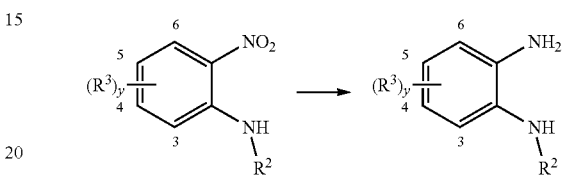

| SM | (R³)ᵧ | R² | Aniline | Yield | RTᵃ | MH⁺ |
|---|---|---|---|---|---|---|
| A6 | 6-F | 1-methyltetrazol-5-yl | B6 | 100% | 1.77(B) | 209.1 |
| A7 | 4-F-6-MeO | 1-methyltetrazol-5-yl | B7 | 47%ᵇ | 1.72(B) | 239.1 |

ᵃRT = LCMS retention time in minutes using indicated method (A-D).
ᵇThe (warm) filtered reaction mixture was concentrated by evaporation until crystallisation occurred then the suspension was cooled and solid (B7) collected by filtration.

3-Bromo-N¹-(1-methyl-1H-tetrazol-5-yl)benzene-1,2-diamine B8

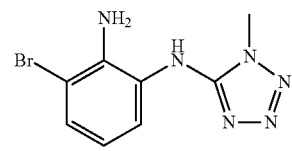

A solution of N-(3-bromo-2-nitrophenyl)-1-methyl-1H-tetrazol-5-amine A8 (4.4 g, 15 mmol) in methanol (300 mL) at ca. 40° C. was treated with water (75 mL), iron powder (3.3 g, 59 mmol) and a solution of ammonium chloride (4.7 g, 88 mmol) in water (25 mL) then heated under reflux for 6 h with vigorous stirring then (after cooling briefly) more iron powder (2 g, 36 mmol) and solid ammonium chloride (3 g, 56 mmol) were added. After heating for a further 16 h the mixture was cooled slightly then filtered whilst still hot (ca. 50° C.) through diatomaceous earth and the filter washed with hot MeOH (45-50° C.). The filtrates were concentrated to about 100 mL then cooled in ice-water. The solid was collected by filtration, washed with water (3×20 mL) and EtOAc (2×15 mL, giving a deep red-coloured filtrate, discarded) then dried in vacuo to give 3-bromo-N-(1-methyl-H-tetrazol-5-yl)benzene-1,2-diamine B8 (2.35 g, 59%), as a solid. In the NMR spectrum peaks were broadened due to traces of residual iron salts but the material was pure enough for subsequent reaction.

¹H NMR (500 MHz, DMSO-d6) δ 8.39 (s, 1H), 7.27 (d, J=4.8 Hz, 1H), 7.21 (d, J=4.2 Hz, 1H), 6.54 (s, 1H), 5.22 (s, 2H), 3.86 (s, 3H); LCMS (method B): 2.21 min (271.1 (MH⁺, one of a pair of Br isotope peaks)).

6-Fluoro-4-methoxy-1-(1-methyl-1H-tetrazol-5-yl)-1,3-dihydro-2H-benzo[d]imidazole-2-thione C6

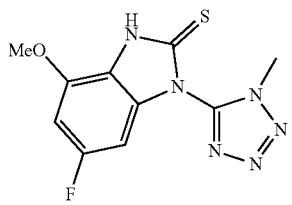 [SMILES: COc1cc(F)cc2c1[nH]c(=S)n2-c1nnnn1C]

A solution of 5-fluoro-3-methoxy-N$^1$-(1-methyl-1H-tetrazol-5-yl)benzene-1,2-diamine B7 (830 mg, 3.48 mmol) in dry DMF (5 mL) was treated with thiocarbonyldiimidazole (807 mg, 4.5 mmol) and stirred under nitrogen at 90° C. for 2 h then cooled, diluted with EtOAc (75 mL) washed with water (3×75 mL) and brine then dried (MgSO$_4$) to give 6-fluoro-4-methoxy-1-(1-methyl-1H-tetrazol-5-yl)-1,3-dihydro-2H-benzo[d]imidazole-2-thione C6 (884 mg, 91%) as an orange-brown solid.

$^1$H NMR (500 MHz, DMSO) δ 13.93 (s, 1H), 6.98 (dd, J=11.9, 2.2 Hz, 1H), 6.67 (dd, J=8.3, 2.2 Hz, 1H), 4.05 (s, 3H), 3.95 (s, 3H); LCMS (method B): 2.42 min (281.1, MH$^+$).

Following the same procedure as for Synthetic Intermediate D, starting with C6 in place of 1-(1-methyl-1H-tetrazol-5-yl)-1,3-dihydro-2H-benzo[d]imidazole-2-thione C, there was thus obtained the following intermediate (D7):

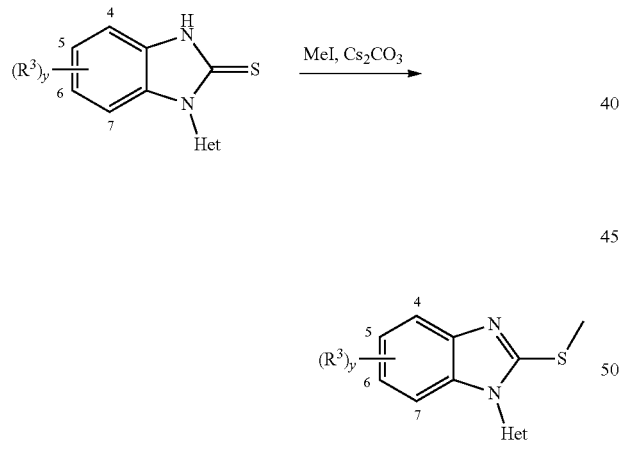

| Int. | (R$^3$)$_y$ | Het- | SM | Yield | RT$^a$ | MH$^+$ |
|---|---|---|---|---|---|---|
| D7 | 6-F-4-MeO | 1-methyltetrazol-5-yl- | C6 | 67% | 2.76 (B) | 295.1 |

$^a$RT = LCMS retention time in minutes using indicated method (A-F).

Following the same Alternative Procedure as for Synthetic Intermediate D, with the appropriate starting material (SM) in place of N$^1$-(1-methyl-1H-tetrazol-5-yl)benzene-1,2-diamine B, there were thus obtained the following Intermediates (Int. D8-D9):

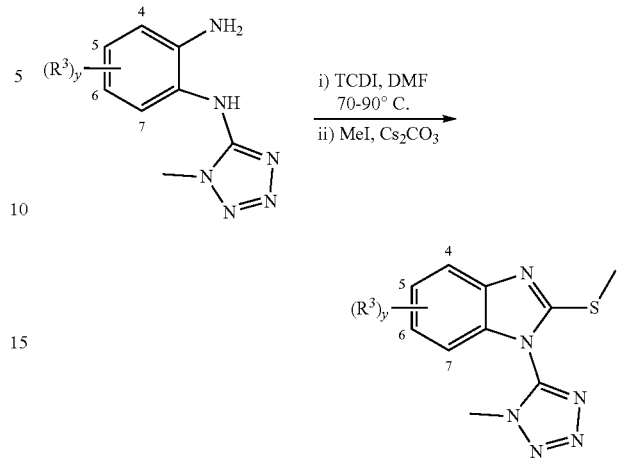

| Int. | (R)$_y$ | SM | Yield | RT$^a$ | MH$^+$ |
|---|---|---|---|---|---|
| D8 | 4-F | B6 | 75%$^b$ | 2.92 (B) | 265.1 |
| D9 | 4-Br | B8 | 73% | 3.34 (B) | 327.0$^c$ |

$^a$RT = LCMS retention time in minutes using indicated method (A-D);
$^b$Extractive work-up followed by chromatography;
$^c$One of a pair of Br isotope ions.

Following the same procedure as for Synthetic Intermediate E, with the appropriate starting material in place of 1-(1-methyl-1H-tetrazol-5-yl)-2-(methylthio)-1H-benzo[d]imidazole D, there were thus obtained the following intermediates:

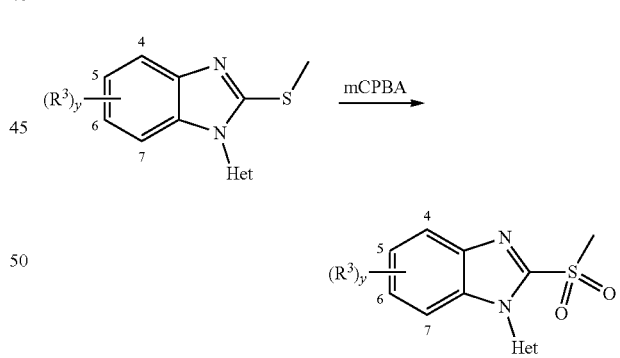

| Int. | (R$^3$)$_y$ | Het- | SM | Yield | RT$^a$ | MH$^+$ |
|---|---|---|---|---|---|---|
| E7 | 6-F-4-MeO | 1-methyltetrazol-5-yl- | D7 | 75% | 2.63 (B) | 327.1 |
| E8 | 4-F | 1-methyltetrazol-5-yl- | D8 | 83% | 2.80 (B) | 297.0 |
| E9 | 4-Br | 1-methyltetrazol-5-yl- | D9 | 89% | 3.12(B) | 359.0$^b$ |

$^a$RT = LCMS retention time in minutes using indicated method (A-D);
$^b$One of a pair of Br isotope ions.

(6-(Phenethylamino)pyridin-2-yl)methanol U

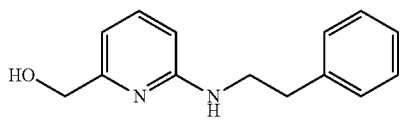 [SMILES: OCc1cccc(NCCc2ccccc2)n1]

A solution of (6-aminopyridin-2-yl)methanol (200 mg, 1.6 mmol) in DCM (8 mL) was treated with triethylamine (0.51 mL, 3.6 mmol) followed by phenylacetyl chloride (0.47 mL, 3.5 mmol). The reaction mixture was stirred at RT for 24 h then evaporated to dryness in vacuo to give crude (6-(2-phenylacetamido)pyridin-2-yl)methyl 2-phenylacetate, used directly without purification. LCMS (method B): 3.74 min (361.3, MH$^+$). An ice-cooled solution of 1M lithium aluminium hydride in THF (8.05 mL, 8.05 mmol) in dry THF (5 mL) was treated dropwise with crude (6-(2-phenylacetamido)pyridin-2-yl)methyl 2-phenylacetate (1.6 mmol, assuming quantitative conversion) in dry THF (6 mL), stirred at 0° C. for 1 h, warmed to RT for 2 h then cooled to 0° C. and treated with EtOAc (15 mL) and an aq. solution of Rochelle salt (15 mL). The mixture was stirred at RT for 1 h and the layers were separated. The aqueous layer was further extracted with EtOAc (30 mL) and the organics were combined, washed with brine, dried (MgSO$_4$) and concentrated in vacuo to give a yellow oil. Chromatography on silica (20 g Claricep cartridge) eluting with 0-100% EtOAc/PE gave (6-(phenethylamino)pyridin-2-yl)methanol U (257 mg, 70%) as a pale yellow oil.

$^1$H NMR (500 MHz, CDCl$_3$) δ 7.45-7.40 (m, 1H), 7.35 (t, J=7.5 Hz, 2H), 7.28-7.24 (m, 3H), 6.50 (d, J=7.3 Hz, 1H), 6.29 (d, J=8.2 Hz, 1H), 4.69 (br s, 1H), 4.61 (s, 2H), 3.60 (dd, J=13.1, 7.0 Hz, 2H), 2.95 (t, J=7.1 Hz, 2H); LCMS (method B): 2.27 min (229.4, MH$^+$).

(6-((2-Phenoxyethyl)amino)pyridin-2-yl)methanol U1

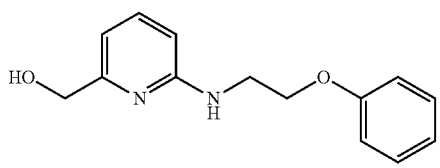 [SMILES: OCc1cccc(NCCOc2ccccc2)n1]

An ice-cooled solution of 1M lithium aluminium hydride in THF (1.10 mL, 1.10 mmol) in dry THF (1 mL) was treated dropwise with a solution of N-(6-(hydroxymethyl)pyridin-2-yl)-2-phenoxyacetamide (CAS148167-30-0) (95 mg, 0.37 mmol) in dry THF (1 mL), stirred at 0° C. for 1 h, warmed to RT for 2 h then cooled to 0° C. and treated with EtOAc (5 mL) and an aq. solution of Rochelle salt (5 mL). The mixture was stirred at RT for 1 h and the layers were separated. The aqueous layer was further extracted with EtOAc (15 mL) and the organics were combined, washed with brine, dried (MgSO$_4$) and concentrated in vacuo to give a dark yellow oil. The residue was chromatographed on silica (4 g Claricep cartridge) eluting with 0-100% EtOAc/PE to give (6-((2-phenoxyethyl)amino)pyridin-2-yl)methanol U1 (40 mg, 45%) as a yellow oil.

$^1$H NMR (500 MHz, CDCl$_3$) δ 7.42 (dd, J=8.2, 7.4 Hz, 1H), 7.29 (dd, J=8.7, 7.4 Hz, 2H), 6.97 (tt, J=7.5, 1.0 Hz, 1H), 6.92 (dd, J=8.8, 1.0 Hz, 2H), 6.50 (dd, J=7.3, 0.6 Hz, 1H), 6.37 (d, J=8.1 Hz, 1H), 5.09 (br s, 1H), 4.61 (s, 2H), 4.17 (t, J=5.2 Hz, 2H), 3.78 (q, J=5.5 Hz, 2H); LCMS (method B): 2.45 min (245.3, MH$^+$).

(4-Morpholinopyridin-2-yl)methanol V

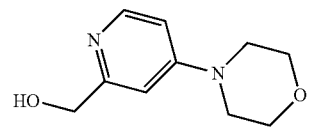 [SMILES: OCc1cc(N2CCOCC2)ccn1]

A stirred mixture of (4-chloropyridine-2-yl)methanol (200 mg, 1.4 mmol) and p-toluenesulfonic acid monohydrate (27 mg, 0.14 mmol) in morpholine (0.6 mL, 7.0 mmol) was irradiated in the microwave at 150° C. for 45 min then diluted with EtOAc (10 mL) and washed with water (3×10 mL) and brine. The aqueous layers were extracted further with EtOAc (10 mL) and the combined organic extracts were discarded (impure product, 35 mg). The aq. layers were combined and basified to pH 14 with 1M aq. NaOH and extracted further with EtOAc (2×40 mL). These organic extracts were washed with water at pH 14 and brine then dried (MgSO$_4$) and concentrated in vacuo to give (4-morpholinopyridin-2-yl)methanol V (76 mg, 28%) as a near-colourless solid.

$^1$H NMR (500 MHz, CDCl$_3$) δ 8.21 (d, J=6.0 Hz, 1H), 6.66 (d, J=2.4 Hz, 1H), 6.57 (dd, J=6.0, 2.5 Hz, 1H), 4.64 (s, 2H), 3.92-3.75 (m, 5H), 3.34-3.23 (m, 4H); LCMS (method B): 1.21 min (195.1, MH$^+$).

(4-Ethoxypyridin-2-yl)methanol W

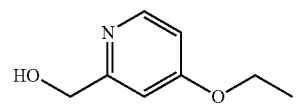

A solution of (4-nitropyridin-2-yl)methanol (100 mg, 0.65 mmol) in ethanol (4 mL) was treated with a solution of sodium ethoxide in ethanol (21% by weight, 0.31 mL, 0.83 mmol) and the reaction mixture was heated under reflux for 48 h. Water (10 mL) was added, the mixture was neutralized with concentrated aq. hydrochloric acid and ethanol was removed by evaporation in vacuo. More water (20 mL) was added and the mixture was extracted with DCM (4×30 mL). Extracts were dried (MgSO$_4$) and concentrated to give (4-ethoxypyridin-2-yl)methanol W (73 mg, 73%) as a red oil, used without purification.

LCMS (method A): 2.07 (154.1, MH$^+$).

(4-Propoxypyridin-2-yl)methanol W1

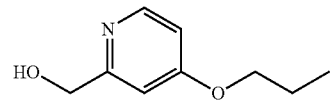

Following the procedure of Intermediate W except that a six-fold excess of a 2M solution of sodium propoxide in 1-propanol (prepared by stirring NaH with excess 1-propanol at RT for 2 h) was used as SM in place of ethanolic sodium ethoxide, there was thus obtained the title compound W1 in 73% yield (crude) as a yellow oil.

LCMS (method A): 2.43 min (168.1, MH$^+$)

N-(2-(((1-(1-Methyl-1H-tetrazol-5-yl)-1H-benzo[d]imidazol-2-yl)oxy)methyl)pyridin-4-yl)hydroxylamine X

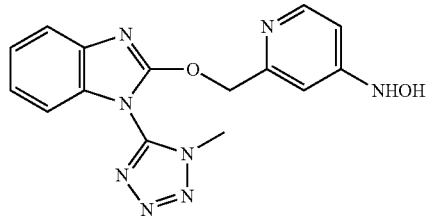

A solution of potassium carbonate (360 mg, 2.6 mmol) and sodium hydrosulfite (454 mg, 2.6 mmol) in water (6 mL) was added to a mixture of 1-(1-methyl-1H-tetrazol-5-yl)-2-((4-nitropyridin-2-yl)methoxy)-1H-benzo[d]imidazole 68 (153 mg, 0.43 mmol) and 1,1'-di-n-octyl-4,4'-bipyridinium dibromide (8 mg, 0.02 mmol) in DCM (6 mL) and the mixture was stirred at 39° C. for 24 h. Water (50 mL) was added and the mixture was extracted with EtOAc (2×50 mL). The organics were washed with brine and dried (MgSO$_4$) to give N-(2-(((1-(1-methyl-1H-tetrazol-5-yl)-1H-benzo[d]imidazol-2-yl)oxy)methyl)pyridin-4-yl)hydroxylamine X (146 mg, 99%) as a gum.

LCMS (method B): 2.78 min (339.1, MH$^+$)

EXEMPLARY COMPOUNDS

Example 1—6-(((1-(1-Methyl-1H-tetrazol-5-yl)-1H-benzo[d]imidazol-2-yl)oxy)methyl)pyridin-2-amine 1

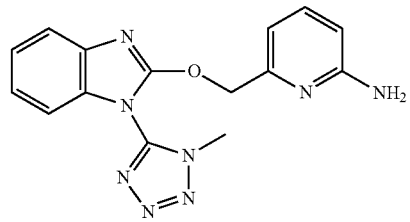 [SMILES: Cn1nnnc1-n1c(OCc2cccc(N)n2)nc2ccccc21]

An ice-cooled solution of (6-aminopyridin-2-yl)methanol (2.05 g, 16.5 mmol) in dry DMF (20 mL) was treated with a 60% mineral oil dispersion of sodium hydride (678 mg, 17.0 mmol) and the mixture was stirred at 0° C. for 15 min. An ice-cooled solution of 1-(1-methyl-1H-tetrazol-5-yl)-2-(methylsulfonyl)-1H-benzo[d]imidazole E (4.71 g, 16.9 mmol) in dry DMF (12 ml) was added and stirring was continued for 30 min. at 0° C. The mixture was treated with saturated aq. ammonium chloride solution (10 mL, to pH 7), diluted with EtOAc (80 mL), washed with water (3×120 mL) and brine, dried (MgSO$_4$) and concentrated then recrystallised from EtOAc/PE to give 6-(((1-(1-methyl-1H-tetrazol-5-yl)-1H-benzo[d]imidazol-2-yl)oxy)methyl)pyridin-2-amine 1 (4.0 g, 75%) as a white solid.

$^1$H NMR (500 MHz, CDCl$_3$) δ 7.61 (d, J=7.9 Hz, 1H), 7.45-7.39 (m, 1H), 7.33-7.29 (m, 2H), 7.27-7.22 (m, 1H), 6.72 (d, J=7.2 Hz, 1H), 6.47 (d, J=8.2 Hz, 1H), 5.53 (s, 2H), 4.64 (s, 2H), 4.06 (s, 3H); LCMS (method B): 1.68 min (323.2, MH$^+$).

Following the procedure of Example 1, using the appropriate starting materials (X is a leaving group such as halo, methylsulfonyl, arylsulfonyl), but usually with chromatography on silica for purification instead of recrystallisation, there were thus obtained the following Examples (Ex. 2-30):

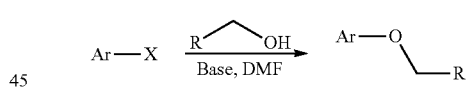

| Ex. | Ar—X | RCH$_2$OH | Yield | $^1$H NMR δ(CDCl$_3$) | RT$^a$ | Structure |
|---|---|---|---|---|---|---|
| 2 | E | | 52% | 8.72 (d, J = 4.9 Hz, 2H), 7.56 (d, J = 8.0 Hz, 1H), 7.37-7.33 (m, 1H), 7.33-7.22 (m, 3H), 5.83 (s, 2H), 4.27 (s, 3H) | 2.17 (B) | 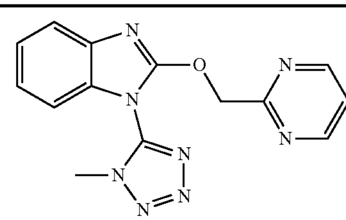 |
| 3 | E | | 12% | 8.42 (d, J = 4.1 Hz, 1H), 7.61 (d, J = 7.8 Hz, 1H), 7.55 (d, J = 7.7 Hz, 1H), 7.36-7.28 (m, 2H), 7.24 (m, 2H), 5.77 (s, 2H), 4.11 (s, 3H), 2.40 (s, 3H) | 2.13 (B) | 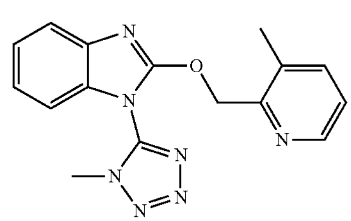 [SMILES: Cc1cccnc1COc1nc2ccccc2n1-c1nnnn1C] |

| Ex. | Ar—X | RCH₂OH | Yield | ¹H NMR δ(CDCl₃) | RT$^a$ | Structure |
|---|---|---|---|---|---|---|
| 4 | E | 4-methoxy-2-(hydroxymethyl)pyridine | 35% | 8.42 (d, J = 5.8 Hz, 1H), 7.62 (d, J = 7.9 Hz, 1H), 7.35-7.30 (m, 1H), 7.30-7.21 (m, 2H), 6.97 (m, 1H), 6.81 (m, 1H), 5.69 (s, 2H), 4.09 (s, 3H), 3.87 (s, 3H) | 1.87 (B) | 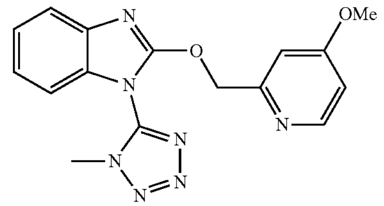 [SMILES: COc1ccnc(COc2nc3ccccc3n2-c2nnnn2C)c1] |
| 5 | E | 2-(hydroxymethyl)pyrazine | 22% | (d₆-DMSO) 8.84 (m, 1H), 8.67 (d, J = 7.6, 2H), 7.58 (d, J = 7.7 Hz, 1H), 7.39-7.33 (m, 1H), 7.30 (m, 1H), 7.25 (m, 1H), 5.79 (s, 2H), 4.11 (s, 3H) | 1.99 (B) | 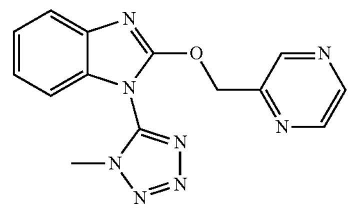 [SMILES: Cn1nnnc1-n1c(OCc2cnccn2)nc2ccccc21] |
| 6 | E | 5-methyl-2-(hydroxymethyl)pyridine | 19% | 8.45 (s, 1H), 7.62 (d, J = 7.9 Hz, 1H), 7.55 (d, J = 7.7 Hz, 1H), 7.32 (m, 3H), 7.24 (m, 1H), 5.69 (s, 2H), 4.06 (s, 3H), 2.37 (s, 3H). | 2.29 (B) | 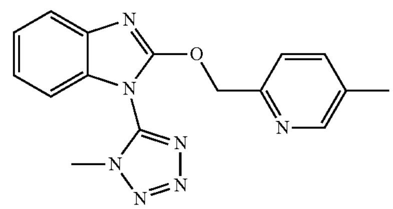 [SMILES: Cc1ccc(COc2nc3ccccc3n2-c2nnnn2C)nc1] |
| 7 | E | 4-(hydroxymethyl)pyrimidine | 33% | 9.21 (d, J = 5.2 Hz, 1H), 8.78 (d, J = 5.2 Hz, 1H), 7.61-7.57 (m, 1H), 7.41-7.38 (m, 1H), 7.35-7.31 (m, 1H), 7.30-7.24 (m, 2H), 5.72 (s, 2H), 4.16 (s, 3H) | 2.29 (B) | 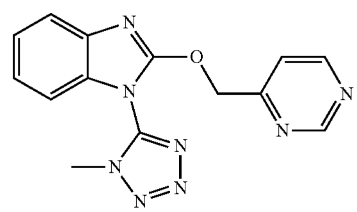 [SMILES: Cn1nnnc1-n1c(OCc2ccncn2)nc2ccccc21] |
| 8 | G | 2-(hydroxymethyl)pyridine | 20% | 9.17 (s, 1H), 8.95 (s, 1H), 8.60 (d, J = 4.7 Hz, 1H), 7.70 (t, J = 7.7 Hz, 1H), 7.63 (d, J = 7.9 Hz, 1H), 7.47 (d, J = 7.7 Hz, 1H), 7.29 (dd, J = 8.1, 4.8 Hz, 1H), 7.25-7.22 (m, 1H), 7.20 (d, J = 3.9 Hz, 2H), 5.75 (s, 2H) | 2.38 (B) | 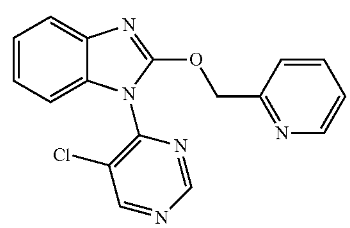 [SMILES: Clc1cncnc1-n1c(OCc2ccccn2)nc2ccccc21] |
| 9 | G | 6-amino-2-(hydroxymethyl)pyridine | 77%$^b$ | 9.16 (s, 1H), 8.95 (s, 1H), 7.62 (d, J = 7.9 Hz, 1H), 7.46 (t, J = 7.8 Hz, 1H), 7.30-7.27 (m, 1H), 7.20-7.17 (m, 2H), 6.80 (d, J = 7.3 Hz, 1H), 6.47 (d, J = 8.3 Hz, 1H), 5.57 (s, 2H), 4.77 (br s, 2H) | 1.83 (B) | 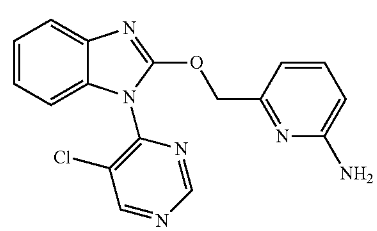 [SMILES: Nc1cccc(COc2nc3ccccc3n2-c2ncncc2Cl)n1] |

-continued

| Ex. | Ar—X | RCH₂OH | Yield | ¹H NMR δ(CDCl₃) | RT[a] | Structure |
|---|---|---|---|---|---|---|
| 10 | G | (structure) | 51%[c] | 9.11 (s, 1H), 8.87 (s, 1H), 8.32 (d, J = 5.7 Hz, 1H), 7.64 (d, J = 7.9 Hz, 1H), 7.30-7.26 (m, 1H), 7.22-7.15 (m, 2H), 6.78 (d, J = 5.7 Hz, 1H), 5.76 (s, 2H), 4.12 (t, J = 6.2 Hz, 2H), 3.56 (t, J = 6.0 Hz, 2H), 3.35 (s, 3H), 2.24 (s, 3H), 0.91-0.79 (m, 2H) | 2.88 (B) | (structure) |
| 11 | G1 | (structure) | 29% | 8.47 (d, J = 5.0 Hz, 1H), 7.62 (d, J = 7.9 Hz, 1H), 7.36-7.28 (m, 2H), 7.28-7.22 (m, 2H), 7.12 (d, J = 4.6 Hz, 1H), 5.69 (s, 2H), 4.08 (s, 3H), 2.38 (s, 3H) | 2.15 (B) | (structure) |
| 12 | G1 | (structure) | 54% | 8.23 (s, 1H), 7.62 (d, J = 8.0 Hz, 1H), 7.35-7.23 (m, 3H), 5.75 (s, 2H), 4.10 (s, 3H), 3.80 (s 3H), 2.29 (s, 6H) | 2.29 (B) | (structure) |
| 13 | G1 | (structure) | 70% | 8.23 (d, J = 5.5 Hz, 1H), 7.62 (d, J = 7.5 Hz, 1H), 7.31 (t, J = 7.8 Hz, 2H), 7.26-7.22 (m, 1H), 6.88 (d, J = 5.5 Hz, 1H), 5.77 (s, 2H), 4.10 (s, 3H), 3.94 (s, 3H), 3.87 (s, 3H) | 2.17 (B) | (structure) |
| 14 | G1 | (structure) | 70% | 8.36 (d, J = 5.6 Hz, 1H), 7.61 (d, J = 7.7 Hz, 1H), 7.34-7.29 (m, 2H), 7.27-7.22 (m, 1H), 6.73 (d, J = 5.6 Hz, 1H), 5.76 (s, 2H), 4.42 (q, J = 7.8 Hz, 2H), 4.11 (s, 3H), 2.27 (s, 3H) | 2.69 (B) | (structure) |
| 15 | G1 | (structure) | 34% | 8.31 (d, J = 5.7 Hz, 1H), 7.62 (d, J = 7.8 Hz, 1H), 7.34-7.29 (m, 2H), 7.26-7.23 (m, 1H), 6.79 (d, J = 5.7 Hz, 1H), 5.76 (s, 2H), 4.13 (t, J = 6.2 Hz, 2H), 4.09 (s, 3H), 3.56 (t, J = 6.0 Hz, 2H), 3.36 (s, 3H), 2.21 (s, 3H), 2.13-2.06 (m, 2H) | 2.09 (B) | (structure) |

| Ex. | Ar—X | RCH$_2$OH | Yield | $^1$H NMR δ(CDCl$_3$) | RT$^a$ | Structure |
|---|---|---|---|---|---|---|
| 16 | E | 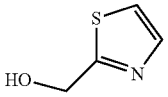 | 48% | δ 7.85 (d, J = 3.2 Hz, 1H), 7.65 (d, J = 7.9 Hz, 1H), 7.44 (d, J = 3.2 Hz, 1H), 7.36-7.27 (m, 3H), 5.92 (s, 2H), 4.03 (s, 3H) | 2.31 (B) | 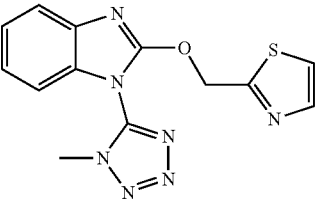 [SMILES: Cn1nnnc1-n1c(OCc2nccs2)nc2ccccc21] |
| 17 | E | 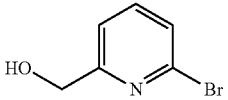 | 20% | 7.63-7.58 (m, 2H), 7.48 (d, J = 7.5 Hz, 1H), 7.39 (d, J = 7.5 Hz, 1H), 7.34-7.30 (m, 1H), 7.29-7.26 (m, 2H), 5.68 (s, 2H), 4.17 (s, 3H) | 2.80 (B) | 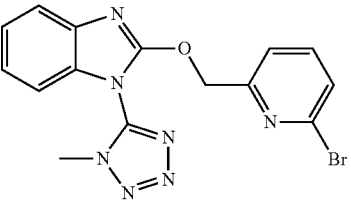 [SMILES: Cn1nnnc1-n1c(OCc2cccc(Br)n2)nc2ccccc21] |
| 18 | E | 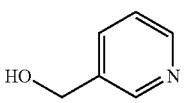 | 77%$^c$ | 8.76 (d, J = 1.8 Hz, 1H), 8.66 (dd, J = 4.8, 1.5 Hz, 1H), 7.87 (dt, J = 7.9, 1.9 Hz, 1H), 7.64 (dd, J = 8.0, 0.8 Hz, 1H), 7.39 (dd, J = 7.8, 4.8 Hz, 1H), 7.36-7.32 (m, 1H), 7.28-7.25 (m, 1H), 7.23 (ddd, J = 7.9, 1.3, 0.5 Hz, 1H), 5.67 (s, 2H), 3.95 (s, 3H) | 2.03 (B) | 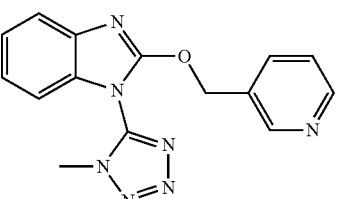 |
| 19 | E | 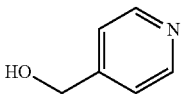 | 70%$^c$ | 8.68 (dd, J = 4.5, 1.6 Hz, 2H), 7.62 (d, J = 7.8 Hz, 1H), 7.41 (d, J = 6.1 Hz, 2H), 7.35 (td, J = 7.7, 1.2 Hz, 1H), 7.30-7.26 (m, 1H), 7.23-7.19 (m, 1H), 5.69 (s, 2H), 4.02 (s, 3H) | 1.91 (B) | 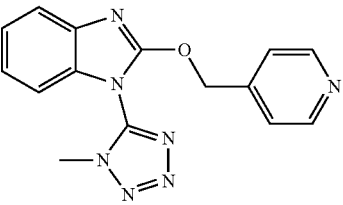 [SMILES: Cn1nnnc1-n1c(OCc2ccncc2)nc2ccccc21] |
| 20 | E1 | 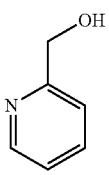 | 37% | 8.62 (d, J = 4.1 Hz, 1H), 7.75 (td, J = 7.7, 1.8 Hz, 1H), 7.53 (dd, J = 8.5, 4.7 Hz, 1H), 7.42 (d, J = 7.8 Hz, 1H), 7.31 (dd, J = 6.7, 5.0 Hz, 1H), 7.10-7.00 (m, 2H), 5.71 (s, 2H), 4.10 (s, 3H) | 2.25 (B) | 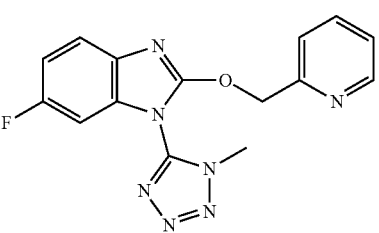 [SMILES: Cn1nnnc1-n1c(OCc2ccccn2)nc2ccc(F)cc21] |
| 21 | E | 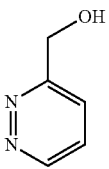 | 12%$^d$ | 7.59 (d, J = 7.2 Hz, 1H), 7.52 (dd, J = 8.5, 4.9 Hz, 1H), 7.40-7.37 (m, 1H), 7.25-7.18 (m, 4H), 5.48 (s, 2H), 4.22 (s, 3H) | 1.71 (B) | 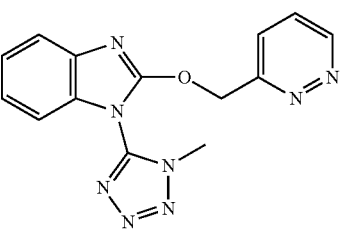 [SMILES: Cn1nnnc1-n1c(OCc2cccnn2)nc2ccccc21] |
| 22 | G | 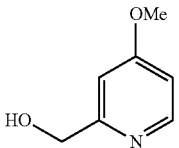 | 50%$^c$ | 9.16 (s, 1H), 8.95 (s, 1H), 8.40 (d, J = 5.7 Hz, 1H), 7.62 (dt, J = 8.0, 0.9 Hz, 1H), 7.32-7.27 (m, 1H), 7.22-7.16 (m, 2H), 7.01 (d, J = 2.3 Hz, 1H), 6.75 (dd, J = 5.8, 2.5 Hz, 1H), 5.69 (s, 2H), 3.82 (s, 3H) | 2.06 (B) | 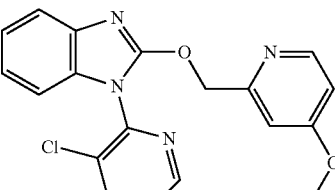 |

-continued
| Ex. | Ar—X | RCH₂OH | Yield | ¹H NMR δ(CDCl₃) | RTᵃ | Structure |
|---|---|---|---|---|---|---|
| 23 | G | 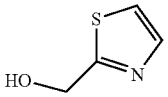 | 21%ᶜ | 9.16 (s, 1H), 8.95 (s, 1H), 7.82 (d, J = 3.2 Hz, 1H), 7.70-7.63 (m, 1H), 7.39 (d, J = 3.2 Hz, 1H), 7.35-7.27 (m, 1H), 7.24-7.19 (m, 2H), 5.92 (s, 2H) | 2.50 (B) | 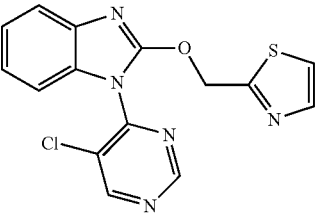 [SMILES: Clc1cncnc1-n1c(OCc2nccs2)nc2ccccc21] |
| 24 | G | 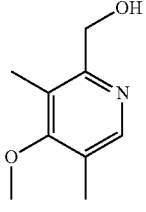 | 69%ᶜ | 9.10 (s, 1H), 8.87 (s, 1H), 8.22 (s, 1H), 7.64 (d, J = 8.0 Hz, 1H), 7.29-7.25 (m, 1H), 7.17 (dtd, J = 9.1, 8.0, 1.0 Hz, 2H), 5.72 (s, 2H), 3.76 (s, H), 2.31 (s, 3H), 2.25 (s, 3H) | 2.50 (B) | 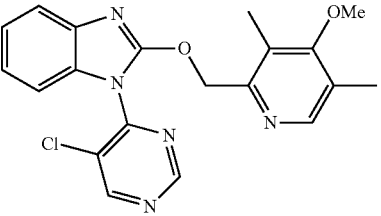 [SMILES: COc1c(C)cnc(COc2nc3ccccc3n2-c2ncncc2Cl)c1C] |
| 25 | E | 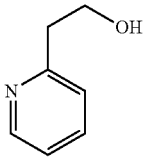 | 52%ᵉ | 8.54 (ddd, J = 4.8, 1.7, 0.9 Hz, 1H), 7.66-7.56 (m, 2H), 7.30 (ddd, J = 8.0, 6.6, 2.1 Hz, 1H), 7.26-7.20 (m, 1H), 7.17 (ddd, J = 7.5, 4.9, 1.0 Hz, 1H), 7.13 (d, J = 7.8 Hz, 1H), 5.07 (t, J = 6.3 Hz, 2H), 3.70 (s, 3H), 3.32 (t, J = 6.3 Hz, 2H) | 2.02 (B) | 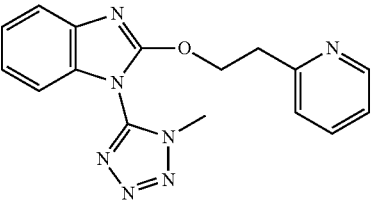 [SMILES: Cn1nnnc1-n1c(OCCc2ccccn2)nc2ccccc21] |
| 26 | E2 | 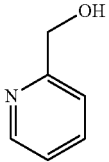 | 65% | 8.57 (d, J = 4.8 Hz, 1H), 8.51 (d, J = 3.5 Hz, 1H), 7.76 (d, J = 7.7 Hz, 1H), 7.65 (dd, J = 7.7, 1.4 Hz, 1H), 7.62 (d, J = 7.9 Hz, 1H), 7.42-7.33 (m, 2H), 7.24-7.17 (m, 2H), 7.13 (dd, J = 11.3, 4.1 Hz, 1H), 6.98 (d, J = 7.9 Hz, 1H), 5.72 (d, J = 7.0 Hz, 2H), 2.20 (s, 3H) | 6.37 (D) | 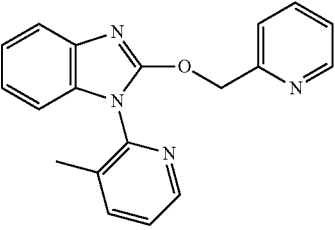 [SMILES: Cc1cccnc1-n1c(OCc2ccccn2)nc2ccccc21] |
| 27 | E3 | 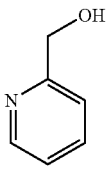 | 51% | 8.67-8.60 (m, 2H), 7.89-7.81 (m, 2H), 7.75-7.72 (m, 1H), 7.70 (td, J = 7.7, 1.8 Hz, 1H), 7.60 (dd, J = 7.1, 0.8 Hz, 1H), 7.48 (d, J = 7.9 Hz, 1H), 7.29 (ddd, J = 7.3, 4.9, 0.9 Hz, 1H), 7.24 (dt, J = 7.9, 2.2 Hz, 2H), 7.22-7.18 (m, 1H), 5.79 (s, 2H) | 6.39 (D) | 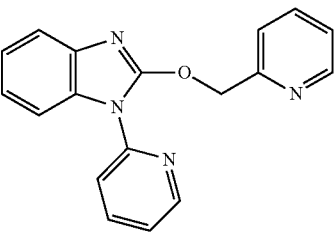 [SMILES: c1ccc(COc2nc3ccccc3n2-c2ccccn2)nc1] |
| 28 | E4 | 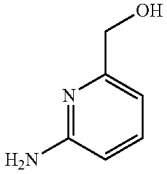 | 19% | 7.37-7.28 (m, 4H), 6.58 (d, J = 7.2 Hz, 1H), 6.41 (d, J = 8.2 Hz, 1H), 5.35 (s, 2H), 3.94 (s, 3H) | 2.34 (B) | 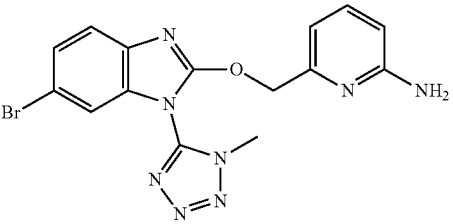 [SMILES: Cn1nnnc1-n1c(OCc2cccc(N)n2)nc2ccc(Br)cc21] |

| Ex. | Ar—X | RCH₂OH | Yield | ¹H NMR δ(CDCl₃) | RT[a] | Structure |
|---|---|---|---|---|---|---|
| 29 | I | pyridin-2-yl-CH₂OH | 33% | 8.61 (d, J = 4.3 Hz, 1H), 7.74 (td, J = 7.7, 1.5 Hz, 1H), 7.61 (d, J = 7.9 Hz, 1H), 7.42 (d, J = 7.7 Hz, 1H), 7.31 (dd, J = 16.4, 8.1 Hz, 3H), 7.25 (t, J = 7.4 Hz, 1H), 5.72 (s, 2H), 4.08 (s, 3H) | 5.92 (D) | 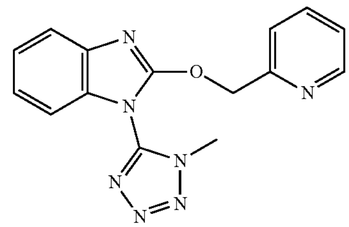 [SMILES: Cn1nnnc1-n1c(OCc2ccccn2)nc2ccccc21] |
| 30 | E5 | pyridin-2-yl-CH₂OH | 42%[c] | 8.66-8.58 (m, 1H), 7.75 (td, J = 7.7, 1.8 Hz, 1H), 7.45 (d, J = 7.8 Hz, 1H), 7.36-7.28 (m, 2H), 7.22 (dd, J = 8.1, 1.2 Hz, 1H), 7.18 (t, J = 7.9 Hz, 1H), 5.79 (s, 2H), 4.08 (s, 3H) | 2.80 (B) | 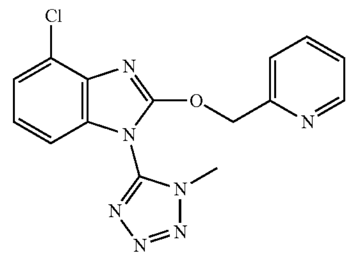 [SMILES: Cn1nnnc1-n1c(OCc2ccccn2)nc2c(Cl)cccc21] |

[a]RT = LCMS retention time in minutes using indicated method (A-F); [b]Eluent for chromatography was 0-10% MeOH/DCM; [c]Sodium hydride was added to an ice-cooled solution of Ar—X and RCH₂OH in DMF; [d]Potassium t-butoxide was added to a solution of Ar—X and RCH₂OH in THF and the mixture was stirred at 50° C. for 16 h; [e]Chromatography was performed on a basic silica column eluting with 0-100% EtOAc/PE.

Example 31—N-(6-(((1-(1-Methyl-1H-tetrazol-5-yl)-1H-benzo[d]imidazol-2-yl)oxy)methyl)pyridin-2-yl)methanesulfonamide 31

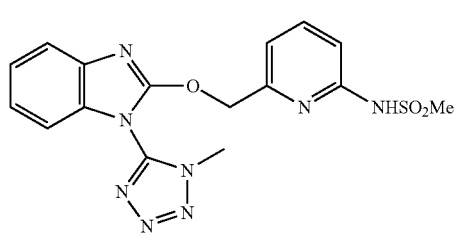

A solution of N-(6-(((1-(1-methyl-1H-tetrazol-5-yl)-1H-benzo[d]imidazol-2-yl)oxy)methyl)pyridin-2-yl)-N-(methylsulfonyl)methanesulfonamide J (40 mg, 0.084 mmol) in THF (2 mL) was treated with a 1 M aqueous solution of sodium hydroxide (0.084 ml, 0.084 mmol) at RT. The reaction mixture was stirred for 16 h then acidified to pH 4 with citric acid and extracted with ethyl acetate (2×20 mL). The organic layer was washed with water (3×20 mL) and brine, dried (MgSO₄) and chromatographed on silica (12 g Puriflash cartridge) eluting with 10-100% EtOAc/PE to give N-(6-(((1-(1-methyl-1H-tetrazol-5-yl)-1H-benzo[d]imidazol-2-yl)oxy)methyl)pyridin-2-yl)methanesulfonamide 31 (12 mg, 36%) as a cloudy white gum.

¹H NMR (500 MHz, CDCl₃) δ 7.71 (t, J=7.9 Hz, 1H), 7.60 (d, J=7.9 Hz, 1H), 7.35-7.30 (m, 1H), 7.27 (d, J=4.5 Hz, 2H), 7.10 (dd, J=13.5, 7.9 Hz, 2H), 5.65 (s, 2H), 4.06 (s, 3H), 3.13 (s. 3H). LCMS (method B): 2.19 min (401.1, MH⁺).

Example 32—1-(1-Methyl-1H-tetrazol-5-yl)-2-((6-phenylpyridin-2-yl)methoxy)-1H-benzo[d]imidazole 32

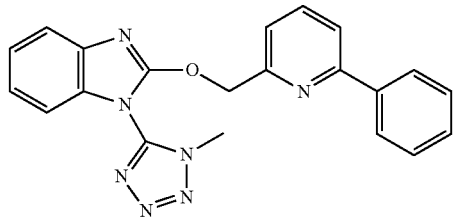 [SMILES: Cn1nnnc1-n1c(OCc2cccc(-c3ccccc3)n2)nc2ccccc21]

A solution of 2-((6-bromopyridin-2-yl)methoxy)-1-(1-methyl-1H-tetrazol-5-yl)-1H-benzo[d]imidazole 17 (45.0 mg, 0.117 mmol) and phenylboronic acid (17.1 mg, 0.140 mmol) in 1,4-dioxane (1 mL) was treated with a solution of sodium carbonate (2M, 0.233 mL, 0.466 mmol) and deoxygenated with a stream of nitrogen for 5 minutes.

Tetrakis(triphenylphosphine)palladium(0) (14 mg, 0.012 mmol) was added and the mixture was heated to 80° C. for 4.5 hours. The reaction mixture was partitioned between DCM and water. The aqueous layer was extracted with dichloromethane and the combined organics were dried (MgSO₄) and concentrated in vacuo. The crude material was purified by column chromatography (Puriflash 20 g, 0-40% ethyl acetate/petroleum ether) to isolate the product as a yellow gum 1-(1-methyl-1H-tetrazol-5-yl)-2-((6-phenylpyridin-2-yl)methoxy)-1H-benzo[d]imidazole 32 (7.5 mg, 17%) as a yellow gum.

¹H NMR (500 MHz, CDCl₃) δ 7.96-7.92 (m, 2H), 7.81 (t, J=7.8 Hz, 1H), 7.73 (d, J=7.4 Hz, 1H), 7.63 (d, J=7.9 Hz, 1H), 7.50-7.42 (m, 4H), 7.37-7.34 (m, 1H), 7.32 (d, J=7.3 Hz, 2H), 5.80 (s, 2H), 4.05 (s, 3H). LCMS (method B): 3.40 min (384.3, MH⁺).

Example 33—3-(5-Chloropyrimidin-4-yl)-2-(pyridin-2-ylmethoxy)-1H-indole 33

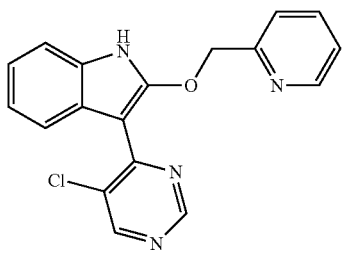 [SMILES: Clc1cncnc1-c1c(OCc2ccccn2)[nH]c2ccccc12]

A solution of 3-(5-chloropyrimidin-4-yl)indolin-2-one K (74 mg, 0.30 mmol) in dry DMF (1 mL) was treated with 2-(chloromethyl)pyridine hydrochloride (54 mg, 0.33 mmol) and caesium carbonate (260 mg, 0.80 mmol) and stirred at RT under $N_2$ for 2 h then at 80° C. for 90 min.

The mixture was cooled, quenched with saturated aq. $NH_4Cl$ solution (pH 7), diluted with water (30 mL) and extracted into EtOAc (30 mL). The organics were washed with water (3×30 mL) and brine, dried ($MgSO_4$) and chromatographed on silica (12 g Puriflash cartridge) eluting with 50-100% EtOAc/PE to give 3-(5-chloropyrimidin-4-yl)-2-(pyridin-2-ylmethoxy)-1H-indole 33 (6.5 mg, 6%) as a pale orange solid.

$^1$H NMR (500 MHz, $CDCl_3$) δ 11.27 (s, 1H), 9.09 (s, 1H), 8.74 (ddd, J=4.9, 1.6, 0.9 Hz, 1H), 8.70 (s, 1H), 7.81 (td, J=7.7, 1.8 Hz, 1H), 7.74 (dd, J=6.0, 3.2 Hz, 1H), 7.49 (d, J=7.7 Hz, 1H), 7.38 (ddd, J=5.8, 5.1, 1.9 Hz, 2H), 7.21-7.15 (m, 2H), 5.39 (s, 2H); LCMS (method A): 2.43 min (337.1, MH$^+$).

Example 34—1-(1-Methyl-1H-tetrazol-5-yl)-2-((pyridin-2-yloxy)methyl)-1H-benzo[d]imidazole 34

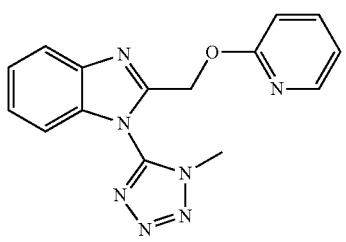 [SMILES: Cn1nnnc1-n1c(COc2ccccn2)nc2ccccc21]

A solution of pyridin-2-ol (11 mg, 0.11 mmol) in dry DMF (0.5 mL) was treated with caesium carbonate (36 mg, 0.11 mmol), stirred at RT for 5 min then a solution of 2-(chloromethyl)-1-(1-methyl-1H-tetrazol-5-yl)-1H-benzo[d]imidazole M (25 mg, 0.10 mmol) in dry DMF (0.5 mL) was added. The reaction mixture was stirred for 1 h then quenched with water (10 mL) and extracted with EtOAc (2×10 mL). The organic extracts were combined, washed with water, brine, dried ($MgSO_4$) and chromatographed on silica (4 g Claricep cartridge) eluting with 0-100% EtOAc:PE to give 1-(1-methyl-1H-tetrazol-5-yl)-2-((pyridin-2-yloxy)methyl)-1H-benzo[d]imidazole 34 (4 mg, 13%) as a yellow gum.

$^1$H NMR (500 MHz, $CDCl_3$) δ 7.98 (ddd, J=5.0, 1.9, 0.7 Hz, 1H), 7.90 (d, J=8.1 Hz, 1H), 7.55 (ddd, J=8.3, 7.1, 1.9 Hz, 1H), 7.43 (td, J=7.7, 1.2 Hz, 1H), 7.38 (td, J=7.8, 1.3 Hz, 1H), 7.05 (d, J=7.8 Hz, 1H), 6.88 (ddd, J=7.0, 5.1, 0.8 Hz, 1H), 6.53 (dd, J=8.4, 0.7 Hz, 1H), 5.66 (s, 2H), 3.86 (s, 3H); LCMS (method B): 2.69 min (308.2, MH$^+$).

Example 35—N-Benzyl-6-(((1-(1-methyl-1H-tetrazol-5-yl)-1H-benzo[d]imidazol-2-yl)oxy)methyl)pyridin-2-amine 35

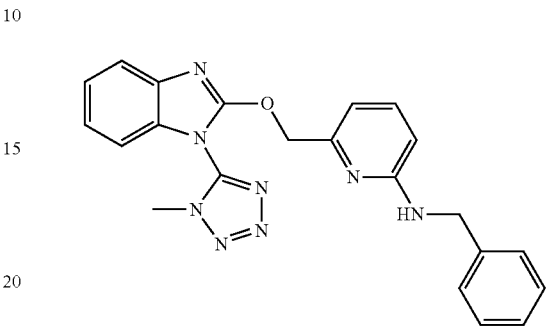

A solution of Example 1 (50 mg, 0.16 mmol) and benzaldehyde (0.016 mL, 0.16 mmol) in MeOH (2 mL) was treated with sodium cyanoborohydride (24 mg, 0.39 mmol) and acetic acid (1 drop). The mixture was stirred at RT for 18 h then saturated aq. $NH_4Cl$ solution was added and the product extracted into DCM (15 mL). The organic layer was washed with brine, dried ($MgSO_4$) and chromatographed on silica (4 g Claricep cartridge) eluting with 0-100% EtOAc PE then triturated with DCM/PE to give N-benzyl-6-(((1-(1-methyl-1H-tetrazol-5-yl)-1H-benzo[d]imidazol-2-yl)oxy)methyl)pyridin-2-amine 35 (28 mg, 44%) as white foam.

$^1$H NMR (500 MHz, $CDCl_3$) δ 7.62 (d, J=7.8 Hz, 1H), 7.44 (t, J=7.8 Hz, 1H), 7.34-7.26 (m, 7H), 7.25-7.23 (m, 1H), 6.68 (d, J=7.2 Hz, 1H), 6.40 (d, J=8.4 Hz, 1H), 5.55 (s, 2H), 4.50 (d, J=5.9 Hz, 2H), 3.98 (s, 3H); LCMS (method B): 3.27 min (413.3, MH$^+$).

Following the same procedure as for Example 35, with the appropriate aldehyde starting material in place of benzaldehyde, there were thus obtained the following Examples 36-47:

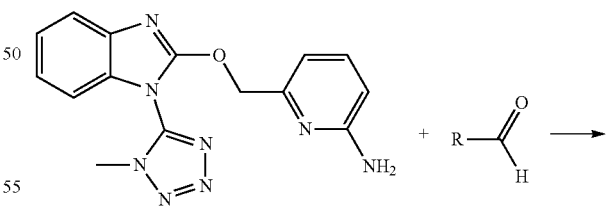

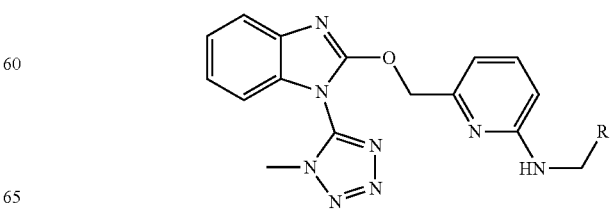

| Ex. | RCHO | Yield | $^1$H NMR δ(CDCl$_3$) | RT$^a$ | Structure |
|---|---|---|---|---|---|
| 36 |  | 33% | 7.65-7.59 (m, 1H), 7.48-7.41 (m, 1H), 7.34-7.29 (m, 2H), 7.26-7.22 (m, 1H), 6.64 (d, J = 7.2 Hz, 1H), 6.37 (d, J = 8.4 Hz, 1H), 5.52 (s, 2H), 4.08 (s, 3H), 3.32-3.22 (m, 2H), 1.24 (t, J = 7.2 Hz, 3H) | 2.45 (B) | 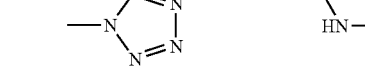 |
| 37 |  | 61% | 7.64-7.60 (m, 1H), 7.47-7.41 (m, 1H), 1H), 7.34-7.29 (m, 2H), 7.24 (dd, J = 7.9, 1.4 Hz, 1H), 6.63 (d, J = 7.2 Hz, 1H), 6.37 (d, J = 8.4 Hz, 1H), 5.52 (s, 2H), 4.07 (s, 3H), 3.27-3.19 (m, 2H), 1.69 (tt, J = 13.3, 6.7 Hz, 1H), 1.50 (dd, J = 14.6, 7.1 Hz, 2H), 0.93 (d, J = 6.6 Hz, 6H) | 3.14 (B) | 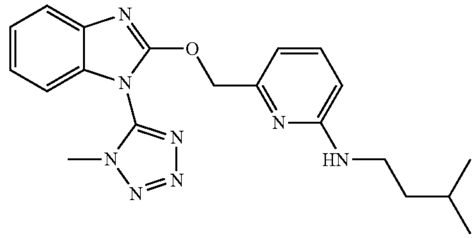 [SMILES: CC(C)CCNc1cccc(COc2nc3ccccc3n2-c2nnnn2C)n1] |
| 38 |  | 51% | 7.65-7.60 (m, 1H), 7.42 (t, J = 7.8 Hz, 1H), 7.34-7.26 (m, 4H), 7.24 (dd, J = 8.0, 1.4 Hz, 1H), 7.21-7.16 (m, 3H), 6.63 (d, J = 7.2 Hz, 1H), 6.32 (d, J = 8.4 Hz, 1H), 5.52 (s, 2H), 4.03 (s, 3H), 3.25 (dd, J = 12.6, 6.8 Hz, 2H), 2.71 (t, J = 7.6 Hz, 2H), 1.94 (dt, J = 14.5, 7.3 Hz, 2H) | 3.55 (B) | 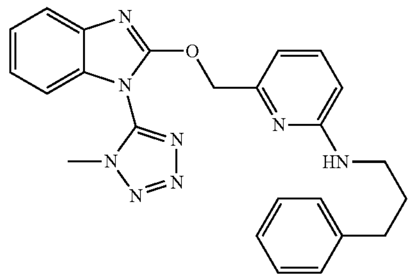 [SMILES: Cn1nnnc1-n1c(OCc2cccc(NCCCc3ccccc3)n2)nc2ccccc21] |
| 39 |  | 23% | 7.64-7.60 (m, 1H), 7.45 (t, J = 7.8 Hz, 1H), 7.35-7.29 (m, 4H), 7.26-7.23 (m, 2H), 7.22-7.19 (m, 2H), 6.65 (d, J = 7.2 Hz, 1H), 6.37 (d, J = 8.4 Hz, 1H), 5.54 (s, 2H), 4.05 (s, 3H), 3.53 (dd, J = 12.9, 7.0 Hz, 2H), 2.91 (t, J = 7.1 Hz, 2H) | 3.34 (B) | 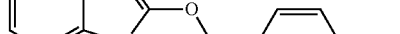 |
| 40 |  | 25% | 8.55 (d, J = 4.3 Hz, 1H), 7.69 (br s, 1H), 7.62 (d, J = 7.9 Hz, 1H), 7.45 (t, J = 7.9 Hz, 1H), 7.38-7.27 (m, 4H), 7.25-7.22 (m, 1H), 6.68 (d, J = 7.1 Hz, 1H), 6.55 (br s, 1H), 5.56 (s, 2H), 4.65 (s, 2H), 4.03 (s, 3H) | 2.49 (B) | 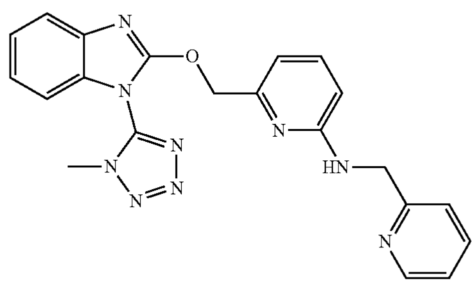 [SMILES: Cn1nnnc1-n1c(OCc2cccc(NCc3ccccn3)n2)nc2ccccc21] |
| 41 |  | 23% | 8.60 (d, J = 1.0 Hz, 1H), 8.50 (d, J = 4.2 Hz, 1H), 7.75 (d, J = 8.2 Hz, 1H), 7.61 (dt, J = 7.9, 0.8 Hz, 1H), 7.51-7.45 (m, 1H), 7.36-7.27 (m, 3H), 7.25-7.24 (m, 1H), 6.71 (d, J = 7.2 Hz, 1H), 6.45 (d, J = 8.4 Hz, 1H), 5.56 (s, 2H), 4.56 (d, J = 5.9 Hz, 2H), 4.02 (s, 3H) | 2.45 (B) | 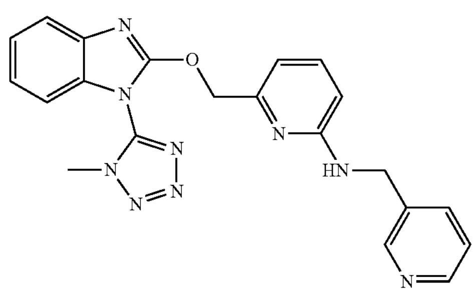 [SMILES: Cn1nnnc1-n1c(OCc2cccc(NCc3cccnc3)n2)nc2ccccc21] |

-continued

| Ex. | RCHO | Yield | ¹H NMR δ(CDCl₃) | RT$^a$ | Structure |
|---|---|---|---|---|---|
| 42 | propanal | 57% | 7.64-7.60 (m, 1H), 7.46 (t, J = 7.6 Hz, 1H), 7.34-7.29 (m, 2H), 7.27-7.22 (m, 1H), 6.64 (d, J = 7.2 Hz, 1H), 6.39 (d, J = 7.7 Hz, 1H), 5.53 (s, 2H), 4.08 (s, 3H), 3.24-3.15 (m, 2H), 1.63 (dd, J = 14.5, 7.3 Hz, 2H), 0.98 (t, J = 7.4 Hz, 3H) | 2.55 (B) | 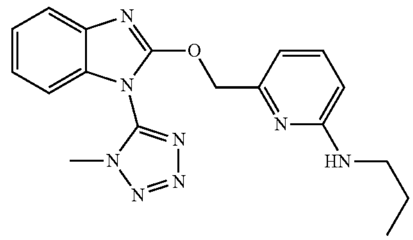 [SMILES: CCCNc1cccc(COc2nc3ccccc3n2-c2nnnn2C)n1] |
| 43 | butanal | 58% | 7.62 (dd, J = 8.7, 0.8 Hz, 1H), 7.47 (t, J = 6.5 Hz, 1H), 7.34-7.29 (m, 2H), 7.26-7.21 (m, 1H), 6.64 (d, J = 7.1 Hz, 1H), 6.40 (d, J = 7.6 Hz, 1H), 5.53 (s, 2H), 4.09 (s, 3H), 3.22 (dd, J = 12.0, 6.9 Hz, 2H), 1.60 (dt, J = 14.7, 7.2 Hz, 2H), 1.41 (dq, J = 14.5, 7.3 Hz, 2H), 0.94 (t, J = 7.4 Hz, 3H) | 3.12 (B) | 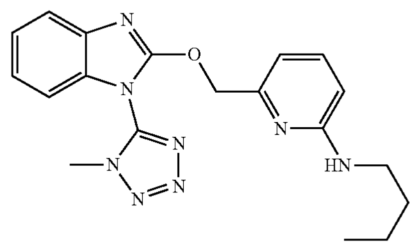 [SMILES: CCCCNc1cccc(COc2nc3ccccc3n2-c2nnnn2C)n1] |
| 44 | furfural | 64% | 7.62 (dd, J = 7.7, 1.0 Hz, 1H), 7.47 (t, J = 7.4 Hz, 1H), 7.35 (dd, J = 1.8, 0.7 Hz, 1H), 7.34-7.29 (m, 2H), 7.27-7.23 (m, 1H), 6.71 (d, J = 7.2 Hz, 1H), 6.49 (d, J = 8.1 Hz, 1H), 6.30 (dd, J = 3.2, 1.9 Hz, 1H), 6.20 (d, J = 3.0 Hz, 1H), 5.56 (s, 2H), 4.49 (d, J = 5.8 Hz, 2H), 4.04 (s, 3H) | 3.03 (B) | 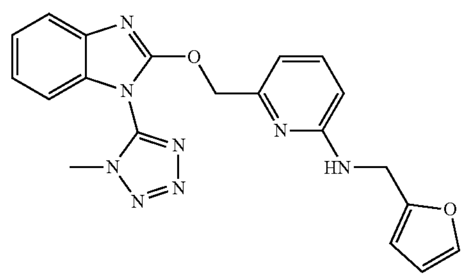 [SMILES: Cn1nnnc1-n1c(OCc2cccc(NCc3ccco3)n2)nc2ccccc21] |
| 45 | 1-methylpyrazole-3-carbaldehyde | 33% | 7.63-7.60 (m, 1H), 7.47-7.42 (m, 1H), 7.34-7.28 (m, 2H), 7.27 (d, J = 2.2 Hz, 1H), 7.24 (dd, J = 8.2, 1.1 Hz, 1H), 6.68 (d, J = 7.2 Hz, 1H), 6.53-6.46 (m, 1H), 6.14 (d, J = 2.1 Hz, 1H), 5.55 (s, 2H), 4.47 (d, J = 5.6 Hz, 2H), 4.05 (s, 3H), 3.87 (s, 3H) | 2.59 (B) | 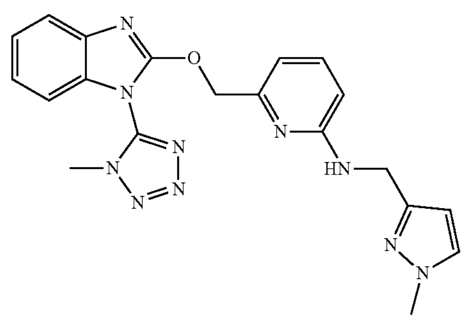 [SMILES: Cn1ccc(CNc2cccc(COc3nc4ccccc4n3-c3nnnn3C)n2)n1] |
| 46 | 4-cyanobenzaldehyde | 50% | 7.60 (dd, J = 10.5, 8.1 Hz, 3H), 7.55-7.48 (m, 1H), 7.41 (d, J = 8.1 Hz, 2H), 7.38-7.29 (m, 2H), 7.25-7.24 (m, 1H), 6.73 (d, J = 6.4 Hz, 1H), 6.40 (d, J = 6.6 Hz, 1H), 5.58 (s, 2H), 4.58 (d, J = 6.1 Hz, 2H), 4.05 (s, 3H) | 3.34 (B) | 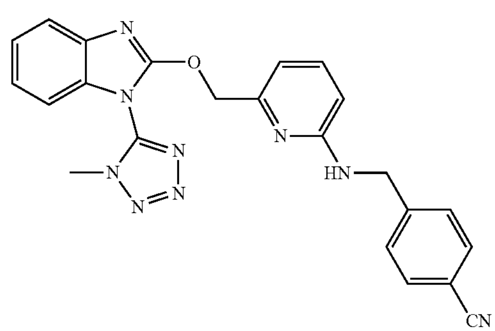 [SMILES: Cn1nnnc1-n1c(OCc2cccc(NCc3ccc(C#N)cc3)n2)nc2ccccc21] |

| Ex. | RCHO | Yield | $^1$H NMR δ(CDCl$_3$) | RT$^a$ | Structure |
|---|---|---|---|---|---|
| 47 |  | 69% | 7.64-7.60 (m, 1H), 7.44 (t, J = 7.7 Hz, 1H), 7.34-7.30 (m, 2H), 7.24 (dd, J = 8.0, 1.3 Hz, 1H), 6.64 (d, J = 7.2 Hz, 1H), 6.39 (d, J = 8.2 Hz, 1H), 5.53 (s, 2H), 4.09 (s, 3H), 3.09 (dd, J = 6.7, 5.4 Hz, 2H), 1.10-1.03 (m, 1H), 0.55 (q, J = 5.2 Hz, 2H), 0.24 (q, J = 4.9 Hz, 2H) | 2.82 (B) | 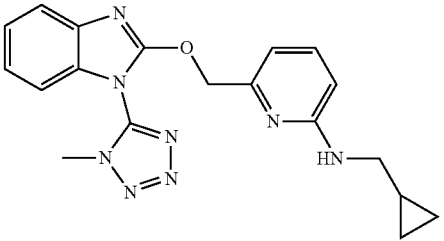 [SMILES: Cn1nnnc1-n1c(OCc2cccc(NCC3CC3)n2)nc2ccccc21] |

$^a$RT = LCMS retention time in minutes using indicated method (A-F)

Example 48—N-Methyl-6-(((1-(1-methyl-1H-tetrazol-5-yl)-1H-benzo[d]imidazol-2-yl)oxy)methyl)pyridin-2-amine 48 and Example 49—N,N-Dimethyl-6-(((1-(1-methyl-1H-tetrazol-5-yl)-1H-benzo[d]imidazol-2-yl)oxy)methyl)pyridin-2-amine 49

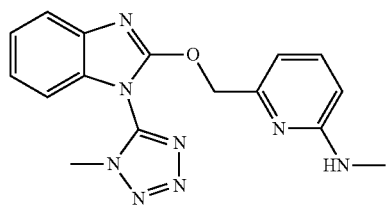

48

49

A solution of Example 1 (80 mg, 0.25 mmol) and formaldehyde (37% in water) (41 μL, 0.56 mmol) in MeOH (2 mL) was treated with sodium cyanoborohydride (39 mg, 0.62 mmol) and acetic acid (1 drop). The reaction mixture was stirred at RT for 18 h. A saturated aq. solution of NH$_4$Cl was added and the product extracted into DCM (20 mL) then washed with brine, dried (MgSO$_4$) and chromatographed on silica (4 g Claricep cartridge) eluting with 0-100% EtOAc/PE to give N-methyl-6-(((1-(1-methyl-H-tetrazol-5-yl)-1H-benzo[d]imidazol-2-yl)oxy)methyl)pyridin-2-amine 48 (24 mg, 23%) as a white foam and N,N-dimethyl-6-(((1-(1-methyl-1H-tetrazol-5-yl)-1H-benzo[d]imidazol-2-yl)oxy)methyl)pyridin-2-amine 49 (36 mg, 41%) as a pale yellow gum.

Ex. 48: $^1$H NMR (500 MHz, CDCl$_3$) δ 7.62 (dd, J=7.9, 0.7 Hz, 1H), 7.52 (t, J=7.8 Hz, 1H), 7.32 (ddd, J=7.9, 7.1, 1.6 Hz, 1H), 7.29-7.27 (m, 1H), 7.24 (dd, J=8.0, 1.1 Hz, 1H), 6.68 (d, J=7.2 Hz, 1H), 6.45 (d, J=8.5 Hz, 1H), 5.56 (s, 2H), 4.12 (s, 3H), 2.92 (d, J=5.2 Hz, 3H); LCMS (method B): 2.21 min (337.3, MH$^+$).

Ex. 49: $^1$H NMR (500 MHz, CDCl$_3$) δ 7.62 (d, J=7.9 Hz, 1H), 7.45 (t, J=7.8 Hz, 1H), 7.32 (dd, J=14.4, 7.8 Hz, 2H), 7.24 (d, J=7.6 Hz, 1H), 6.60 (d, J=7.1 Hz, 1H), 6.49 (d, J=8.4 Hz, 1H), 5.55 (s, 2H), 4.08 (s, 3H), 3.05 (s, 6H); LCMS (method B): 2.38 min (351.3, MH$^+$).

Example 50—N-Isopropyl-6-(((1-(1-methyl-1H-tetrazol-5-yl)-1H-benzo[d]imidazol-2-yl)oxy)methyl)pyridin-2-amine 50

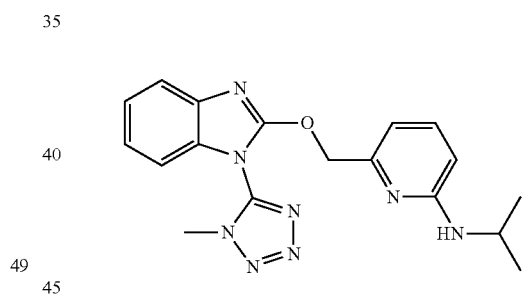

50

A solution of Example 1 (50 mg, 0.16 mmol) and acetone (14 μL, 0.19 mmol) in MeOH (2 mL) was treated with sodium cyanoborohydride (24 mg, 0.39 mmol) and acetic acid (1 drop). The reaction mixture was stirred at RT for 18 h. More acetone (14 μL, 0.19 mmol) and some anhydrous MgSO$_4$ was added and the reaction was stirred at RT for another 60 h then saturated aq. solution of NH$_4$Cl was added and the mixture was extracted with DCM (20 mL). The organic layer was washed with brine, dried (MgSO$_4$) and chromatographed on silica (4 g Claricep cartridge) eluting with 0-100% EtOAc/PE to give N-isopropyl-6-(((1-(1-methyl-1H-tetrazol-5-yl)-1H-benzo[d]imidazol-2-yl)oxy)methyl)pyridin-2-amine 50 (32 mg, 57%) as a white gum.

$^1$H NMR (500 MHz, CDCl$_3$) δ 7.64-7.59 (m, 1H), 7.50-7.41 (m, 1H), 7.35-7.28 (m, 2H), 7.25-7.22 (m, 1H), 6.62 (d, J=7.1 Hz, 1H), 6.38 (br s, 1H), 5.52 (s, 2H), 4.08 (s, 3H), 3.83 (dq, J=12.9, 6.5 Hz, 1H), 1.22 (d, J=6.3 Hz, 6H); LCMS (method B): 2.29 min (365.1, MH$^+$).

Example 51—6-(((1-(1-Methyl-1H-tetrazol-5-yl)-1H-benzo[d]imidazol-2-yloxy)methyl-N-(4-methylpentyl)pyridin-2-amine 51

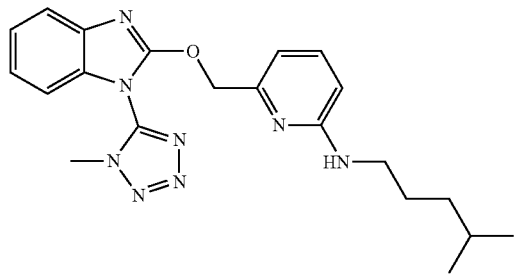 [SMILES: CC(C)CCCNc1cccc(COc2nc3ccccc3n2-c2nnnn2C)n1]

Following the method described in Example 1, but using Intermediate P in place of (6-aminopyridin-2-yl)methanol, there was thus obtained the title compound in 18% yield as a viscous yellow oil.

¹H NMR (500 MHz, CDCl₃) δ 7.63-7.60 (m, 1H), 7.46-7.41 (m, 1H), 7.31 (dd, J=7.4, 6.9 Hz, 2H), 7.24 (dd, J=8.1, 1.5 Hz, 1H), 6.63 (d, J=7.2 Hz, 1H), 6.36 (d, J=8.4 Hz, 1H), 5.52 (s, 2H), 4.07 (s, 3H), 3.20 (dd, J=12.8, 7.1 Hz, 2H), 1.64-1.52 (m, 3H), 1.25 (dd, J=15.9, 6.9 Hz, 2H), 0.89 (d, J=6.6 Hz, 6H); LCMS (method B): 3.67 min (407.3, MH⁺).

Following the procedure of Example 1, using the appropriate starting materials (X is a leaving group such as halo, methylsulfonyl, arylsulfonyl), but sodium hydride was added to a solution of the two reagents in DMF at RT and purification was by chromatography on silica instead of recrystallisation, there were thus obtained the following Examples (Ex. 52-57):

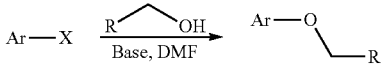

| Ex. | Ar—X | RCH₂OH | Yield | ¹H NMR δ(CDCl₃) | RTᵃ | Structure |
|---|---|---|---|---|---|---|
| 52 | E | ![OH-pyridine-OMe] | 39% | 7.62 (dd, J = 7.4, 1.7 Hz, 1H), 7.58 (dd, J = 8.4, 7.2 Hz, 1H), 7.35-7.30 (m, 2H), 7.28-7.24 (m, 1H), 6.96 (d, J = 7.2 Hz, 1H), 6.73 (d, J = 8.3 Hz, 1H), 5.61 (s, 2H), 4.08 (s, 3H), 3.87 (s, 3H) | 3.03 (B) | [structure] |
| 53 | E | R: [OH-pyridine-O-isopentyl] | 11% | 7.64-7.60 (m, 1H), 7.57 (dd, J = 8.3, 7.2 Hz, 1H), 7.35-7.30 (m, 2H), 7.27-7.23 (m, 1H), 6.93 (d, J = 7.1 Hz, 1H), 6.70 (d, J = 8.2 Hz, 1H), 5.60 (s, 2H), 4.23 (t, J = 6.8 Hz, 2H), 4.07 (s, 3H), 1.82-1.72 (m, 1H), 1.62 (dd, J = 13.7, 6.8 Hz, 2H), 0.93 (d, J = 6.6 Hz, 6H) | 3.91 (B) | [structure] |
| 54 | E | T: [OH-pyridine-SMe] | 36% | 7.62 (d, J = 7.9 Hz, 1H), 7.52 (t, J = 7.8 Hz, 1H), 7.35-7.27 (m, 3H), 7.15 (d, J = 8.0 Hz, 1H), 7.06 (d, J = 7.4 Hz, 1H), 5.67 (s, 2H), 4.07 (s, 3H), 2.48 (s, 3H) | 3.16 (B) | [structure] |
| 55 | E | 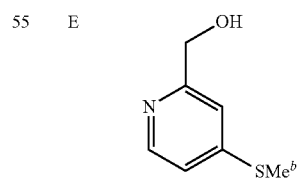 | 28%ᶜ | 8.37 (d, J = 5.4 Hz, 1H), 7.62 (d, J = 7.9 Hz, 1H), 7.35-7.30 (m, 1H), 7.30-7.21 (m, 3H), 7.09 (dd, J = 5.4 Hz, 1H), 5.67 (s, 2H), 4.09 (s, 3H), 2.49 (s, 3H) | 2.78 (B) | [structure] |

-continued

| Ex. | Ar—X | RCH$_2$OH | Yield | $^1$H NMR δ(CDCl$_3$) | RT$^a$ | Structure |
|---|---|---|---|---|---|---|
| 56 | E | 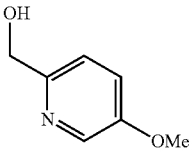 | 22%$^{c,d}$ | 8.31 (d, J = 2.9 Hz, 1H), 7.62 (d, J = 7.9 Hz, 1H), 7.42 (d, J = 8.5 Hz, 1H), 7.34-7.28 (m, 2H), 7.25-7.19 (m, 2H), 5.66 (s, 2H), 4.03 (s, 3H), 3.88 (s, 3H) | 2.65 (B) | 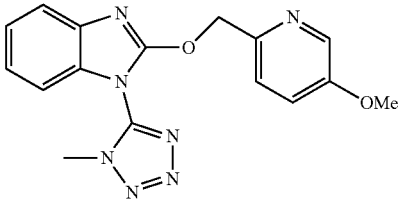 [SMILES: COc1ccc(COc2nc3ccccc3n2-c2nnnn2C)nc1] |
| 57 | E | 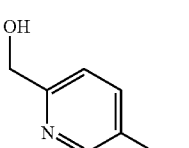 | 23%$^{c,d}$ | 7.73 (s, 1H), 7.62 (d, J = 2.6 Hz, 1H), 7.43-7.39 (m, 2H), 6.90 (d, J = 8.3 Hz, 1H), 6.74 (d, J = 8.3 Hz, 1H), 6.11 (d, J = 11.3 Hz, 1H), 5.15 (s, 2H), 4.13 (s, 3H) | 2.01 | 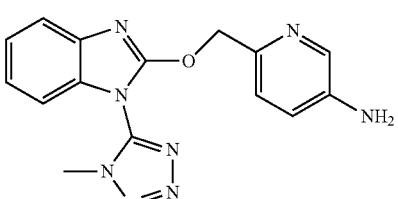 |

$^a$RT = LCMS retention time in minutes using indicated method (A-F); $^b$Prepared as described in J. Med. Chem., 1998, 41(11), 1777; $^c$Reagents mixed at 0° C.; $^d$Sodium hydride was added to the solution of RCH$_2$OH then Ar—X was added after 15 min.

Example 58—1-(1-Methyl-1H-tetrazol-5-yl)-2-((6-(methylsulfonyl)pyridin-2-yl)methoxy)-1H-benzo[d]imidazole 58

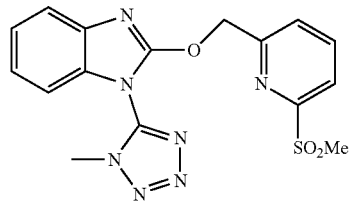 [SMILES: Cn1nnnc1-n1c(OCc2cccc(S(C)(=O)=O)n2)nc2ccccc21]

Following the same procedure as for Synthetic Intermediate E, but using Example 54 in place of sulfide D, and purification on silica eluting with 0-20% MeOH/DCM followed by trituration with DCM/PE, there was thus obtained 1-(1-methyl-1H-tetrazol-5-yl)-2-((6-(methylsulfonyl)pyridin-2-yl)methoxy)-1H-benzo[d]imidazole 58 in 100% yield as a yellow solid.

$^1$H NMR (500 MHz, CDCl$_3$) δ 8.08 (dd, J=7.7, 0.9 Hz, 1H), 8.04 (t, J=7.7 Hz, 1H), 7.69 (dd, J=7.6, 0.8 Hz, 1H), 7.59 (d, J=7.9 Hz, 1H), 7.35-7.31 (m, 1H), 7.28 (dd, J=8.0, 1.1 Hz, 1H), 7.25-7.23 (m, 1H), 5.82 (s, 2H), 4.13 (s, 3H), 3.12 (s, 3H); LCMS (method B): 2.53 min (386.2, MH$^+$).

Examples 59-79

Following the procedure of Example 1, using the appropriate starting materials (X is a leaving group such as halo, methylsulfonyl, arylsulfonyl), but often by adding sodium hydride to an ice-cooled mixture of Ar—X and RCH$_2$OH in DMF instead of adding sodium alkoxide to a solution of the alcohol before then adding Ar—X, and usually with chromatography on silica for purification instead of recrystallisation, there were thus obtained the following Examples (Ex. 59-79):

| Ex. | Ar—X | RCH$_2$OH | Yield | $^1$H NMR δ(CDCl$_3$) | RT$^a$ | Structure |
|---|---|---|---|---|---|---|
| 59 | E5 | 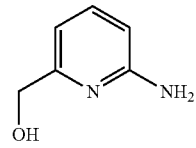 | 95%$^b$ | 7.58-7.52 (m, 1H), 7.36 (dd, J = 6.8, 2.2 Hz, 1H), 7.24-7.18 (m, 2H), 6.81 (d, J = 7.2 Hz, 1H), 6.61 (d, J = 8.4 Hz, 1H), 5.66 (s, 2H), 5.12 (br s, 2H), 4.14 (s, 3H) | 3.08 (B) | 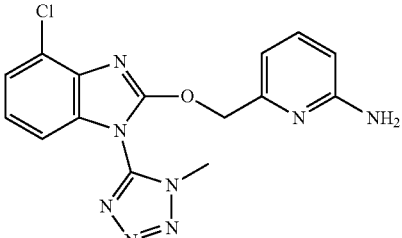 |

-continued

| Ex. | Ar—X | RCH₂OH | Yield | ¹H NMR δ(CDCl₃) | RT$^a$ | Structure |
|---|---|---|---|---|---|---|
| 60 | E5 | (3-methyl-4-(2,2,2-trifluoroethoxy)pyridin-2-yl)methanol | 27% | 8.35 (d, J = 5.6 Hz, 1H), 7.38-7.30 (m, 1H), 7.21 (d, J = 7.1 Hz, 1H), 7.17 (t, J = 7.9 Hz, 1H), 6.73 (d, J = 5.6 Hz, 1H), 5.82 (s, 2H), 4.42 (q, J = 7.8 Hz, 2H), 4.11 (d, J = 5.7 Hz, 3H), 2.30 (s, 3H) | 3.42 (B) | 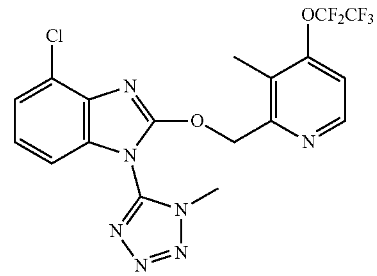 |
| 61 | E5 | (4-methoxypyridin-2-yl)methanol | 64% | 8.42 (d, J = 5.7 Hz, 1H), 7.33 (dd, J = 7.6, 1.1 Hz, 1H), 7.23-7.20 (m, 1H), 7.17 (t, J = 7.9 Hz, 1H), 7.02 (d, J = 2.3 Hz, 1H), 6.81 (dd, J = 5.7, 2.4 Hz, 1H), 5.72 (s, 2H), 4.08 (s, (s, 3H), 3.87 (s, 3H) | 2.60 (B) | 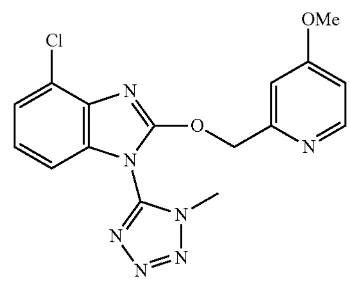 [SMILES: COc1ccnc(COc2nc3c(Cl)cccc3n2-c2nnnn2C)c1] |
| 62 | E5 | (4-(3-methoxypropoxy)-3-methylpyridin-2-yl)methanol | 42% | 8.30 (d, J = 5.6 Hz, 1H), 7.32 (dd, J = 7.8, 1.0 Hz, 1H), 7.22 (dd, J = 8.1, 1.1 Hz, 1H), 7.17 (t, J = 8.0 Hz, 1H), 6.78 (d, J = 5.6 Hz, 1H), 5.81 (s, 2H), 4.12 (t, J = 6.1 Hz, 2H), 4.08 (s, 3H), 3.56 (t, J = 6.0 Hz, 2H), 3.35 (s, 3H), 2.24 (s, 3H), 2.12-2.07 (m, 2H) | 3.03 (B) | 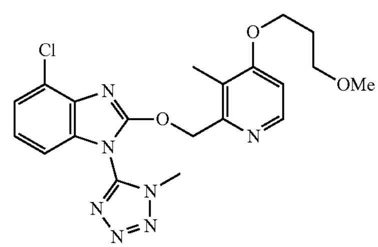 [SMILES: COCCCOc1ccnc(COc2nc3c(Cl)cccc3n2-c2nnnn2C)c1C] |
| 63 | E5 | P | 60% | 7.43 (t, J = 7.8 Hz, 1H), 7.33 (dd, J = 7.9, 0.9 Hz, 1H), 7.24 (dd, J = 8.1, 0.9 Hz, 1H), 7.17 (t, J = 8.0 Hz, 1H), 6.64 (d, J = 7.2 Hz, 1H), 6.37 (d, J = 8.4 Hz, 1H), 5.58 (s, 2H), 4.68 (br s, 1H), 4.07 (s, 3H), 3.20 (dd, J = 12.9, 7.0 Hz, 2H), 1.63-1.52 (m, 3H), 1.25 (dd, J = 15.9, 6.9 Hz, 2H), 0.89 (d, J = 6.6 Hz, 6H) | 4.33 (A) | 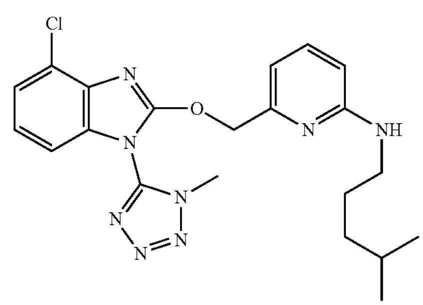 [SMILES: CC(C)CCCNc1cccc(COc2nc3c(Cl)cccc3n2-c2nnnn2C)n1] |
| 64 | E | (1-methyl-1H-benzimidazol-2-yl)methanol | 76% | 7.81-7.74 (m, 1H), 7.68-7.61 (m, 1H), 7.43-7.28 (m, 4H), 7.27-7.23 (m, 2H), 5.91 (s, 2H), 4.03 (s, 3H), 3.89 (s, 3H) | 2.69 (B) | 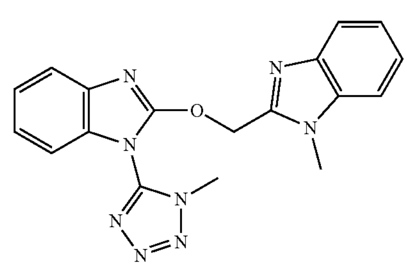 [SMILES: Cn1nnnc1-n1c(OCc2nc3ccccc3n2C)nc2ccccc21] |

| Ex. | Ar—X | RCH₂OH | Yield | ¹H NMR δ(CDCl₃) | RT^a | Structure |
|---|---|---|---|---|---|---|
| 65 | E | 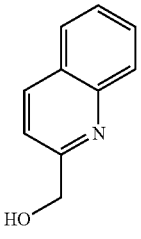 | 37% | 8.23 (d, J = 8.4, 1H), 8.04 (d, J = 8.5 Hz), 7.86 (d, J = 8.2 Hz, 1H), 7.76 (ddd, J = 8.4, 6.9, 1.4 Hz, 1H), 7.65-7.59 (m, 2H), 7.53 (d, J = 8.4 Hz, 1H), 7.37-7.31 (m, 2H), 7.27 (dt, J = 7.7, 1.2 Hz, 1H), 5.93 (s, 2H), 4.19 (s, 3H) | 3.20 (B) | 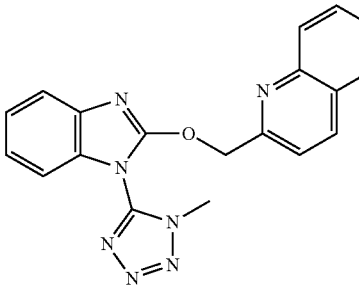 |
| 66 | E5 | 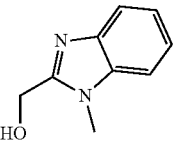 | 63% | 7.77 (d, J = 7.9 Hz, 1H), 7.42 (d, J = 8.1 Hz, 1H), 7.38 (t, J = 7.6 Hz, 1H), 7.35-7.30 (m, 2H), 7.22-7.14 (m, 2H), 5.96 (s, 2H), 4.08 (s, 3H), 4.02 (s, 3H) | 3.62 (B) | 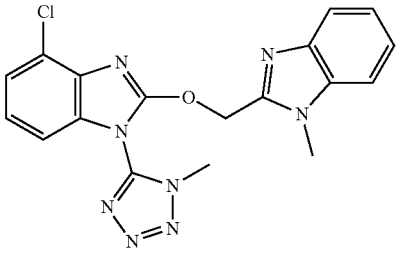 [SMILES: Cn1nnnc1-n1c(OCc2nc3ccccc3n2C)nc2c(Cl)cccc21] |
| 67 | E5 | 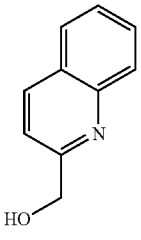 | 73% | 8.24 (d, J = 8.4 Hz, 1H), 8.04 (d, J = 8.4 Hz, 1H), 7.86 (d, J = 7.6 Hz, 1H), 7.76 (ddd, J = 8.4, 6.9, 1.4 Hz, 1H), 7.62-7.57 (m, 1H), 7.54 (d, J = 8.4 Hz, 1H), 7.34 (dd, J = 7.9, 1.1 Hz, 1H), 7.25-7.17 (m, 2H), 6.00 (s, 2H), 4.18 (s, 3H) | 3.64 (B) | 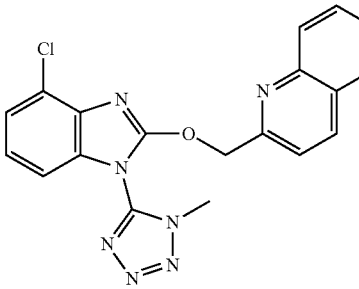 |
| 68 | E | 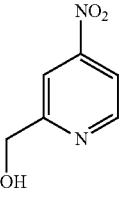 | 70% | 8.91 (d, J = 5.3 Hz, 1H), 8.17 (s, 1H), 8.04-7.98 (m, 1H), 7.59 (d, J = 7.9 Hz, 1H), 7.38-7.29 (m, 1H), 7.27-7.24 (m, 2H), 5.85 (s, 2H), 4.13 (s, 3H) | 3.01 (B) | 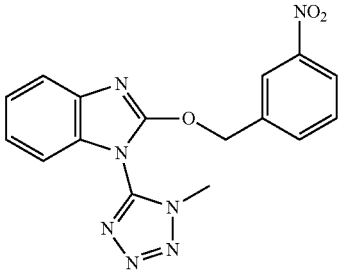 [SMILES: Cn1nnnc1-n1c(OCc2cccc([N+](=O)[O-])c2)nc2ccccc21] |
| 69 | E5 | 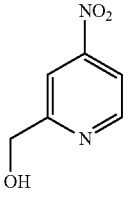 [SMILES: O=[N+]([O-])c1ccnc(CO)c1] | 78% | 8.93 (d, J = 5.3 Hz, 1H), 8.22 (d, J = 1.8 Hz, 1H), 8.04 (dd, J = 5.3, 2.1 Hz, 1H), 7.35 (dd, J = 6.7, 2.3 Hz, 1H), 7.24-7.16 (m, 2H), 5.92 (s, 2H), 4.13 (s, 3H) | 3.31 (B) | 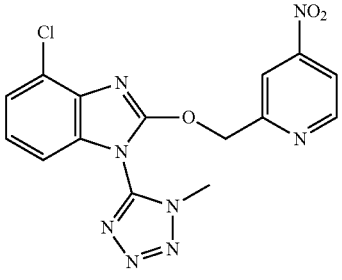 [SMILES: Cn1nnnc1-n1c(OCc2cc([N+](=O)[O-])ccn2)nc2c(Cl)cccc21] |

-continued

| Ex. | Ar—X | RCH₂OH | Yield | ¹H NMR δ(CDCl₃) | RT$^a$ | Structure |
|---|---|---|---|---|---|---|
| 70 | E5 | (2-benzothiazolyl)methanol | 44% | 8.05 (d, J = 7.9 Hz, 1H), 7.91 (dd, J = 8.0, 0.5 Hz, 1H), 7.54 (ddd, J = 8.3, 7.3, 1.2 Hz, 1H), 7.48-7.43 (m, 1H), 7.37 (dd, J = 6.5, 2.5 Hz, 1H), 7.25-7.19 (m, 2H), 6.09 (s, 2H), 4.10 (s, 3H) | 3.62 (B) | 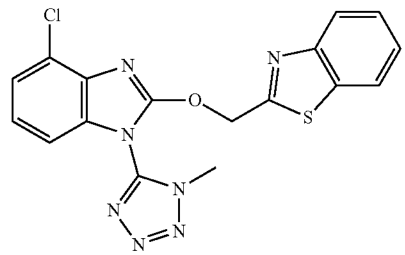 [SMILES: Cn1nnnc1-n1c(OCc2nc3ccccc3s2)nc2c(Cl)cccc21] |
| 71 | E5 | 2,6-pyridinedimethanol | 21%$^c$ | 7.76 (t, J = 7.7 Hz, 1H), 7.37 (d, J = 7.6 Hz, 1H), 7.35 (dd, J = 5.8, 3.2 Hz, 1H), 7.28 (d, J = 7.9 Hz, 1H), 7.22-7.16 (m, 2H), 5.80 (s, 2H), 4.78 (s, 2H), 4.06 (s, 3H), 3.54 (s, 1H) | 2.69 (B) | 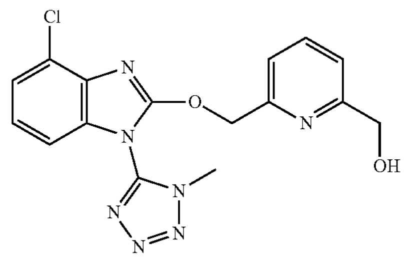 [SMILES: Cn1nnnc1-n1c(OCc2cccc(CO)n2)nc2c(Cl)cccc21] |
| 72 | E5 | [163133-18-1]$^d$ | 62% | 7.75 (t, J = 7.7 Hz, 1H), 7.42 (d, J = 7.8 Hz, 1H), 7.38-7.30 (m, 2H), 7.22 (dd, J = 8.1, 1.2 Hz, 1H), 7.17 (t, J = 7.9 Hz, 1H), 5.77 (s, 2H), 4.55 (s, 2H), 4.10 (s, 3H), 3.47 (s, 3H) | 3.28 (B) | 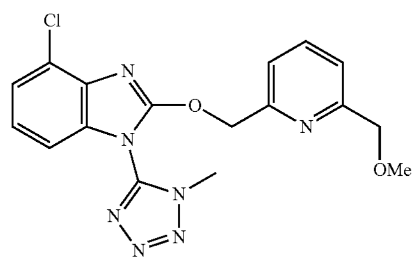 [SMILES: COCc1cccc(COc2nc3c(Cl)cccc3n2-c2nnnn2C)n1] |
| 73 | E5 | U | 28% | 7.47 (t, J = 7.8 Hz, 1H), 7.35-7.29 (m, 3H), 7.24-7.17 (m, 5H), 6.68 (d, J = 7.1 Hz, 1H), 6.40 (d, J = 8.6 Hz, 1H), 5.62 (s, 2H), 4.07 (s, 3H), 3.53 (dd, J = 13.0, 7.0 Hz, 2H), 2.92 (t, J = 7.1 Hz, 2H) | 4.15 (A) | 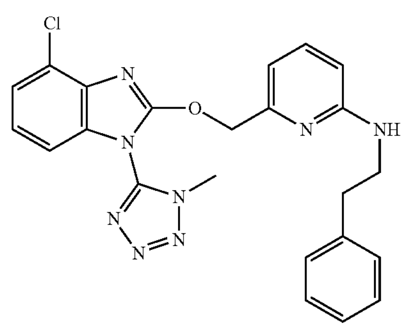 [SMILES: Cn1nnnc1-n1c(OCc2cccc(NCCc3ccccc3)n2)nc2c(Cl)cccc21] |
| 74 | E5 | U1 | 17% | 7.51 (s, 1H), 7.34 (dd, J = 7.0, 1.9 Hz, 1H), 7.28 (dd, J = 8.7, 7.4 Hz, 3H), 7.21-7.16 (m, 2H), 6.99-6.93 (m, 1H), 6.89 (dd, J = 8.6, 0.9 Hz, 2H), 6.71 (d, J = 7.4 Hz, 1H), 6.57 (s, 1H), 5.65 (s, 2H), 4.11 (t, J = 5.2 Hz, 2H), 4.08 (s, 3H), 3.72 (dd, J = 10.8, 5.4 Hz, 2H) | 4.17 (A) | 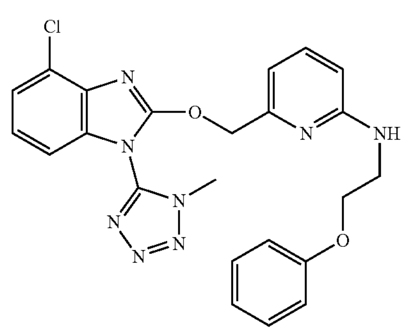 [SMILES: Cn1nnnc1-n1c(OCc2cccc(NCCOc3ccccc3)n2)nc2c(Cl)cccc21] |

-continued

| Ex. | Ar—X | RCH₂OH | Yield | ¹H NMR δ(CDCl₃) | RT[a] | Structure |
|---|---|---|---|---|---|---|
| 75 | E5 | V | 71% | 8.27 (d, J = 6.0 Hz, 1H), 7.33 (dd, J = 7.5, 1.5 Hz, 1H), 7.23-7.15 (m, 2H), 6.97 (d, J = 2.6 Hz, 1H), 6.64 (dd, J = 6.1, 2.7 Hz, 1H), 5.69 (s, 2H), 4.07 (s, 3H), 3.87-3.80 (m, 4H), 3.38-3.30 (m, 4H) | 4.09 (B) | 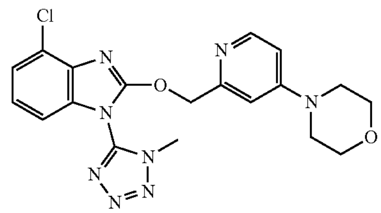 [SMILES: Cn1nnnc1-n1c(OCc2cc(N3CCOCC3)ccn2)nc2c(Cl)cccc21] |
| 76 | [2138816-14-3][e] | W | 51% | 8.40 (d, J = 5.8 Hz, 1H), 7.62 (d, J = 7.9 Hz, 1H), 7.35-7.26 (m, 3H), 6.93 (d, J = 2.4 Hz, 1H), 6.78 (dd, J = 5.8, 2.5 Hz, 1H), 5.66 (s, 2H), 4.12-4.05 (m, 5H), 1.46-1.41 (m, 3H) | 2.31 (B) | 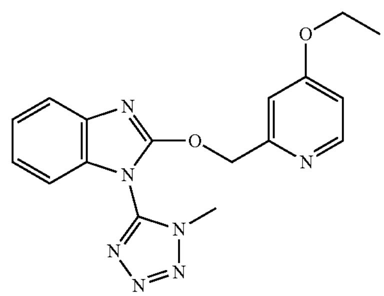 [SMILES: CCOc1ccnc(COc2nc3ccccc3n2-c2nnnn2C)c1] |
| 77 | [2138816-14-3][e] | W1 | 32% | 8.40 (d, J = 5.8 Hz, 1H), 7.62 (d, J = 7.9 Hz, 1H), 7.36-7.27 (m, 3H), 6.95 (d, J = 2.3 Hz, 1H), 6.79 (dd, J = 5.8, 2.4 Hz, 1H), 5.67 (s, 2H), 4.08 (s, 3H), 4.00-3.95 (m, 2H), 1.87-1.77 (m, 2H), 1.04 (t, J = 7.4 Hz, 3H) | 3.42 (A) | 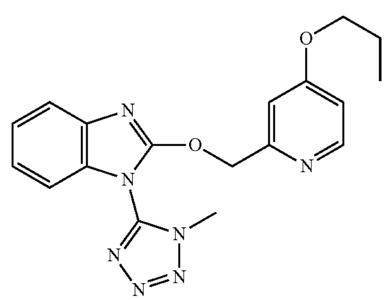 [SMILES: CCCOc1ccnc(COc2nc3ccccc3n2-c2nnnn2C)c1] |
| 78 | E7 | | 65% | 8.61 (ddd, J = 4.8, 1.6, 0.9 Hz, 1H), 7.73 (td, J = 7.7, 1.8 Hz, 1H), 7.38 (d, J = 7.8 Hz, 1H), 7.30 (ddd, J = 7.6, 4.9, 1.0 Hz, 1H), 6.69 (dd, J = 7.9, 2.2 Hz, 1H), 6.60 (dd, J = 11.5, 2.2 Hz, 1H), 5.73 (s, 2H), 4.08 (s, 3H), 4.02 (s, 3H) | 3.00 (A) | 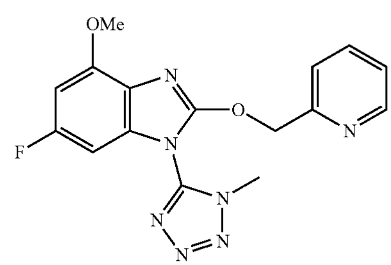 [SMILES: COc1cc(F)cc2c1nc(OCc1ccccn1)n2-c1nnnn1C] |
| 79 | E8 | | 76% | (MeOD) δ 7.47 (dd, J = 8.3, 7.3 Hz, 1H), 7.23 (dt, J = 8.2, 4.1 Hz, 1H), 7.13 (dd, J = 8.1, 0.8 Hz, 1H), 7.08 (ddd, J = 10.6, 8.3, 0.8 Hz, 1H), 6.73 (d, J = 7.2 Hz, 1H), 6.55 (d, J = 8.3 Hz, 1H), 5.52 (s, 2H), 4.08 (s, 3H) | 2.23 (B) | 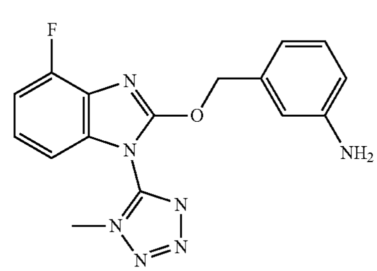 |

[a]RT = LCMS retention time in minutes using indicated method (A-D); [b]No purification required; [c]A 7-fold excess of diol and NaH was used; [d]CAS Registry No., compound may be purchased or prepared as described in *Tetrahedron: Asymmetry* 1999, 10, 243 (*J. You et al.*); [e]CAS Registry No., phenylsulfone prepared as described in WO2017/178819.

Examples 80-103

Following the same procedure as for Example 35, with the appropriate aldehyde or ketone in place of benzaldehyde and the appropriate starting material (SM) in place of Example 1, there were thus obtained the following Examples 80-103:

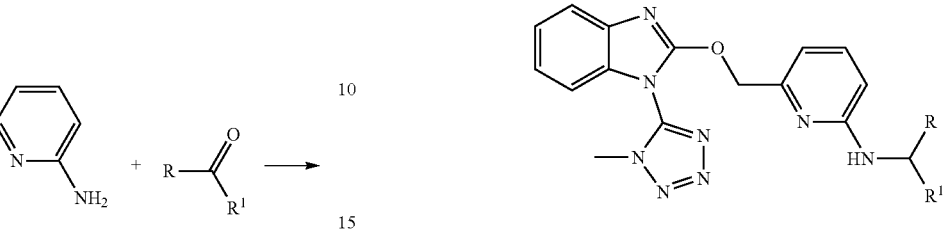

| Ex. | R(CO)R¹ | SM | Yield | ¹H NMR δ(CDCl₃) | RT$^a$ | Structure |
|---|---|---|---|---|---|---|
| 80 | cyclopentanecarboxaldehyde | 1 | 42% | 7.58 (d, J = 7.9 Hz, 1H), 7.35-7.25 (m, 4H), 6.75 (d, J = 5.9 Hz, 1H), 6.68 (br s, 1H), 5.58 (s, 2H), 4.07 (s, 3H), 3.20 (d, J = 7.3 Hz, 2H), 2.15 2.15 (dt, J = 15.1, 7.6 Hz, 1H), 1.78 (dt, J = 12.2, 6.3 Hz, 2H), 1.66-1.61 (m, 2H), 1.58-1.53 (m, 2H), 1.28-1.19 (m, 2H) | 2.83 (B) | 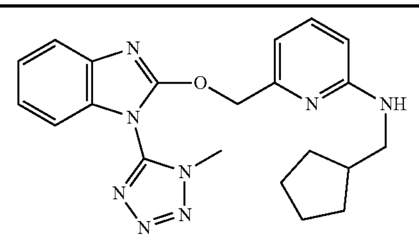 |
| 81 | cyclopentanone | 1 | 29% | 7.56 (dd, J = 7.1, 2.0 Hz, 1H), 7.39 (dd, J = 8.4, 7.2 Hz, 1H), 7.34-7.30 (m, 2H), 7.29-7.23 (m, 1H), 6.60 (d, J = 7.2 Hz, 1H), 6.44 (d, J = 8.5 Hz, 1H), 5.52 (s, 2H), 4.07 (s, 3H), 4.01 (p, J = 6.5 Hz, 1H), 1.90 (tdd, J = 8.2, 7.0, 1.4 Hz, 2H), 1.73-1.64 (m, 2H), 1.58-1.50 (m, 2H), 1.45-1.35 (m, 2H) | 2.39 (B) | 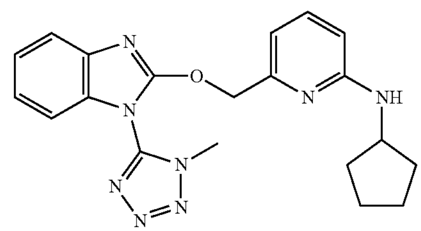 [SMILES: Cn1nnnc1-n1c(OCc2cccc(NC3CCCC3)n2)nc2ccccc21] |
| 82 | 2-butanone | 1 | 17% | 7.62 (dd, J = 7.9, 0.8 Hz, 1H), 7.47 (br s, 1H), 7.34-7.28 (m, 2H), 7.24 (dd, J = 8.1, 1.0 Hz, 1H), 6.62 (d, J = 7.1 Hz, 1H), 6.39 (br s, 1H), 5.53 (s, 2H), 4.08 (s, 3H), 3.66-3.58 (m, 1H), 1.62-1.51 (m, 2H), 1.19 (d, J = 6.3 Hz, 3H), 0.94 (t, J = 7.4 Hz, 3H) | 2.53 (B) | 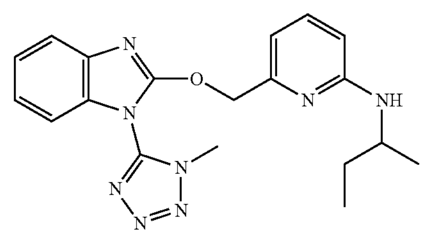 [SMILES: CCC(C)Nc1cccc(COc2nc3ccccc3n2-c2nnnn2C)n1] |
| 83 | 3,3,3-trifluoropropanal | 1 | 26% | 7.62 (d, J = 7.9 Hz, 1H), 7.51-7.45 (m, 1H), 7.35-7.31 (m, 1H), 7.30-7.24 (m, 2H), 6.70 (d, J = 7.2 Hz, 1H), 6.43 (d, J = 7.7 Hz, 1H), 5.56 (s, 2H), 4.08 (s, 3H), 3.59 (dd, J = 13.2, 6.7 Hz, 2H), 2.40 (qt, J = 10.8, 6.8 Hz, 2H) | 3.16 (B) | 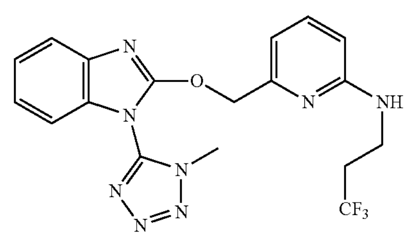 [SMILES: Cn1nnnc1-n1c(OCc2cccc(NCCC(F)(F)F)n2)nc2ccccc21] |
| 84 | 4-chlorobenzaldehyde | 1 | 63% | 7.64-7.59 (m, 1H), 7.46-7.41 (m, 1H), 7.34-7.27 (m, 4H), 7.25-7.22 (m, 3H), 6.68 (d, J = 7.2 Hz, 1H), 6.36 (d, J = 8.4 Hz, 1H), 5.54 (s, 2H), 4.46 (d, J = 5.8 Hz, 2H), 3.99 (s, 3H) | 3.79 (B) | 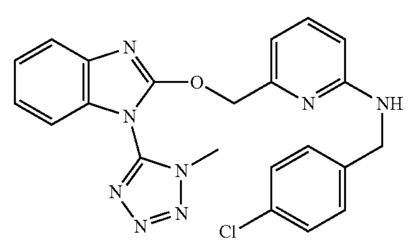 [SMILES: Cn1nnnc1-n1c(OCc2cccc(NCc3ccc(Cl)cc3)n2)nc2ccccc21] |

-continued

| Ex. | R(CO)R¹ | SM | Yield | ¹H NMR δ(CDCl₃) | RT$^a$ | Structure |
|---|---|---|---|---|---|---|
| 85 | 3-chlorobenzaldehyde | 1 | 58% | 7.62 (dd, J = 7.9, 1.1 Hz, 1H), 7.47-7.42 (m, 1H), 7.34-7.29 (m, 3H), 7.26-7.25 (m, 1H), 7.23 (dt, J = 4.9, 1.3 Hz, 2H), 7.19-7.16 (m, 1H), 6.69 (d, J = 7.2 Hz, 1H), 6.38 (d, J = 8.4 Hz, 1H), 5.55 (s, 2H), 4.49 (d, J = 6.0 Hz, 2H), 3.98 (s, 3H) | 4.21 (B) | 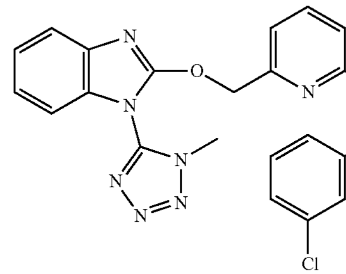 |
| 86 | 4-fluorobenzaldehyde | 1 | 60% | 7.62 (dd, J = 7.9, 1.0 Hz, 1H), 7.44 (t, J = 7.9 Hz, 1H), 7.34-7.26 (m, 5H), 7.26-7.23 (m, 1H), 6.99 (t, J = 8.6 Hz, 2H), 6.68 (d, J = 7.2 Hz, 1H), 6.37 (d, J = 8.3 Hz, 1H), 5.55 (s, 2H), 4.46 (d, J = 5.7 Hz, 2H), 4.01 (s, 3H) | 4.39 (B) | 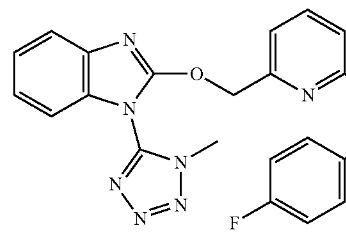 |
| 87 | cyclopropanecarbaldehyde | 59 | 44% | 7.51 (br s, 1H), 7.35-7.33 (m, 1H), 7.22-7.17 (m, 2H), 6.69 (d, J = 7.0 Hz, 1H), 6.47 (br s, 1H), 5.62 (s, 2H), 4.12 (s, 3H), 3.12 (t, J = 5.1 Hz, 2H), 1.12-1.04 (m, 1H), 0.58 (d, J = 6.3 Hz, 2H), 0.26 (d, J = 4.2 Hz, 2H). | 2.80 (B) | 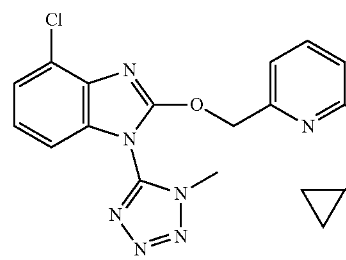 |
| 88 | propanal | 59 | 31% | 7.50 (br s, 1H), 7.34 (dd, J = 7.6, 1.5 Hz, 1H), 7.19 (dd, J = 13.9, 6.3 Hz, 2H), 6.68 (d, J = 7.1 Hz, 1H), 6.45 (d, J = 7.1 Hz, 1H), 5.61 (s, 2H), 4.10 (s, 3H), 3.21 (dd, J = 11.7, 6.9 Hz, 2H), 1.65 (dq, J = 14.5, 7.3 Hz, 2H), 0.99 (t, J = 7.4 Hz, 3H) | 2.66 (B) | 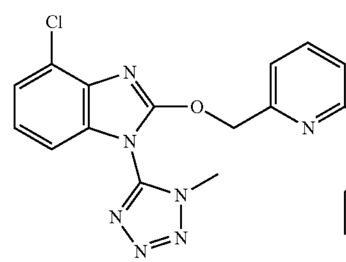 |
| 89 | benzaldehyde | 59 | 51% | 7.47 (br s, 1H), 7.35-7.28 (m, 6H), 7.21-7.15 (m, 2H), 6.72 (d, J = 7.0 Hz, 1H), 6.45 (d, J = 8.1 Hz, 1H), 5.64 (s, 2H), 4.51 (d, J = 5.9 Hz, 2H), 4.01 (s, 3H) | 4.11 (A) | 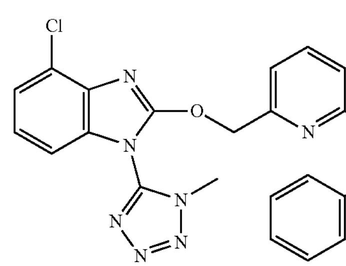 |
| 90 | 3-methylbutanal | 59 | 61% | 7.46 (dd, J = 8.2, 7.5 Hz, 1H), 7.33 (dd, J = 7.9, 1.1 Hz, 1H), 7.23 (dd, J = 8.1, 1.0 Hz, 1H), 7.17 (t, J = 7.9 Hz, 1H), 6.65 (d, J = 7.2 Hz, 1H), 6.39 (d, J = 8.5 Hz, 1H), 5.59 (s, 2H), 4.08 (s, 3H), 3.28-3.20 (m, 2H), 1.69 (hept, J = 6.7 Hz, 1H), 1.50 (q, J = 7.1 Hz, 2H), 0.94 (d, J = 6.6 Hz, 6H) | 4.27 (A) | 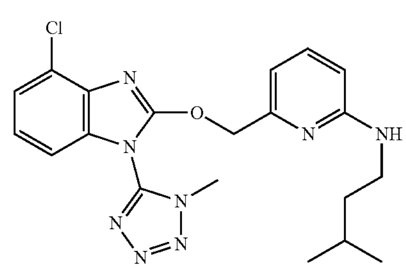 [SMILES: CC(C)CCNc1cccc(COc2nc3c(Cl)cccc3n2-c2nnnn2C)n1] |

-continued

| Ex. | R(CO)R¹ | SM | Yield | ¹H NMR δ(CDCl₃) | RTᵃ | Structure |
|---|---|---|---|---|---|---|
| 91 | cyclopropanecarbaldehyde | 79 | 52% | 7.57 (br s, 1H), 7.19 (td, J = 8.2, 4.6 Hz, 1H), 7.09-7.04 (m, 2H), 6.71 (d, J = 6.4 Hz, 1H), 6.53 (br s, 1H), 5.63 (s, 2H), 4.16 (s, 3H), 3.16-3.09 (m, 2H), 1.12-1.06 (m, 1H), 0.60 (d, J = 7.2 Hz, 2H), 0.28 (q, J = 4.8 Hz, 2H) | 3.18 (B) | 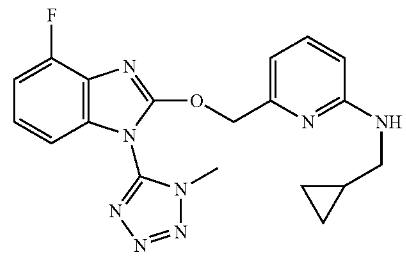 [SMILES: Cn1nnnc1-n1c(OCc2cccc(NCC3CC3)n2)nc2c(F)cccc21] |
| 92 | 2-chlorobenzaldehyde | 1 | 63% | 7.62 (d, J = 7.8 Hz, 1H), 7.50-7.43 (m, 1H), 7.38-7.35 (m, 2H), 7.34-7.30 (m, 2H), 7.29 (s, 1H), 7.25-7.15 (m, 3H), 6.70 (d, J = 7.0 Hz, 1H), 6.47-6.36 (m, 1H), 5.56 (s, 2H), 4.60 (d, J = 6.1 Hz, 2H), 4.00 (s, 3H) | 4.03 (B) | 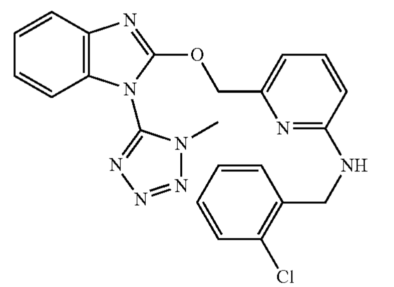 [SMILES: Cn1nnnc1-n1c(OCc2cccc(NCc3ccccc3Cl)n2)nc2ccccc21] |
| 93 | 3-cyanobenzaldehyde | 1 | 42% | 7.64-7.59 (m, 2H), 7.54 (dd, J = 7.4, 1.1 Hz, 2H), 7.50-7.45 (m, 1H), 7.41 (t, J = 7.8 Hz, 1H), 7.34-7.30 (m, 1H), 7.28-7.26 (m, 2H), 6.72 (d, J = 7.3 Hz, 1H), 6.39 (d, J = 8.4 Hz, 1H), 5.57 (s, 2H), 4.55 (d, J = 6.1 Hz, 2H), 4.02 (s, 3H) | 3.82 (A) | 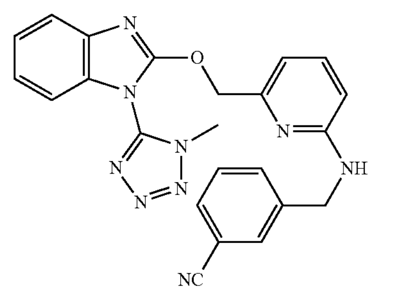 [SMILES: Cn1nnnc1-n1c(OCc2cccc(NCc3cccc(C#N)c3)n2)nc2ccccc21] |
| 94 | 3-methoxybenzaldehyde | 1 | 57% | 7.64-7.60 (m, 1H), 7.42 (dd, J = 8.2, 7.4 Hz, 1H), 7.34-7.30 (m, 2H), 7.26-7.20 (m, 2H), 6.90-6.85 (m, 2H), 6.80 (dd, J = 8.2, 2.5 Hz, 1H), 6.67 (d, J = 7.2 Hz, 1H), 6.38 (d, J = 8.4 Hz, 1H), 5.54 (s, 2H), 4.47 (d, J = 5.9 Hz, 2H), 3.98 (s, 3H), 3.78 (s, 3H) | 3.86 (A) | 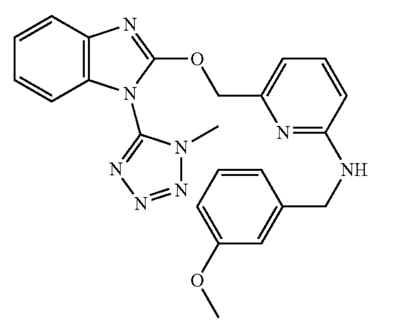 [SMILES: COc1cccc(CNc2cccc(COc3nc4ccccc4n3-c3nnnn3C)n2)c1] |
| 95 | 3-methylbenzaldehyde | 1 | 72% | 7.64-7.61 (m, 1H), 7.43 (t, J = 7.8 Hz, 1H), 7.34-7.30 2H), 7.25-7.23 (m, 1H), 7.20 (t, J = 7.5 Hz, 1H), 7.13 (s, 1H), 7.09 (t, J = 8.7 Hz, 2H), 6.67 (d, J = 7.2 Hz, 1H), 6.39 (d, J = 8.4 Hz, 1H), 5.54 (s, 2H), 4.45 (d, J = 5.8 Hz, 2H), 3.99 (s, 3H), 2.33 (s, 3H) | 4.05 (B) | 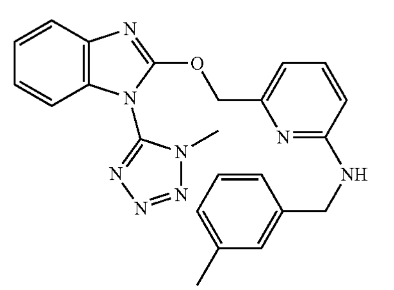 [SMILES: Cc1cccc(CNc2cccc(COc3nc4ccccc4n3-c3nnnn3C)n2)c1] |

-continued

| Ex. | R(CO)R¹ | SM | Yield | ¹H NMR δ(CDCl₃) | RT$^a$ | Structure |
|---|---|---|---|---|---|---|
| 96 | 3-(trifluoromethoxy)benzaldehyde | 1 | 54% | 7.65-7.60 (m, 1H), 7.47-7.42 (m, 1H), 7.34-7.29 (m, 3H), 7.27-7.26 (m, 1H), 7.26-7.21 (m, 2H), 7.11 (d, J = 8.1 Hz, 1H), 6.70 (d, J = 7.2 Hz, 1H), 6.38 (d, J = 8.4 Hz, 1H), 5.55 (s, 2H), 4.53 (d, J = 5.9 Hz, 2H), 3.98 (s, 3H) | 4.06 (B) | benzimidazole-tetrazole-pyridine-CH₂NH-(3-OCF₃-phenyl) |
| 97 | 3-(trifluoromethyl)benzaldehyde | 1 | 55% | 7.62 (d, J = 7.9 Hz, 1H), 7.58 (s, 1H), 7.51 (dd, J = 13.1, 7.9 Hz, 2H), 7.47-7.39 (m, 2H), 7.34-7.29 (m, 2H), 7.27-7.26 (m, J = 1.2 Hz, 1H), 7.25-7.23 (m, 1H), 6.70 (d, J = 7.2 Hz, 1H), 6.38 (d, J = 8.4 Hz, 1H), 5.55 (s, 2H), 4.57 (d, J = 6.0 Hz, 2H), 3.98 (s, 3H) | 4.02 (A) | benzimidazole-tetrazole-pyridine-CH₂NH-(3-CF₃-phenyl) |
| 98 | butyraldehyde | 59 | 29% | 7.75-7.63 (m, 1H), 7.36-7.32 (m, 1H), 7.21-7.16 (m, 2H), 7.09 (d, J = 8.0 Hz, 1H), 6.77 (d, J = 7.0 Hz, 1H), 6.73-6.63 (m, 1H), 5.71 (s, 2H), 4.21 (s, 3H), 3.29-3.25 (m, 2H), 1.70-1.65 (m, 2H), 1.47-1.43 (m, 2H), 0.96 (t, J = 7.3 Hz, 3H) | 2.12 (E) | Cl-benzimidazole-tetrazole-pyridine-CH₂NH-butyl |
| 99 | propionaldehyde | 106 | 33% | 7.82-7.75 (m, 1H), 7.51 (dd, J = 7.9, 1.0 Hz, 1H), 7.15-7.12 (m, 2H), 7.10-7.06 (m, 1H), 6.84 (d, J = 7.0 Hz, 1H), 6.78 (d, J = 9.0 Hz, 1H), 5.75 (s, 2H), 4.25 (s, 3H), 3.28-3.24 (m, 2H), 1.79-1.72 (m, 2H), 1.05 (t, J = 7.4 Hz, 3H) | 2.08 (E) | Br-benzimidazole-tetrazole-pyridine-CH₂NH-propyl |
| 100$^b$ | cyclopropanecarboxaldehyde | 106 | 62% | (DMSO-d6) 7.52 (d, J = 8.0 Hz, 1H), 7.36 (t, J = 8.3 Hz, 2H), 7.18 (t, J = 8.0 Hz, 1H), 6.71 (t, J = 5.3 Hz, 1H), 6.54 (d, J = 7.1 Hz, 1H), 6.44 (d, J = 8.4 Hz, 1H), 5.50 (s, 2H), 4.11 (s, 3H), 3.01 (t, J = 6.1 Hz, 2H), 0.99-0.90 (m, 1H), 0.39-0.30 (m, 2H), 0.12 (q, J = 4.8 Hz, 2H) | 2.08 (E) | Br-benzimidazole-tetrazole-pyridine-CH₂NH-CH₂-cyclopropyl |

-continued

| Ex. | R(CO)R¹ | SM | Yield | ¹H NMR δ(CDCl₃) | RTᵃ | Structure |
|---|---|---|---|---|---|---|
| 101 | 3-methylbenzaldehyde | 59 | 41% | (DMSO-d6) 7.42-7.38 (m, 2H), 7.35 (dd, J = 8.1, 1.0 Hz, 1H), 7.25 (t, J = 8.0 Hz, 1H), 7.17-7.12 (m, 2H), 7.10 (s, 1H), 7.06 (d, J = 7.6 Hz, 1H), 7.02 (d, J = 7.4 Hz, 1H), 6.59 (d, J = 7.1 Hz, 1H), 6.47 (d, J = 8.4 Hz, 1H), 5.52 (s, 2H), 4.38 (d, J = 6.0 Hz, 2H), 4.04 (s, 3H), 2.26 (s, 3H) | 2.27 (E) | (Cl-benzimidazole tetrazole pyridine structure) |
| 102 | 3-methylbenzaldehyde | 106 | 73% | 7.72 (t, J = 8.5 Hz, 1H), 7.51 (dd, J = 7.7, 1.2 Hz, 1H), 7.24 (d, J = 8.4 Hz, 1H), 7.16-7.09 (m, 5H), 6.87 (d, J = 7.0 Hz, 1H), 6.69 (d, J = 8.7 Hz, 1H), 5.78 (s, 2H), 4.50 (d, J = 5.6 Hz, 2H), 4.24 (s, 3H), 2.34 (s, 3H) | 2.31 (E) | (Br-benzimidazole tetrazole pyridine structure) |
| 103ᶜ | acetone | 59 | 52% | 7.48-7.41 (m, 1H), 7.33 (dd, J = 7.8, 1.2 Hz, 1H), 7.22 (dd, J = 8.1, 1.1 Hz, 1H), 7.17 (t, J = 8.0 Hz, 1H), 6.64 (d, J = 7.1 Hz, 1H), 6.38 (d, J = 8.5 Hz, 1H), 5.59 (s, 2H), 4.85 (br s, 1H), 4.08 (s, 3H), 3.88-3.79 (m, 1H), 1.22 (d, J = 6.4 Hz, 6H) | 1.58 (F) | (Cl-benzimidazole tetrazole pyridine isopropylamine structure) |

ᵃRT = LCMS retention time in minutes using indicated method (A-F); ᵇ1.3eq of the aldehyde and 0.5eq AcOH, heated for 1 h at 55° C. and then RT for 18 h; ᶜExcess acetone used and further aliquots of AcOH, reaction carried out at 50° C.

Examples 104-106

Following the procedure of Example 1, using the appropriate starting materials (X is a leaving group such as halo, methylsulfonyl, arylsulfonyl), but often by adding sodium hydride to an ice-cooled mixture of Ar—X and RCH₂OH in DMF instead of adding sodium alkoxide to a solution of the alcohol before then adding Ar—X, and usually with chromatography on silica for purification instead of recrystallisation, there were thus obtained the following Examples (Ex. 104-106):

| Ex. | Ar—X | RCH₂OH | Yield | ¹H NMR δ(CDCl₃) | RT[a] | Structure |
|---|---|---|---|---|---|---|
| 104[b] | E9 | benzothiazole-2-methanol | 45% | 8.06 (d, J = 7.8 Hz, 1H), 7.96-7.87 (m, 1H), 7.57-7.51 (m, 2H), 7.46 (ddd, J = 8.3, 7.3, 1.2 Hz, 1H), 7.29-7.26 (m, 1H), 7.16 (t, J = 8.0 8.0 Hz, 1H), 6.09 (s, 2H), 4.10 (s, 3H) | 3.80 (B) | 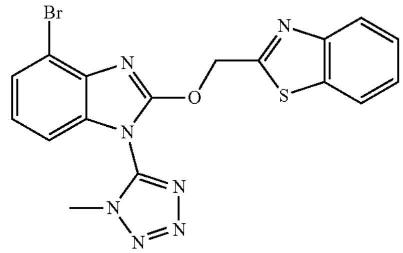 [SMILES: Cn1nnnc1-n1c(OCc2nc3ccccc3s2)nc2c(Br)cccc21] |
| 105[b] | E9 | 1-methylbenzimidazole-2-methanol | 41% | 7.77 (d, J = 8.0 Hz, 1H), 7.49 (dd, J = 8.0, 1.0 Hz, 1H), 7.43 (d, J = 7.9 Hz, 1H), 7.41-7.36 (m, 1H), 7.33 (ddd, J = 8.2, 7.1, 1.3 Hz, 1H), 7.21 (dd, J = 8.1, 1.0 Hz, 1H), 7.13 (t, J = 8.0 Hz, 1H), 5.97 (s, 2H), 4.09 (s, 3H), 4.07 (s, 3H) | 3.63 (B) | 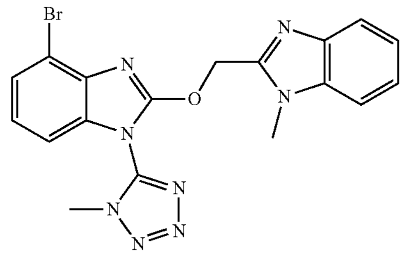 [SMILES: Cn1nnnc1-n1c(OCc2nc3ccccc3n2C)nc2c(Br)cccc21] |
| 106 | E9 | (6-aminopyridin-2-yl)methanol | 77% | (DMSO-d6) 7.53 (dd, J = 8.0, 0.9 Hz, 1H), 7.41-7.36 (m, 2H), 7.18 (t, J = 8.0 Hz, 1H), 6.58 (d, J = 6.9 Hz, 1H), 6.41 (d, J = 8.0 Hz, 1H), 6.07 (s, 2H), 5.48 (s, 2H), 4.12 (s, 3H) | 3.08 (B) | 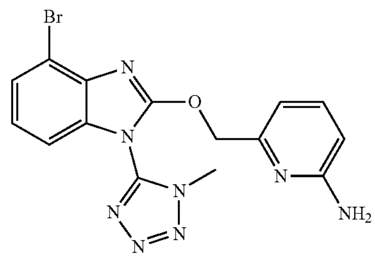 [SMILES: Cn1nnnc1-n1c(OCc2cccc(N)n2)nc2c(Br)cccc21] |
| 107[b] | G | 1-methylbenzimidazole-2-methanol | 36% | (DMSO-d6) 9.28 (s, 1H), 9.27 (s, 1H), 7.64-7.57 (m, 3H), 7.32-7.26 (m, 3H), 7.24-7.18 (m, 2H), 5.91 (s, 2H), 3.84 (s, 3H). | 2.24 (B) | 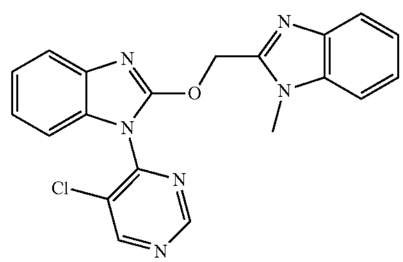 [SMILES: Cn1c(COc2nc3ccccc3n2-c2ncncc2Cl)nc2ccccc21] |

[a]RT = LCMS retention time in minutes using indicated method (A-F); [b]LHMDS (1M in THF) was used instead of NaH.

Example 108—2-(((1-(1-Methyl-1H-tetrazol-5-yl)-1H-benzo[d]imidazol-2-yl)oxy)methyl)pyridin-4-amine 108

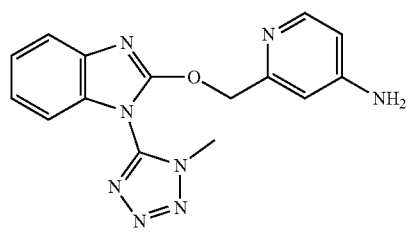 [SMILES: Cn1nnnc1-n1c(OCc2cc(N)ccn2)nc2ccccc21]

A solution of N-(2-(((1-(1-methyl-1H-tetrazol-5-yl)-1H-benzo[d]imidazol-2-yl)oxy)methyl)pyridin-4-yl)hydroxylamine X (40 mg, 0.12 mmol) in methanol (3 mL) was treated with iron powder (20 mg, 0.35 mmol), ammonium chloride (29 mg, 0.53 mmol) and water (1 mL), stirred with heating under reflux for 2 h then filtered through diatomaceous earth. The filter was washed with more MeOH and DCM/MeOH. Filtrates were concentrated in vacuo, partitioned between EtOAc (25 mL) and water (25 mL) and the aq. layer extracted with more EtOAc (25 mL). Organics were washed with brine and dried (MgSO₄) to give impure product (14 mg, discarded). The combined aq. layers were basified with 1M aq. NaOH to pH>10 and extracted further with EtOAc (2×40 mL) as before then triturated with ether to give 2-(((1-(1-methyl-1H-tetrazol-5-yl)-1H-benzo[d]imidazol-2-yl)oxy)methyl)pyridin-4-amine 108 (29 mg, 76%) as a beige solid.

¹H NMR (500 MHz, DMSO) δ 7.95 (d, J=5.6 Hz, 1H), 7.58 (d, J=7.9 Hz, 1H), 7.35 (dd, J=7.9, 0.6 Hz, 1H), 7.30 (td, J=7.7, 1.3 Hz, 1H), 7.27-7.22 (m, 1H), 6.53 (d, J=2.0 Hz, 1H), 6.41 (dd, J=5.6, 2.2 Hz, 1H), 6.20 (s, 2H), 5.48 (s, 2H), 4.11 (s, 3H); LCMS (method B): 2.70 min (323.1, MH⁺).

Example 109—2-((1-Methyl-1H-benzo[d]imidazol-2-yl)methoxy)-1-(1-methyl-1H-tetrazol-5-yl)-4-phenyl-1H-benzo[d]imidazole 109

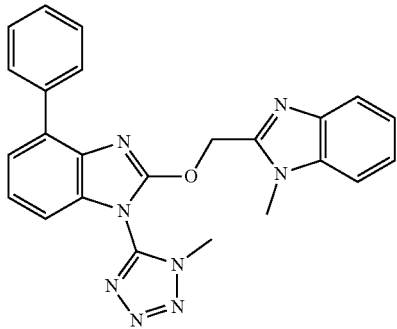 [SMILES: Cn1nnnc1-n1c(OCc2nc3ccccc3n2C)nc2c(-c3ccccc3)cccc21]

A solution of 4-bromo-2-((1-methyl-1H-benzo[d]imidazol-2-yl)methoxy)-1-(1-methyl-1H-tetrazol-5-yl)-1H-benzo[d]imidazole (53 mg, 0.12 mmol) and phenylboronic acid (29 mg, 0.24 mmol) in 1,4-dioxane (2 mL) was treated with potassium carbonate (50 mg, 0.36 mmol) and water (0.5 mL), deoxygenated with a stream of nitrogen for 5 min, then treated with [1,1'-bis(diphenylphosphino)ferrocene]dichloropalladium(II), complex with dichloromethane (10 mg, 0.012 mmol) and irradiated in the microwave at 100° C. for 30 min under nitrogen. The mixture was diluted with water (15 mL) and extracted with EtOAc (2×15 mL). The organics were washed with water (2×15 mL) and brine, dried (MgSO$_4$) and chromatographed on silica (12 g Claricep cartridge) eluting with 20-35% EtOAc/DCM to give 2-((1-methyl-1H-benzo[d]imidazol-2-yl)methoxy)-1-(1-methyl-1H-tetrazol-5-yl)-4-phenyl-1H-benzo[d]imidazole 109 (15 mg, 29%), as a white solid.

$^1$H NMR (500 MHz, CDCl$_3$) δ 7.90-7.83 (m, 2H), 7.78 (d, J=8.0 Hz, 1H), 7.50 (t, J=7.6 Hz, 2H), 7.46 (dd, J=7.7, 1.0 Hz, 1H), 7.42 (t, J=7.4 Hz, 1H), 7.40-7.36 (m, 2H), 7.35-7.30 (m, 2H), 7.21 (dd, J=8.0, 1.0 Hz, 1H), 5.91 (s, 2H), 4.10 (s, 3H), 3.86 (s, 3H); LCMS (method B): 2.88 min (437.2, MH$^+$).

Example 110—Testing the Biological Activity of Compounds of the Invention

The activity of compounds of the invention was assessed by testing against certain oomycete plant pathogens and representative data are presented in Table 1.

Amended Agar Assay

Testing was carried out on potato dextrose agar (PDA) amended with each compound at a test concentration of typically 20 ppm or 2 ppm. Amended agar was poured into three replicate 9 cm petri dishes. Each replicate dish was inoculated in the centre with a 5 mm agar plug taken from the leading edge of a culture aged between 2 and 7 days old; the age of the culture was dependant on the growth rate of the pathogen being tested. The test pathogens were *Pythium ultimum* and *Phytophthora cinnamomi*. Plates were incubated at 18° C. and the diameter of each colony measured before growth on the fastest growing plate reached the plate edge. This varied between 2 and 7 days depending on the growth rate of test pathogens. The % reduction in colony growth compared to the control plate was calculated for each pathogen. The results are provided in Table 1, in which D represents no control detected at this concentration; C represents up to 50% control; B from 50 to 99% control; and A represents a control of greater than 99%, i.e. no detectable colony growth.

Alternatively, or in addition, the same assay was conducted at descending test concentrations with 5-fold dilutions typically down to 0.032 ppm though sometimes as low as 0.00026 ppm, and an EC$_{50}$ (the concentration at which 50% control would be achieved) was determined. The results are provided in Table 1 in which G represents no control detected at 20 ppm, F represents an EC$_{50}$ of ≥20 ppm and E represents an EC$_{50}$ of less than 20 ppm.

96 Well Plate Test

Compounds were screened in 96 well plates with 10 compounds per plate. Each compound was screened using agar amended to 20, 2, 0.2 and 0.02 ppm, with proline at 50 and 10 ppm and 0.2% DMSO used as controls. Each test concentration and standard was replicated twice on a plate. Compounds were screened against *Phytophthora cactorum*. The agar used in the test is a 1% potato dextrose agar. 1000 spores/mL agar were added to the appropriate agar. A ×10 stock solution in 2% DMSO was produced for each dose i.e. 200, 20, 2 and 0.2 ppm, and 10 μl of this added to the appropriate wells on the plate. An equivalent amount of 2% DMSO and proline stock at 500 and 100 ppm were added for the controls. To each well 90 μl of the appropriate agar spore suspension was added to give the required final well concentrations. Plates were incubated at room temperature (18° C.) and assessed after 2 to 3 days. The amount of pathogen growth in each well was compared to the DMSO controls and an EC$_{50}$ concentration was calculated. The results are provided in Table 1 in which H represents no control detected at 20 ppm, G represents no control detected at 2 ppm (where the highest test concentration in the assay was 2 ppm), F represents an EC$_{50}$ of ≥20 ppm, E represents an EC$_{50}$ of less than 20 ppm.

TABLE 1

| | % control or EC$_{50}$ | | | | |
|---|---|---|---|---|---|
| | Pythium ultimum | | | Phytophthora cinnamomi | Phytophthora spp.‡ |
| Compound | 20 ppm | 2 ppm | EC$_{50}$ | 20 ppm | EC$_{50}$ |
| 1 | A | | | B | |
| 2 | D | | | | H |
| 3 | A | B | | | F |
| 4 | A | A | | | E |
| 5 | C | D | | | H |
| 6 | A | A | | | F |
| 7 | | A | | | E |
| 8 | | B | | | F |
| 9 | | C | | | H |
| 10 | | B | | | F |
| 11 | A | A | | | E |
| 12 | A | A | | | E |
| 13 | A | B | | | E |
| 14 | A | A | | | E |
| 15 | A | C | | | H |
| 16 | | C | | | F |
| 17 | | C | | | F |
| 18 | | C | | | H |
| 19 | | C | | | H |
| 20 | | | E | | E* |
| 21 | B | D | | | H |
| 22 | | B | | | F |
| 23 | | B | | | F |
| 24 | | B | | | E |
| 25 | | C | | | H |
| 26 | D | | | D | |
| 27 | C | | | D | |
| 28 | | | E | | E* |

TABLE 1-continued

| | % control or EC$_{50}$ | | | | |
|---|---|---|---|---|---|
| | Pythium ultimum | | | Phytophthora cinnamomi | Phytophthora spp.‡ |
| Compound | 20 ppm | 2 ppm | EC$_{50}$ | 20 ppm | EC$_{50}$ |
| 29 | A | | E | A | E* |
| 30 | | A | | | E |
| 31 | D | | | B | |
| 32 | | C | | | H |
| 33 | C | | | B | |
| 34 | | D | | | H |
| 35 | A | | | | E |
| 36 | A | | | | E |
| 37 | A | | | | E |
| 38 | A | | | | E |
| 39 | A | | | | E |
| 40 | A | | | | E |
| 41 | D | | | | G |
| 42 | A | | | | E |
| 43 | A | | | | E |
| 44 | A | | | | E |
| 45 | A | | | | E |
| 46 | B | | | | G |
| 47 | A | | | | E |
| 48 | A | | | | E |
| 49 | D | | | | H |
| 50 | A | | | | E |
| 51 | A | | | | E |
| 52 | D | | | | H |
| 53 | D | | | | H |
| 54 | D | | | | H |
| 55 | A | | | | E |
| 56 | C | | | | F |
| 57 | D | | | | H |
| 58 | D | | | | H |
| 59 | A | | | | E |
| 60 | A | | | | E |
| 61 | A | | | | E |
| 62 | A | | | | E |
| 63 | A | | | | E |
| 64 | A | | | | E |
| 65 | B | | | | F |
| 66 | A | | | | E |
| 67 | A | | | | G |
| 68 | C | | | | H |
| 69 | B | | | | F |
| 70 | A | | | | E |
| 71 | D | | | | F |
| 72 | C | | | | H |
| 73 | A | | | | E |
| 74 | A | | | | E |
| 75 | B | | | | F |
| 76 | A | | | | F |
| 77 | A | | | | E |
| 78 | B | | | | E |
| 79 | B | | | | E |
| 80 | A | | | | E |
| 81 | A | | | | E |
| 82 | A | | | | E |
| 83 | A | | | | E |
| 84 | A | | | | E |
| 85 | A | | | | E |
| 86 | A | | | | E |
| 87 | A | | | | E |
| 88 | A | | | | E |
| 89 | A | | | | E |
| 90 | A | | | | E |
| 91 | A | | | | E |
| 92 | A | | | | E |
| 93 | A | | | | E |
| 94 | A | | | | E |
| 95 | A | | | | E |
| 96 | A | | | | E |
| 97 | A | | | | E |
| 98 | A | | | | E |
| 99 | A | | | | E |
| 100 | A | | | | E |
| 101 | B | | | | E |
| 102 | B | | | | E |
| 103 | A | | | | E |
| 104 | A | | | | E |
| 105 | A | | | | E |
| 106 | B | | | | E |
| 108 | D | | | | F |

‡Compounds were tested in 96 well plate assay vs. *Phytophthora cactorum* or where indicated by * they were tested in the amended agar assay vs. *Phytophthora cinnamomi*.

Thus, many of the compounds of the invention showed good control over the pathogens tested (e.g. examples 1, 3, 4, 7, 11, 12, 13, 14, 20, 24, 28, 29, 30, 35-40, 42-45, 47, 48, 50, 51, 55, 59-64, 66, 70, 73, 74, 77 and 79-106).

The invention claimed is:
1. A compound of formula (I), or an agronomically acceptable salt or N-oxide thereof:

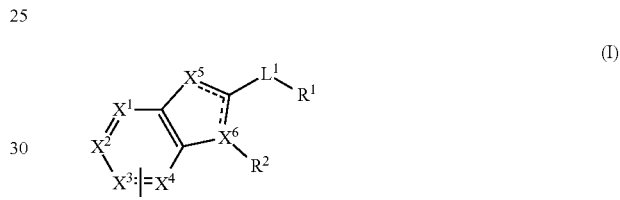

wherein -L$^1$- is independently —(CR$^4$R$^4$)$_n$—O—C(R$^4$R$^4$)$_n$—;
wherein X$^1$, X$^2$, X$^3$ and X$^4$ are each selected from carbon and nitrogen; wherein no more than three of X$^1$, X$^2$, X$^3$ and X$^4$ are nitrogen;
======= is selected from a double bond or a single bond;
X$^6$ is independently selected from N and C; wherein when X$^6$ is N, the ======= bond to which X$^6$ is attached is a single bond, the ======= bond to which X$^5$ is attached is a double bond and X$^5$ is selected from N and CR$^{5a}$; or when X$^6$ is C, the ======= bond to which X$^6$ is attached is a double bond, the ======= bond to which X$^5$ is attached is a single bond, and X$^5$ is NR$^{5b}$;
R$^1$ is a heteroaryl group independently selected from thiazole and 6-, 9- or 10-membered heteroaryl group, wherein said heteroaryl group is optionally substituted with a single R$^6$ group and/or from 1 to 4 R$^7$ groups; wherein R$^1$ has a nitrogen atom in the ring by which R$^1$ is attached to the rest of the molecule, said nitrogen atom being directly attached to the carbon atom in the ring by which R$^1$ is attached to the rest of the molecule;
R$^2$ is independently selected from 5- or 6-membered heteroaryl, optionally further substituted with from 1 to 4 R$^8$ groups;
R$^3$, R$^7$ and R$^8$ are each independently at each occurrence selected from: halo, nitro, cyano, NR$^9$R$^{10}$, OR$^{11}$, SR$^{10}$, S(O)R$^{10}$, OS(O)$_2$R$^{10}$, S(O)$_2$R$^{10}$, S(O)$_2$NR$^{10}$R$^{10}$, CO$_2$R$^{10}$, C(O)R$^{10}$, CONR$^{10}$R$^{10}$, C$_1$-C$_6$-alkyl, C$_2$-C$_6$-alkenyl, C$_2$-C$_6$-alkynyl, C$_1$-C$_6$-haloalkyl, phenyl, C$_3$-C$_6$-cycloalkyl, 3- to 6-membered heterocycloalkyl, 5- or 6-membered heteroaryl, and —O—C$_1$-C$_6$-haloalkyl;

$R^4$ is independently selected from H, F, $C_1$-$C_4$-alkyl and $C_1$-$C_4$-haloalkyl;

or two $R^4$ groups that are attached to the same carbon, together with the carbon to which they are attached, form a $C_3$-$C_5$-cycloalkyl group;

$R^{5a}$ is independently selected from H, halo and $C_1$-$C_4$-alkyl;

$R^{5b}$ is independently selected from H and $C_1$-$C_4$-alkyl;

$R^6$ is independently selected from H and $NHR^{13}$;

$R^9$ is independently at each occurrence selected from H, $C_3$-$C_6$-cycloalkyl, $C_1$-$C_6$-alkyl, C(O)—$C_1$-$C_6$-alkyl, C(O)O—$C_1$-$C_6$-alkyl, $C(O)NR^{10}R^{10}$, and $S(O)_2$—$C_1$-$C_6$-alkyl;

$R^{10}$, $R^{15}$ and $R^{19}$ are each independently at each occurrence selected from H, $C_1$-$C_6$-alkyl and $C_3$-$C_6$-cycloalkyl;

or where two $R^{10}$ groups are attached to the same nitrogen atom, the two $R^{10}$ groups together with the nitrogen atom to which they are attached may form a 4- to 7-membered heterocycloalkyl ring;

or $R^9$ and $R^{10}$ together with the nitrogen to which they are attached form a 4- to 7-membered heterocycloalkyl ring;

$R^{11}$ is independently at each occurrence selected from H, $C_1$-$C_6$-alkyl, $C_1$-$C_6$-haloalkyl, $C_3$-$C_6$-alkenyl, $C_3$-$C_6$-alkynyl, $C_0$-$C_3$-alkylene-$R^{11a}$; wherein $R^{11a}$ is independently selected from $C_3$-$C_6$-cycloalkyl and 3- to 6-membered heterocycloalkyl;

$R^{13}$ is independently selected from: H, $S(O)_2$—$C_1$-$C_6$-alkyl, $C_1$-$C_6$-alkyl, $C_3$-$C_7$-cycloalkyl, $C_1$-$C_4$-alkylene-$R^{13a}$, phenyl, 4- to 7-membered heterocycloalkyl, 5-, 6-, 9- or 10-membered heteroaryl, $C(S)$-$L^2$-$R^{14}$ and $C(O)$-$L^2$-$R^{14}$; wherein $R^{13a}$ is independently selected from: $C_3$-$C_6$-cycloalkyl, 4- to 7-membered heterocycloalkyl, phenyl, 5- or 6-membered heteroaryl, —O—$C_0$-$C_3$-alkylene-$C_3$-$C_6$-cycloalkyl, —O—$C_0$-$C_3$-alkylene-phenyl and —O—$C_1$-$C_4$-alkyl;

-$L^2$- is absent or is independently selected from —O—, —S—, and —$NR^{15}$—;

$R^{14}$ is independently selected from $C_1$-$C_8$-alkyl, $C_1$-$C_8$-haloalkyl, $C_3$-$C_8$-alkenyl, $C_3$-$C_8$-alkynyl, $C_0$-$C_3$-alkylene-$R^{16}$; and —$CR^{17}R^{17}L^3R^{18}$;

-$L^3$- is independently selected from —O—, —S— and —$NR^{19}$—;

$R^{17}$ is independently at each occurrence selected from F, H and $C_1$-$C_4$-alkyl;

$R^{18}$ is independently selected from H, $C_1$-$C_8$-alkyl, $C_1$-$C_8$-haloalkyl, $C_3$-$C_8$-alkenyl, $C_3$-$C_8$-alkynyl and $C_0$-$C_3$-alkylene-$R^{20}$;

$R^{16}$ and $R^{20}$ are each independently at each occurrence selected from $C_3$-$C_6$-cycloalkyl, 3- to 6-membered heterocycloalkyl, 5- or 6-membered heteroaryl and phenyl;

y is an integer selected from 0, 1, 2, 3 and 4;

n is independently at each occurrence selected from 0, 1, 2 and 3;

with the proviso that where -$L^1$- is —O—$(CR^4R^4)$—, $R^{13}$ is not selected from $C(S)$-$L^2$-$R^{14}$ and $C(O)$-$L^2$-$R^{14}$, and $R^7$ is independently at each occurrence selected from: halo, nitro, cyano, $NR^{10}R^{10}$, $NR^{10}S(O)_2R^{10}$, $OR^{11}$, $SR^{10}$, $S(O)R^{10}$, $OS(O)_2R^{10}$, $S(O)_2R^{10}$, $S(O)_2NR^{10}R^{10}$, $CO_2R^{10}$, $C(O)R^{10}$, $CONR^{10}R^{10}$, $C_1$-$C_6$-alkyl, $C_2$-$C_6$-alkenyl, $C_2$-$C_6$-alkynyl, $C_1$-$C_6$-haloalkyl, phenyl, $C_3$-$C_6$-cycloalkyl, 3- to 6-membered heterocycloalkyl, 5- or 6-membered heteroaryl and —O—$C_1$-$C_6$-haloalkyl wherein where any $R^1$-$R^{20}$ group is an alkyl, alkenyl, alkynyl, haloalkyl, cycloalkyl, heterocycloalkyl, phenyl or heteroaryl group, that alkyl, haloalkyl, cycloalkyl, heterocycloalkyl, phenyl or heteroaryl group is optionally substituted, where chemically possible, by 1 to 5 substituents which are each independently selected at each occurrence from: oxo, =$NR^a$, =$NOR^a$, halo, nitro, cyano, $NR^aR^b$, $NR^aS(O)_2R^a$, $NR^aC(O)R^a$, $NR^a$-$CONR^aR^a$, $NR^aCO_2R^a$, $OR^a$, $SR^a$, $S(O)R^a$, $S(O)_2R^a$, $S(O)_2NR^aR^a$, $CO_2R^a$, $C(O)R^a$, $CONR^aR^a$, $C_1$-$C_4$-alkyl, $C_2$-$C_4$-alkenyl, $C_2$-$C_4$-alkynyl, $C_3$-$C_6$-cycloalkyl and $C_1$-$C_4$-haloalkyl; wherein $R^a$ is independently at each occurrence selected from H and $C_1$-$C_4$-alkyl; and $R^b$ is independently at each occurrence selected from H, $C_3$-$C_6$-cycloalkyl, $C_1$-$C_4$-alkyl, C(O)—$C_1$-$C_4$-alkyl and $S(O)_2$—$C_1$-$C_4$-alkyl;

provided that the compound is not selected from:

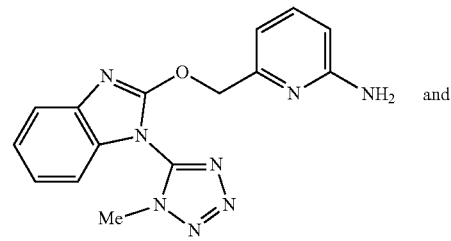

and

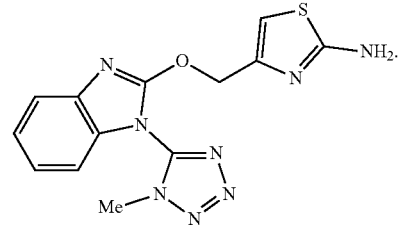

2. A compound of claim 1, wherein $X^5$ and $X^6$ are each N.

3. A compound of claim 1, wherein $X^1$, $X^2$, $X^3$ and $X^4$ are each carbon.

4. A compound of claim 1, wherein $L^1$ is —O—$CR^4R^4$—.

5. A compound of claim 4, wherein -$L^1$- is —O—$CH_2$—.

6. A compound of claim 1, wherein $R^1$ has the structure:

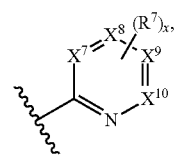

wherein $X^7$, $X^8$ and $X^9$ are each selected from carbon and nitrogen; $X^{10}$ is independently selected from nitrogen and $CR^6$; providing no more than one of $X^7$, $X^8$, $X^9$ and $X^{10}$ are nitrogen; and wherein x is an integer selected from 0, 1, 2 and 3.

7. A compound of claim 6, wherein $R^1$ has the structure:

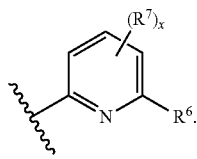

8. A compound of claim 7, wherein $R^1$ has the structure:

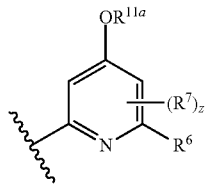

wherein $R^{11a}$ is independently selected from H, $C_1$-$C_6$-alkyl, $C_1$-$C_6$-haloalkyl, and $C_3$-$C_6$-cycloalkyl; and z is an integer selected from 0, 1 and 2.

9. A compound of claim 1, wherein $R^1$ has the structure:

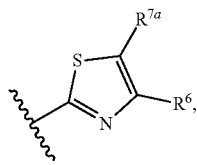

wherein $R^{7a}$ is independently selected from H, halo, nitro, cyano, $NR^{10}R^{10}$, $OR^{11}$, $SR^{10}$, $S(O)R^{10}$, $S(O)_2R^{10}$, $OS(O)_2OR^{10}$, $S(O)_2NR^{10}R^{10}$, $CO_2R^{10}$, $C(O)R^{10}$, $CONR^{10}R^{10}$, $C_1$-$C_4$-alkyl, $C_2$-$C_4$-alkenyl, $C_2$-$C_4$-alkynyl, and $C_1$-$C_4$-haloalkyl.

10. A compound of claim 1, wherein $R^6$ is H.

11. A compound of claim 1, wherein $R^6$ is $NHR^{13}$.

12. A compound of claim 11, wherein $R^{13}$ may be independently selected from:
$C_1$-$C_6$-alkyl, $C_3$-$C_6$-cycloalkyl, and $C_1$-$C_4$-alkylene-$R^{13a}$.

13. A compound of claim 1, wherein $R^2$ is substituted at a position adjacent to the point of connection of $R^2$ to the rest of the molecule with an $R^{8b}$ group, wherein $R^{8b}$ is selected from chloro, bromo, $C_1$-$C_4$alkyl, $C_2$-$C_4$-alkenyl, $C_2$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

14. A compound of claim 1, wherein $R^2$ has the structure:

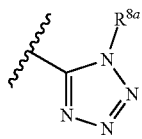

wherein $R_{8a}$ independently selected from $C_1$-$C_4$-alkyl, $C_3$-$C_4$-alkenyl, $C_3$-$C_4$-alkynyl, phenyl, $C_3$-$C_6$-cycloalkyl, 3- to 6-membered heterocycloalkyl, 5- or 6-membered heteroaryl and $C_1$-$C_4$-haloalkyl.

15. A compound of claim 1, wherein the compound of formula (I) is selected from:

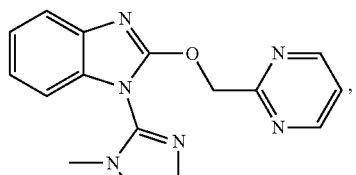

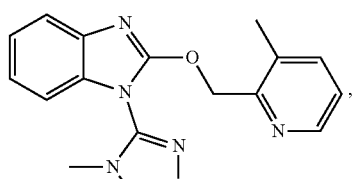

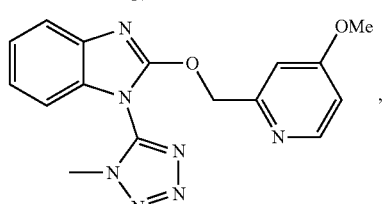

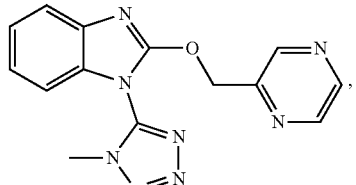

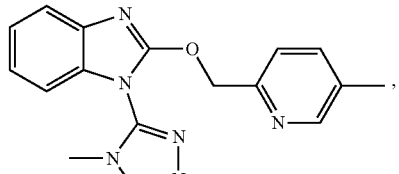

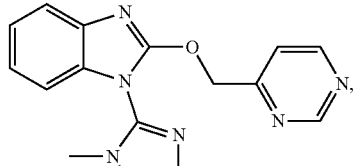

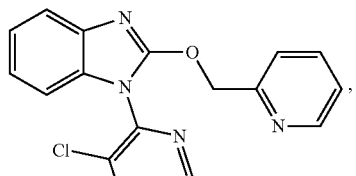

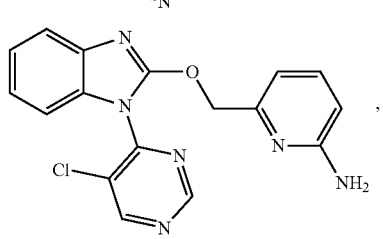

137
-continued
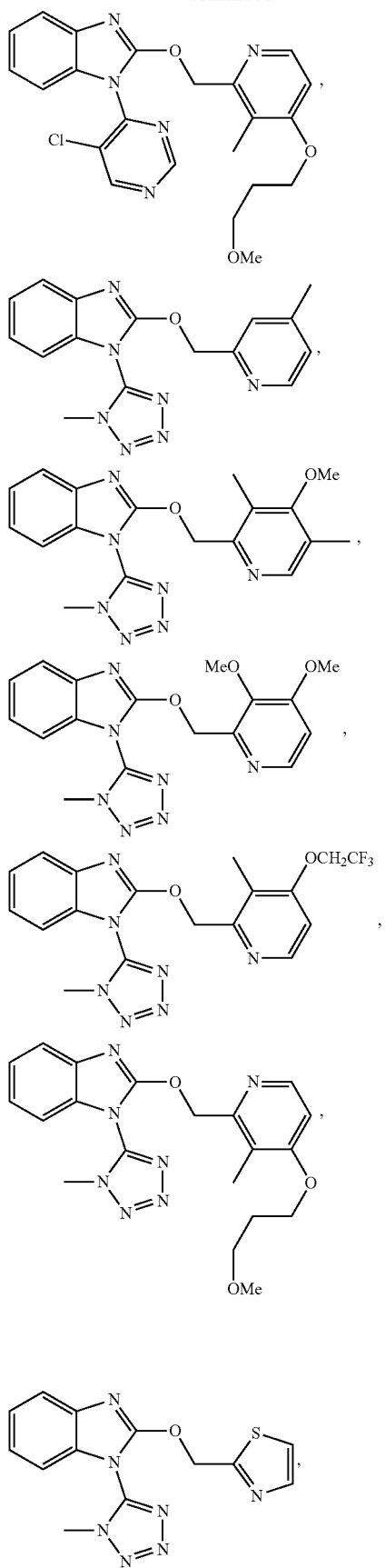
138
-continued
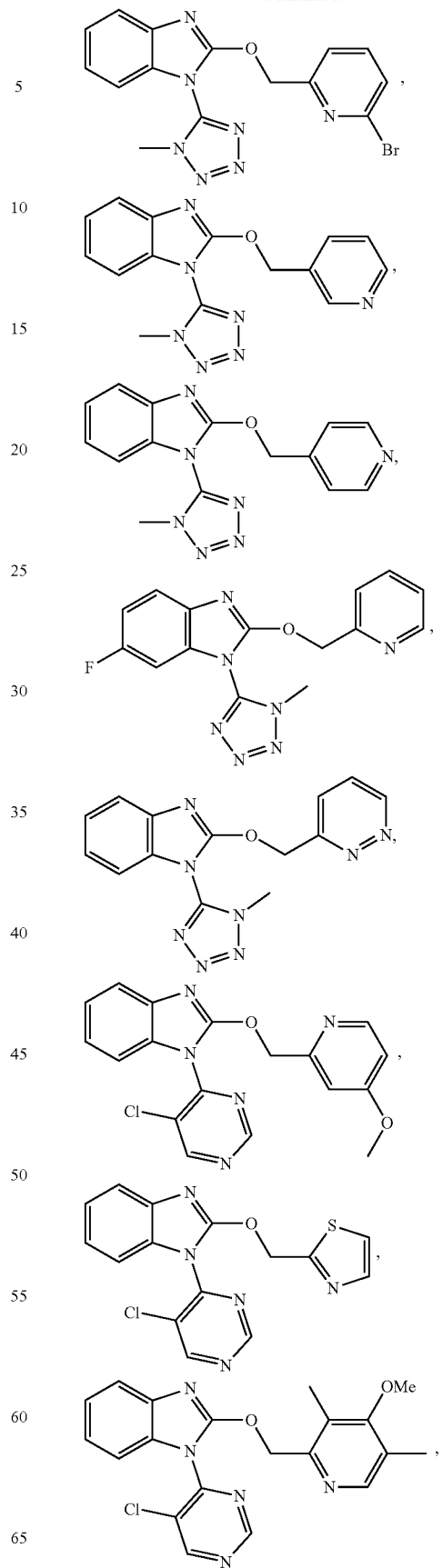

139
-continued
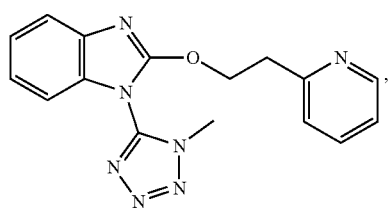
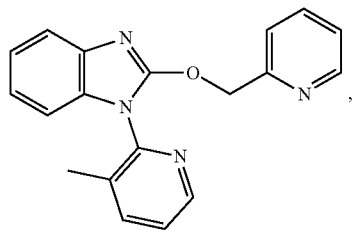
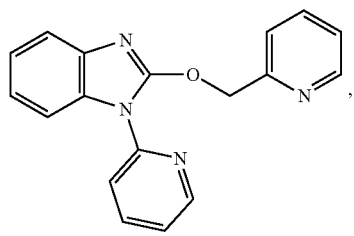
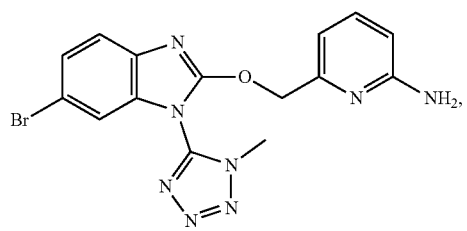
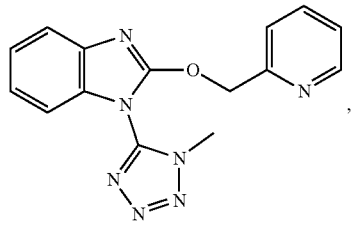
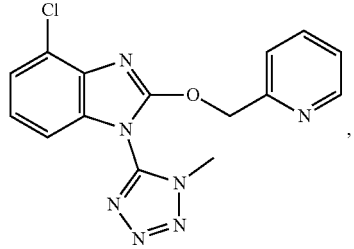
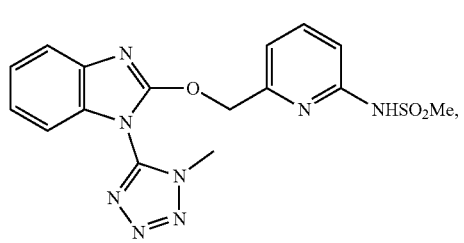
140
-continued
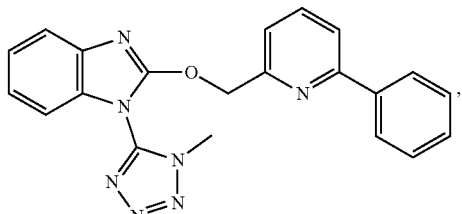
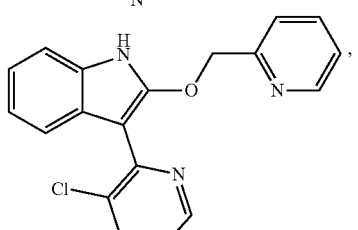
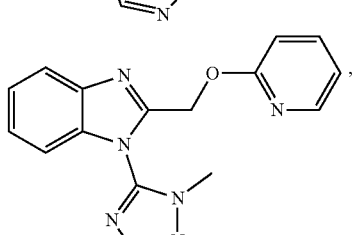
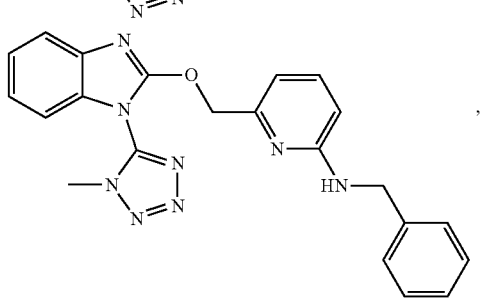
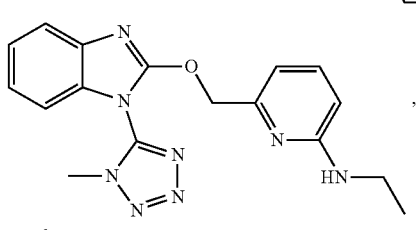
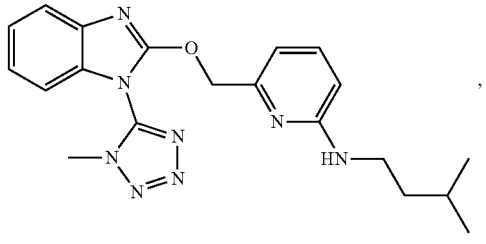
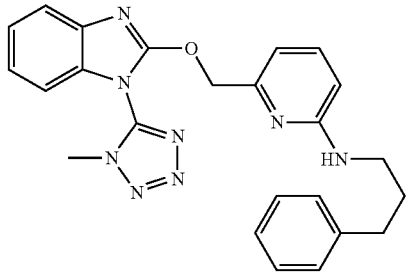

141
-continued
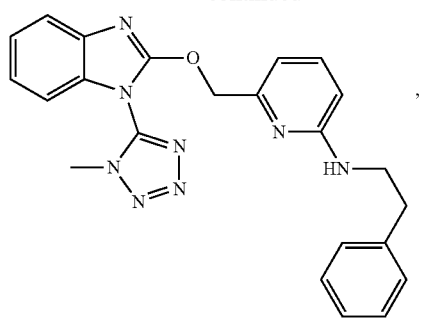
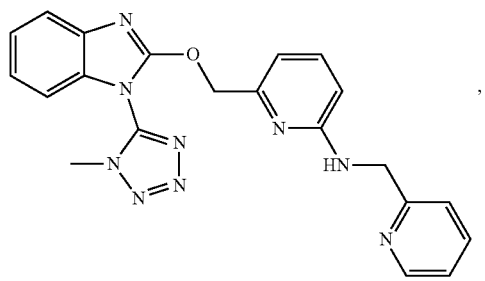
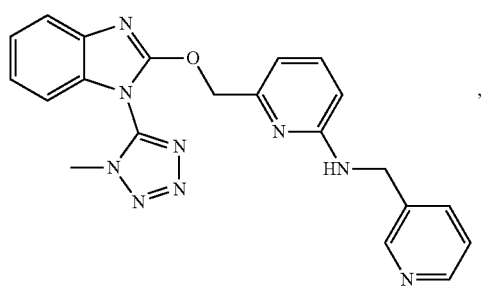
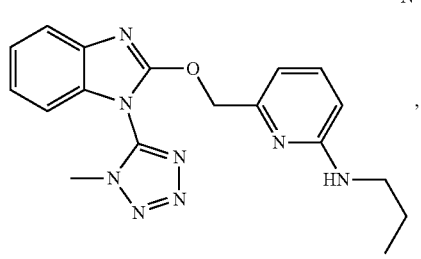
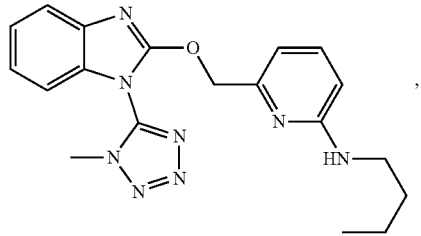
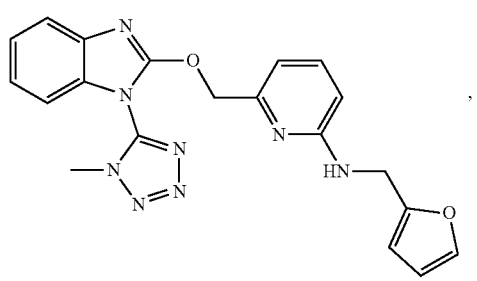
142
-continued
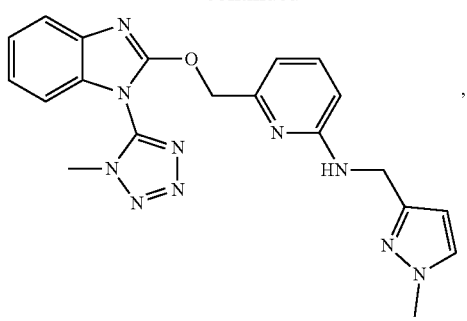
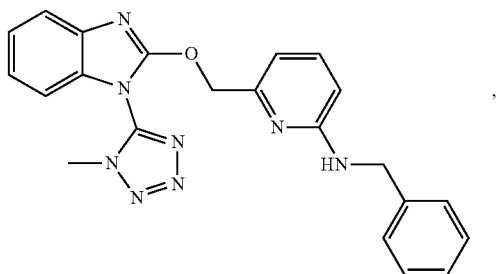
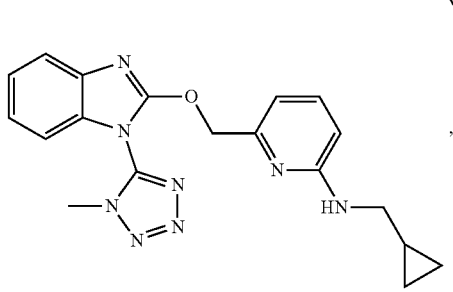
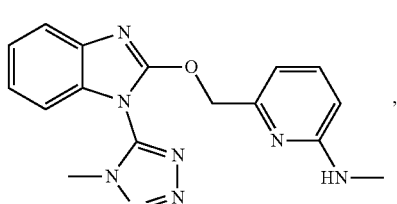
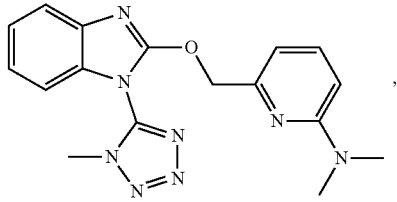
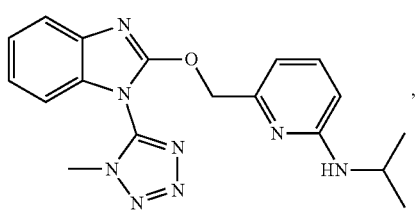

-continued
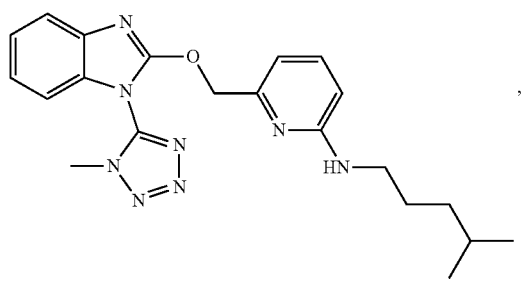,
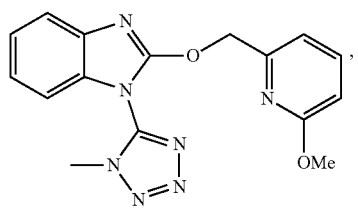,
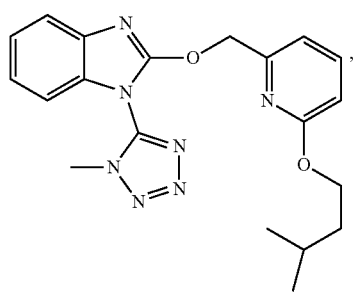,
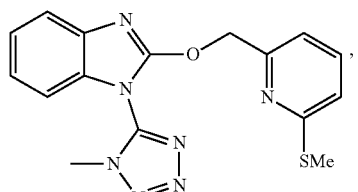,
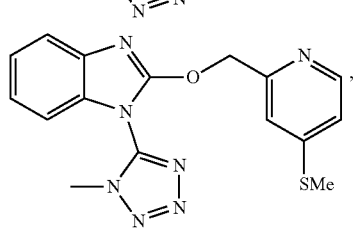,
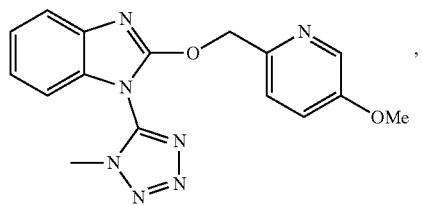,
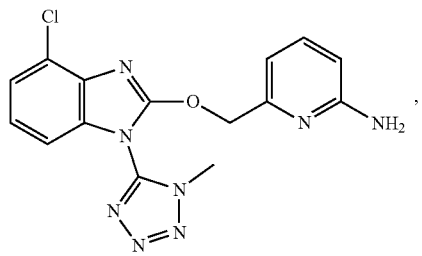,
-continued
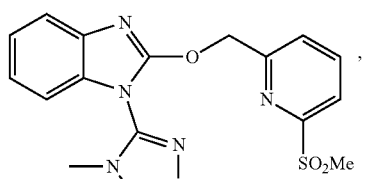,
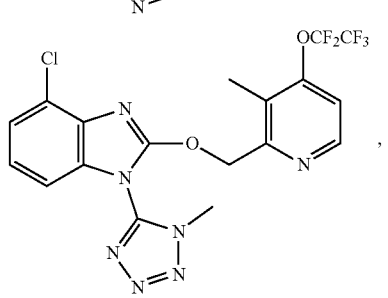,
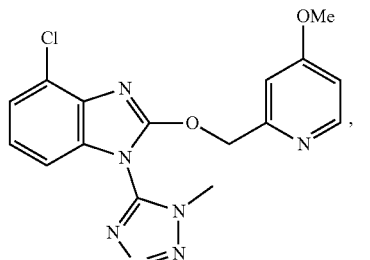,
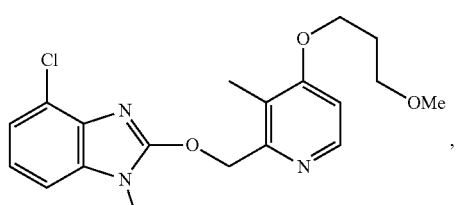,
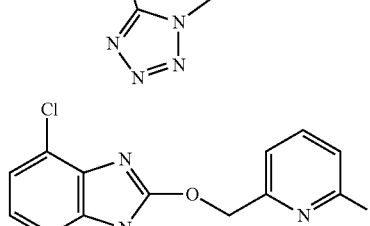,
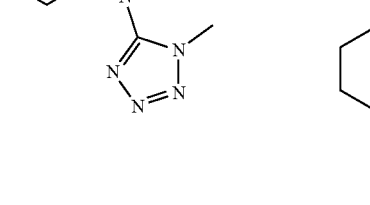,
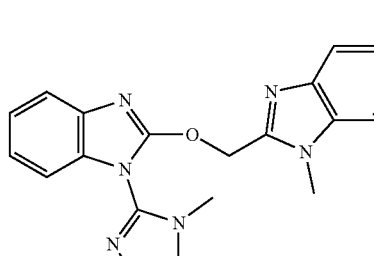, 145
-continued
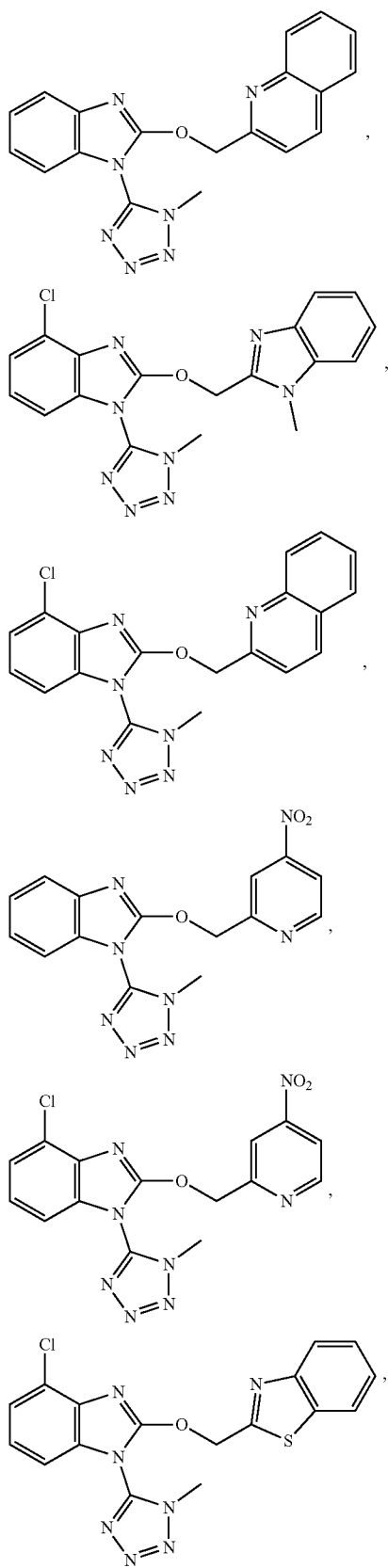
146
-continued
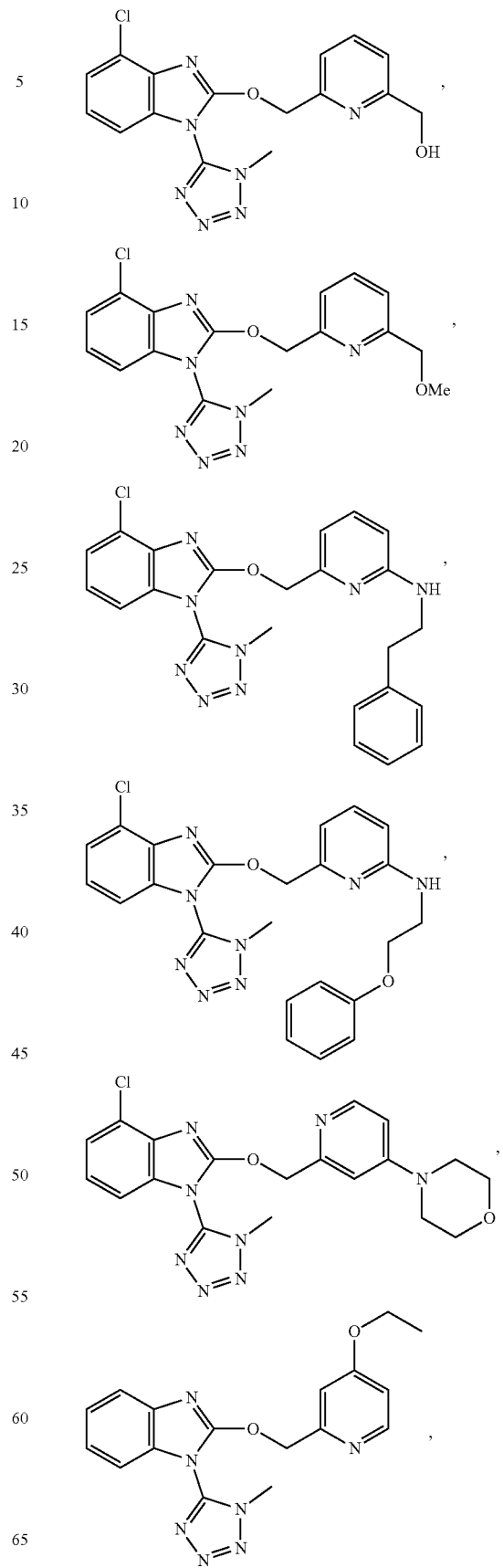

147
-continued
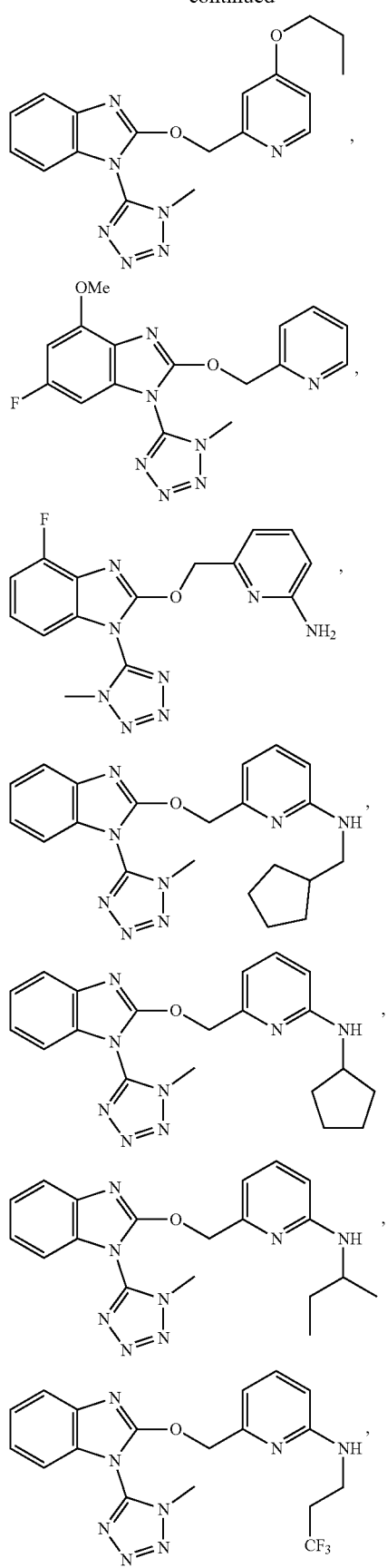
148
-continued
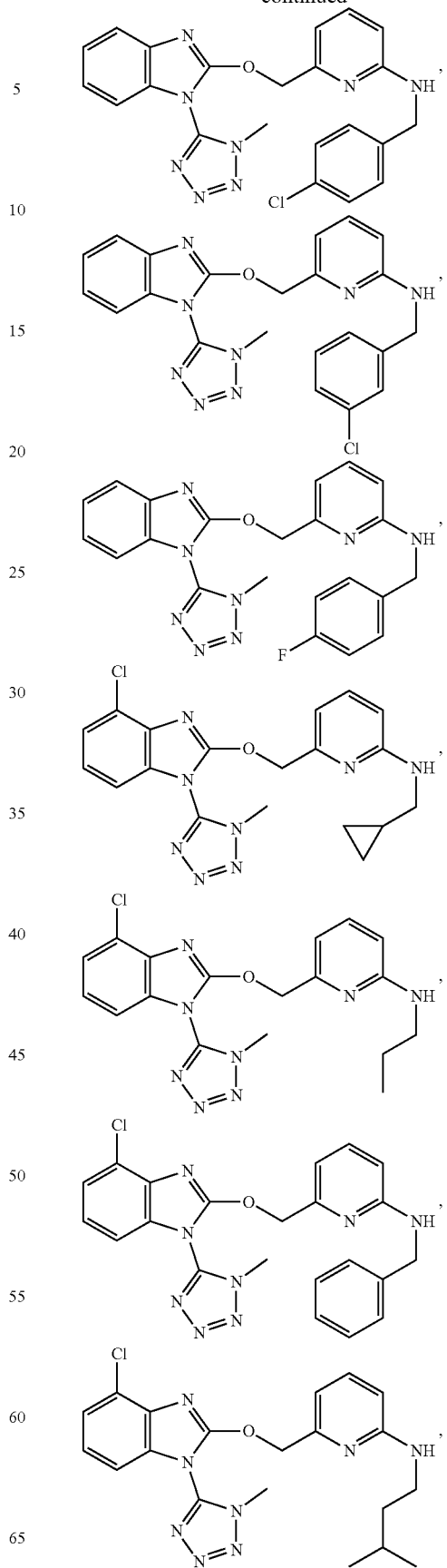

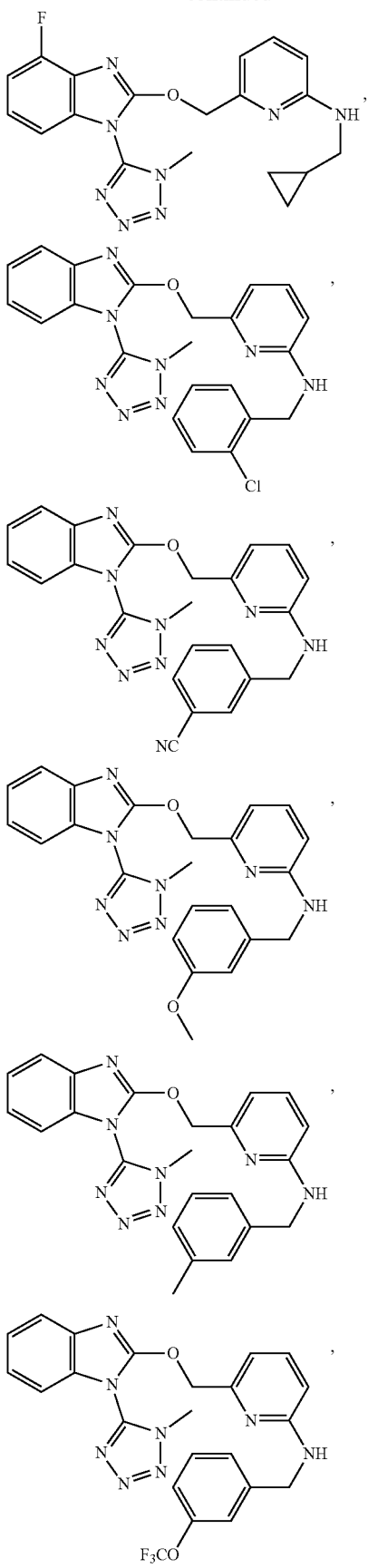
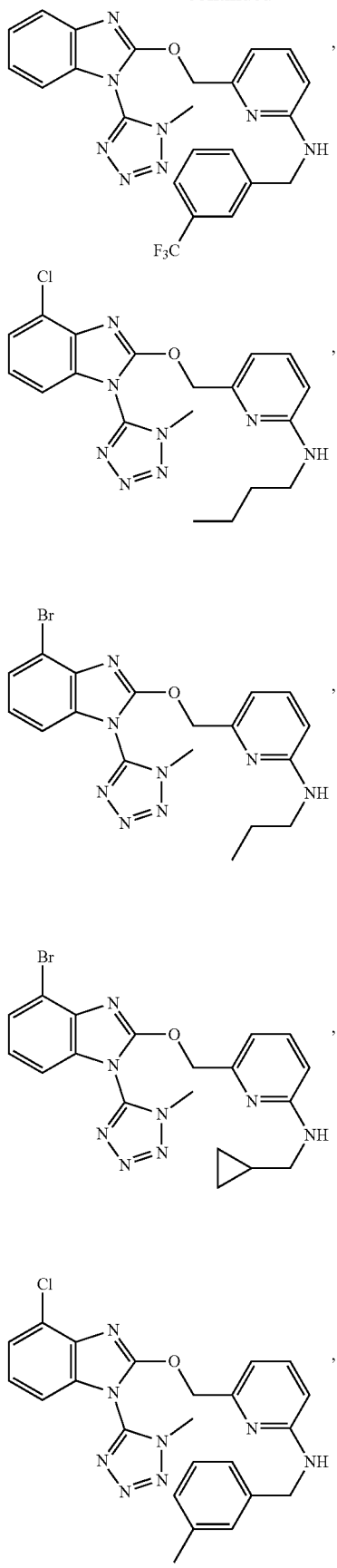

151
-continued

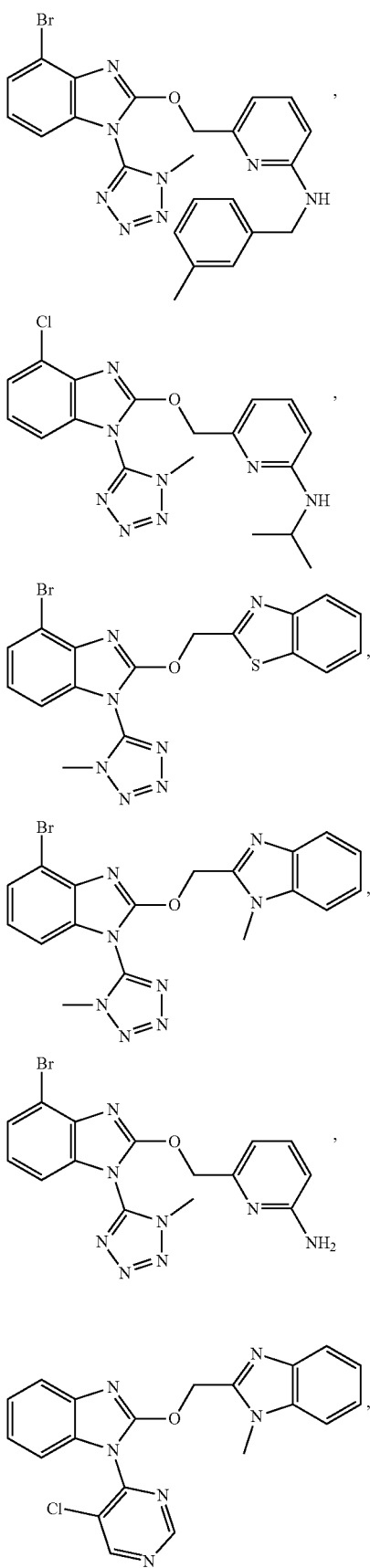

152
-continued

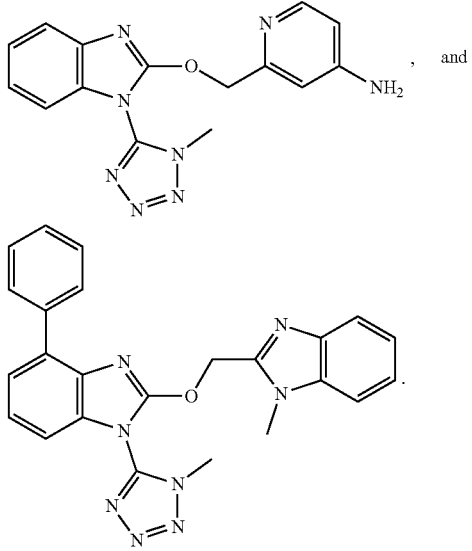

16. A method for controlling fungal diseases, the method comprising applying an agronomically effective and substantially non-phytotoxic quantity of a compound to seeds of plants, to plants themselves or to an area where it is intended that plants will grow; wherein the compound is selected from a compound of claim 1,

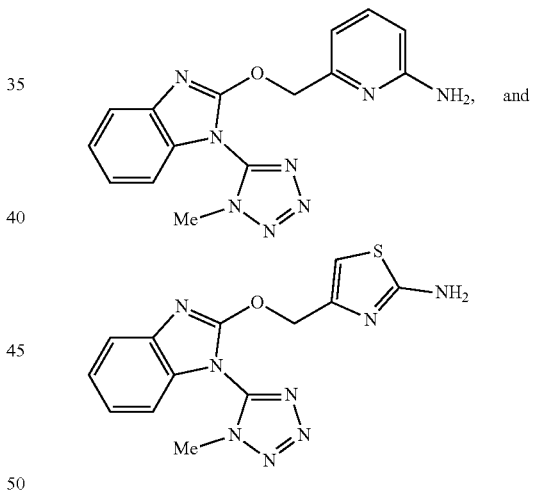

or an agronomically acceptable salt or N-oxide thereof.

17. A fungicidal composition comprising an effective and non-phytotoxic amount of a compound; wherein the compound is selected from a compound of claim 1,

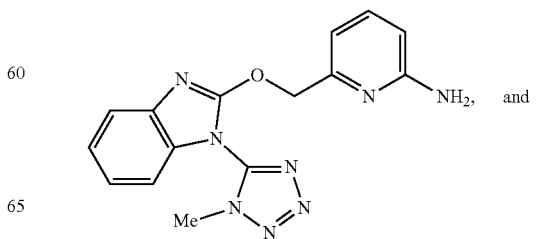

-continued
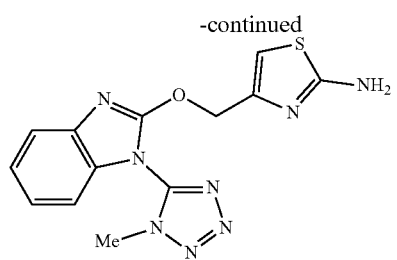
or an agronomically acceptable salt or N-oxide thereof.